(12) United States Patent
McGrew et al.

(10) Patent No.: US 11,692,193 B2
(45) Date of Patent: *Jul. 4, 2023

(54) EXPRESSION FROM TRANSPOSON-BASED VECTORS AND USES

(71) Applicant: Just-Evotec Biologics, Inc., Seattle, WA (US)

(72) Inventors: Jeffrey T. McGrew, Woodinville, WA (US); Pauline S. Smidt, Seattle, WA (US); E-Ching Ong, Seattle, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 292 days.

This patent is subject to a terminal disclaimer.

(21) Appl. No.: 17/190,954

(22) Filed: Mar. 3, 2021

(65) Prior Publication Data

US 2021/0189403 A1 Jun. 24, 2021

Related U.S. Application Data

(60) Division of application No. 16/286,551, filed on Feb. 26, 2019, now Pat. No. 11,098,310, which is a continuation-in-part of application No. 16/072,180, filed as application No. PCT/US2017/015130 on Jan. 26, 2017, now Pat. No. 11,028,410.

(60) Provisional application No. 62/388,391, filed on Jan. 27, 2016.

(51) Int. Cl.
| | |
|---|---|
| *C12N 15/00* | (2006.01) |
| *C12N 15/52* | (2006.01) |
| *C12N 15/65* | (2006.01) |
| *C12N 15/113* | (2010.01) |
| *C12N 15/85* | (2006.01) |
| *C12N 15/67* | (2006.01) |

(52) U.S. Cl.
CPC ............ *C12N 15/52* (2013.01); *C12N 15/113* (2013.01); *C12N 15/65* (2013.01); *C12N 15/67* (2013.01); *C12N 15/85* (2013.01); *C12N 2015/8518* (2013.01); *C12N 2710/22031* (2013.01); *C12N 2800/107* (2013.01); *C12N 2800/90* (2013.01); *C12N 2830/001* (2013.01); *C12N 2830/003* (2013.01); *C12N 2830/60* (2013.01); *C12N 2840/203* (2013.01)

(58) Field of Classification Search
CPC ...... C12N 15/52; C12N 15/113; C12N 15/65; C12N 15/67; C12N 15/85; C12N 2015/8518; C12N 2710/22031; C12N 2800/107; C12N 2800/90; C12N 2830/001; C12N 2830/003; C12N 2830/60; C12N 2840/203

See application file for complete search history.

(56) References Cited

U.S. PATENT DOCUMENTS

| | | |
|---|---|---|
| 5,688,688 A | 11/1997 | Luciw et al. |
| 5,972,650 A | 10/1999 | Yao |
| 6,210,924 B1 | 4/2001 | Hu et al. |
| 6,716,602 B2 | 4/2004 | Andersen et al. |
| 7,693,698 B2 | 4/2010 | Mosyak et al. |
| 8,771,988 B2 | 7/2014 | Goepfert et al. |
| 9,080,183 B2 | 7/2015 | Klein et al. |
| 9,121,036 B2 | 9/2015 | Alphey |
| 9,133,477 B2 | 9/2015 | Alphey |
| 9,260,528 B2 | 2/2016 | Hartman et al. |
| 9,290,552 B2 | 3/2016 | Minshull et al. |
| 9,334,489 B2 | 5/2016 | Devaud et al. |
| 9,340,619 B2 | 5/2016 | Hartman et al. |
| 9,428,767 B2 | 8/2016 | Minshull et al. |
| 9,567,577 B2 | 2/2017 | Jang et al. |
| 9,574,209 B2 | 2/2017 | Minshull et al. |
| 9,580,697 B2 | 2/2017 | Minshull et al. |
| 9,676,860 B2 | 6/2017 | Hartman et al. |
| 9,809,652 B2 | 11/2017 | Greenberg et al. |
| 9,815,903 B2 | 11/2017 | Hartman et al. |
| 9,896,516 B2 | 2/2018 | Bradley et al. |
| 9,924,705 B2 | 3/2018 | Liang et al. |

(Continued)

FOREIGN PATENT DOCUMENTS

| | | |
|---|---|---|
| JP | 2000-515769 A | 11/2000 |
| KR | 20070053798 A | 5/2007 |

(Continued)

OTHER PUBLICATIONS

Shukurov et al (Applied Biochemistry and Microbiology, 2014, vol. 50, No. 9, pp. 802-811; Table in p. 105). (Year: 2014).*

Kim et al in (J of Biotechnology vol. 93, 2002, pp. 183-187). (Year: 2002).*

Kim, Seon-Young et al., "The human elongation factor 1 alpha (EF-1 alpha) first intron highly enhances expression of foreign genes from the murine cytomegalovirus promoter", J. Biotechnol. vol. 93, pp. 183-187 (2002) (as cited by JPO).

(Continued)

*Primary Examiner* — Catherine S Hibbert
(74) *Attorney, Agent, or Firm* — Law Offices of Nisan Steinberg

(57) ABSTRACT

Recombinant expression vectors are disclosed that include a control sequence for recombinant expression of proteins of interest; the control sequence combines a mCMV enhancer sequence with a rat EF-1alpha intron sequence. Some of the vectors are useful for tetracycline-inducible expression. Some of the vectors contain a 5' PiggyBac ITR and a 3' PiggyBac ITR to promote genomic integration into a host cell chromosome. A method of selecting a stable production cell line for manufacturing a protein of interest is also disclosed. Also disclosed are mammalian host cells comprising the inventive recombinant expression vectors and a method of producing a protein of interest, in vitro, involving the mammalian host cell.

13 Claims, 40 Drawing Sheets

Specification includes a Sequence Listing.

(56) References Cited

U.S. PATENT DOCUMENTS

| | | | |
|---|---|---|---|
| 9,926,567 B2 | 3/2018 | Klein et al. | |
| 9,938,357 B2 | 4/2018 | Bradley et al. | |
| 9,938,358 B2 | 4/2018 | Bradley et al. | |
| 9,957,541 B2 | 5/2018 | Sunstrom | |
| 9,970,025 B2 | 5/2018 | Alphey | |
| 10,041,077 B2 | 8/2018 | Minshull et al. | |
| 10,053,720 B2 | 8/2018 | Hartman et al. | |
| 11,028,410 B2 * | 6/2021 | McGrew | C12N 15/86 |
| 11,261,462 B2 * | 3/2022 | McGrew | C07K 16/00 |
| 2005/0005310 A1 | 1/2005 | Chisholm et al. | |
| 2005/0019925 A1 | 1/2005 | Krummen et al. | |
| 2007/0054303 A1 | 3/2007 | Chisholm et al. | |
| 2010/0062442 A1 | 3/2010 | Burke et al. | |
| 2010/0159489 A1 | 6/2010 | Klein et al. | |
| 2013/0295611 A1 | 11/2013 | Bondensgaard et al. | |
| 2015/0167020 A1 | 6/2015 | Rance et al. | |
| 2016/0208284 A1 | 7/2016 | Huelsmann et al. | |
| 2016/0281106 A1 | 9/2016 | Kim et al. | |
| 2017/0022272 A1 | 1/2017 | Stevens et al. | |
| 2018/0037645 A1 | 2/2018 | Stevens et al. | |

FOREIGN PATENT DOCUMENTS

| | | |
|---|---|---|
| WO | 9900510 A1 | 1/1999 |
| WO | 0139599 A2 | 6/2001 |
| WO | 0240697 A2 | 5/2002 |
| WO | 2005012534 A1 | 2/2005 |
| WO | 2006058900 A1 | 6/2006 |
| WO | 2006063292 A1 | 6/2006 |
| WO | 2007092370 A2 | 8/2007 |
| WO | 2008020960 A1 | 2/2008 |
| WO | 2008096070 A2 | 8/2008 |
| WO | 2009053368 A1 | 4/2009 |
| WO | 2011110864 A1 | 9/2011 |
| WO | 2013092743 A2 | 6/2013 |
| WO | 2013177101 A2 | 11/2013 |
| WO | 2013186371 A1 | 12/2013 |
| WO | 2013190032 A1 | 12/2013 |
| WO | 2014058025 A1 | 4/2014 |
| WO | 2015053523 A1 | 4/2015 |
| WO | 2018065401 A1 | 4/2018 |
| WO | 2018065403 A1 | 4/2018 |

OTHER PUBLICATIONS

Ong, Seow Theng et al., "Hybrid cytomegalovirus enhancer-h1 promoter-based plasmid and baculovirus vectors mediate effective RNA interference," Hum. Gene Ther. 16(12):1404-12 (2005); doi: 10.1089/hum.2005.16.1404. (as cited by JPO).

Su, Jianguo et al., "Hybrid cytomegalovirus-U6 promoter-based plasmid vectors improve efficiency of RNA interference in zebrafish," Mar. Biotechnol. (NY) 10(5):511-7 (2008); doi: 10.1007/s10126-008-9087-8. Epub Mar. 6, 2008 (as cited by JPO).

Wang, C. Y. et al., "Improved neuronal transgene expression from an AAV-2 vector with a hybrid CMV enhancer/PDGF-beta promoter," J Gene Med.7(7):945-55 (2005) (as cited by JPO). doi: 10.1002/jgm.742.

JPO Office Action drafted Dec. 1, 2020, in connection with JP2018-536777, national phase corresponding to PCT/US2017/015130. (In original Japanese, with full English translation).

Spiess, C. et al., Alternative molecular formats and therapeutic applications for bispecific antibodies, Molecular Immunology 67 (2015) p. 95-100.

Kim, S-Y. et al., "The human elongation factor 1 alpha (EF-1α) first intron highly enhances expression of foreign genes from the murine cytomegalovirus promoter," Journal of Biotechnology 93 (2002), p. 183-187.

Schek, N. et al., "Definition of the Upstream Efficiency Element of the Simian Virus 40 Late Polyadenylation Signal by Using In Vitro Analyses," Molecular and Cellular Biology, Dec. 1992, p. 5386-5393.

Patwardhan, R. P. et al., "High-resoultion analysis of DNA regulatory elements by synthetic saturation mutagenesis," Nat. Biotechnol. Dec. 2009; 27(12): p. 1173-1175. doi:10.1038/nbt.1589.

Orlova, N. A. et al., "Improved elongation factor-1 alpha-based vectors for stable high-level expression of heterologous proteins in Chinese hamster ovary cells," BMC Biotechnology 2014, 14:56, http://biomedcentral.com/1472-6750/14/56.

Mizushima, S. et al., "pEF-BOS, a powerful mammalian expression vector," Nucleic Acids Research, vol. 18, No. 17, p. 5322, Jun. 19, 1990, Oxford University Press.

Mignone, F. et al., "Untranslated regions of mRNAs," Genome Biology 2002, Feb. 28, 2002, http://genomebiology.com/2002/3/3/reviews/0004.1.

Lacy-Hulbert, A., et al., "Interruption of coding sequences by hetrologous introns can enhance the functional expression of recombinant genes," Gene Therapy (2001) 8, p. 649-653, Nature Publishing Group.

European Patent Office, "International Search Report," dated Mar. 15, 2017, p. 1-5.

Brinster, R. L. et al., "Introns increase transcriptional efficiency in transgenic mice," Pro. Natl. Acad. Sci. USA, vol. 85, pp. 836-840, Feb. 1988, Developmental Biology.

Wurm, F. M., "CHO *Quasi*species—Implications for Manufacturing Processes," Processes 2013, 1, p. 296-311, www.mdpi.com/journal/processes.

Kobayashi, M. et al., "The CMV Enhancer Stimulates Expression of Foreign Genes from the Human EF-1α Promoter," Analytical Biochemistry 247, p. 179-181 (1997), Academic Press.

Yao, F. et al., "Tetracycline repressor, tetR, rather than the tetR-mammalian cell transcription factor fusion derivatives, regulates inducible gene expression in mammalian cells," Hum Gene Ther., Sep. 1, 1998;9(13): p. 1939-50.

Ong, S. T. et al., "Hybrid Cytomegalovirus Enchancer-H1 Promoter-Based Plasmid and Baculovirus Vectors Medicate Effective RNA Interference," Human Gene Therapy, vol. 16, No. 12, Dec. 1, 2005 (Dec. 1, 2005), p. 1404-1412.

Su, J. et al., "Hybrid Cytomegalovirus-U6 Promoter-based Plasmid Vectors Improve Efficiency of RNA Interference in Zebrafish," Marine Biotechnology, Springer-Verlag, NE, vol. 10, No. 5, Mar. 6, 2008 (Mar. 6, 2008), p. 511-517.

Wang, C. Y. et al., "Improved neuronal tansgene expression from an AAV-2, vector with a hybrid CMV enhancer/PDGF- .beta. promoter," Journal of Gene Medicine, John Wiley & Sons, Inc., US, vol. 7, No. 7, Jul. 1, 2005 (Jul. 1, 2005), p. 945-955.

Wakabayashi-Ito, N. et al., "Characterization of the Regulatory Elements in the Promoter of the Human Elongation Factor-1alpha Gene*," The Journal of Biological Chemistry, vol. 269, No. 47, Issue of Nov. 25, pp. 29831-29837, 1994, USA.

Jeang, Kuan-Teh, et al., "Multiple Tandemly Repeated Binding Sites for Cellular Nuclear Factor 1 That Surround the Major Immediate-Early Promoters of Simian and Human Cytomegalovirus," Journal of Virology, May 1987, p. 1559-1570, vol. 61, No. 5.

Bentley, William E., et al., "Plasmid-Encoded Protein: The Principal Factor in the 'Metabolic Burden' Associated with Recombinant Bacteria," Biotechnology and Bioengineering, vol. 102, No. 5, Apr. 1, 2009, p. 1283-1297.

Kanduri, C., et al., "The 5' flank of mouse H19 in an unusual chromatin conformation unidirectionally blocks enhancer-promoter communication," Research Paper, Current Biology 2000, 10:449-457.

Kempken, R., et al., "Significance of Specific Productivity for the Effectiveness and Consistency of Mammalian Cell Cultivation," E.C. Beuvery et al. (eds.), Animal Cell Technology: Developments towards the 21st Century, p. 561-565, 1995 Kluwer Academic Publishers.

Meleady, Paula, et al., "Sustained productivity in recombinant Chinese Hamster Ovary (CHO) cell lines; proteome analysis of the molecular basis for a process-related phenotype," BMC Biotechnology 2011, 11:78, http://www.biomedcentral.com/1472-6750/11/78, p. 1-11.

Misaghi, Shahram, et al., "It's Time to Regulate: Coping With Product-Induced Nongenetic Clonal Instability in CHO Cell Lines via Regulated Protein Expression," American Institute of Chemical Engineers, 2014, Biotechnol. Prog. 30:1432-1440.

(56) References Cited

OTHER PUBLICATIONS

Qin, Jana Yuxia, et al., "Systematic Comparison of Constitutive Promoters and the Doxycycline-Inducible Promoter," PLOS ONE, Published May 12, 2010, https://dol.org/10.1371/journal pone. 0010611, p. 1/5.

Recillas-Targa, Felix, et al., "Position-effect protection and enhancer blocking by the chicken β-globin insulator are separable activities," PNAS, May 14, 2002, vol. 99, No. 10, 6883-6888.

Rosano, German L., et al., "Recombinant protein expression in *Escherichia coli*: advances and challenges," Frontiers in Microbiology, Apr. 2014, vol. 5, Article 172, pp. 1-17, www.frontiersin.org; doi: 10.3389/fmicb.2014.00172.

Watanabe, Satoshi, et al., "Functional analysis of the sea urchin-derived arylsulfatase (Ars)-element in mammalian cells," Genes to Cells (2006) 11, 1009-1021, Molecular Biology Society of Japan/Blackwell Publishing Ltd.

European Patent Office, "International Search Report and Written Opinion," in PCT/US2017/015130, dated Apr. 5, 2017.

WIPO, "International Preliminary Report on Patentability," in PCT/US2017/015130, dated Aug. 9, 2018.

European Patent Office, Communication Pursuant to Rules 161(1) and 162 EPC, in EP1770520.6 (national stage of PCT/US2017/015130), dated Sep. 7, 2018.

Valenzuela, Lourdes & Kamakaka, Rohinton T., "Chromatin Insulators," Annu. Rev. Genet. 2006. 40:107-138.

Addison, C.L. et al., "Comparison of the human versus murine cytomegalovirus immediate early gene promoters for transgene expression by adenoviral vectors," Journal of General Virology (1997), 78, 1653-1661.

\* cited by examiner

FIG. 12

```
pJV57  TATATAAGCAGAGCTCTCCCTATCAGTGATAGAGATCTCCCTATCAGTGATAGAGA
       ||||||||||||||||||||||||||||||      ||||||||||||||||||||
pJV60  TATATAAGCAGAGCTCTCCCTATCAGTGATCAGTTCCTCCCTATCAGTGATAGAGA
```

FIG. 13

```
pJV56  TATAAGAGGCGCGACCAGCGTCGGT-ACCGTA------------------CCTCT
       |||||  | ||  |||||||||||||  |||||                  |||||
pJV59  TATAT-AAGCAGAGCTCGTTTAGTGAACCGTCAGTTCGTCTCTAGACGCCAACCGCCTCT
```

FIG. 21A
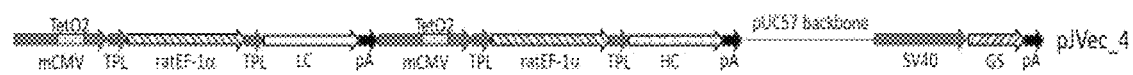
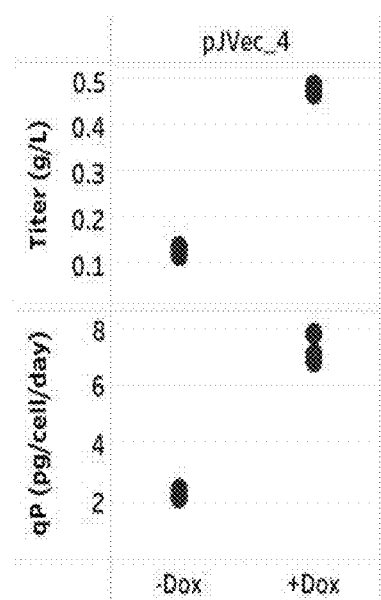
FIG. 21B
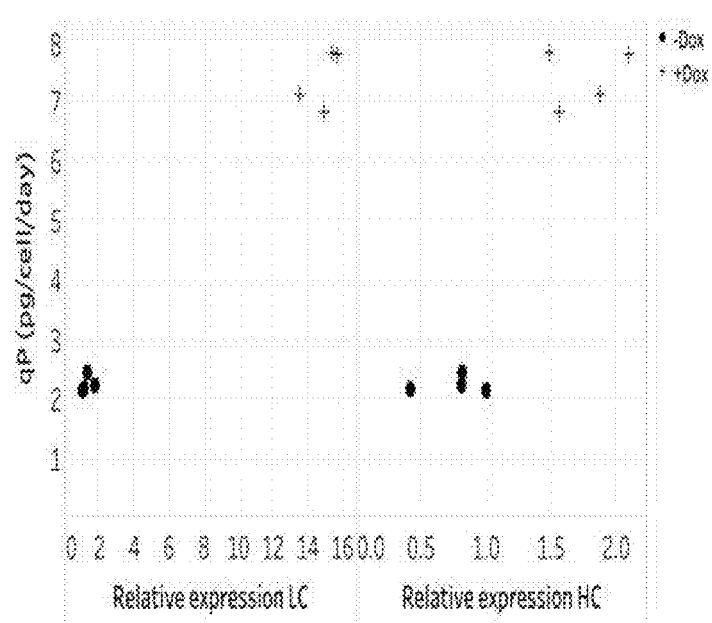
FIG. 21C

FIG. 22A
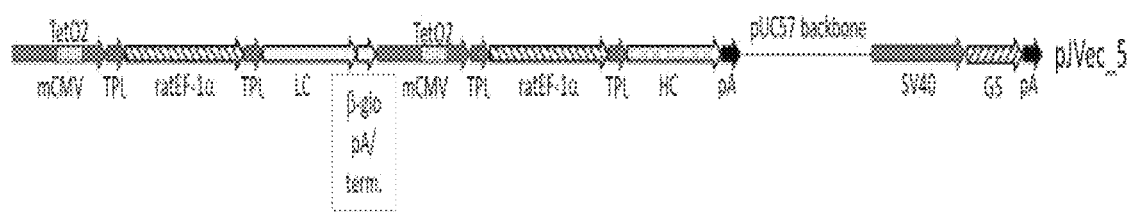
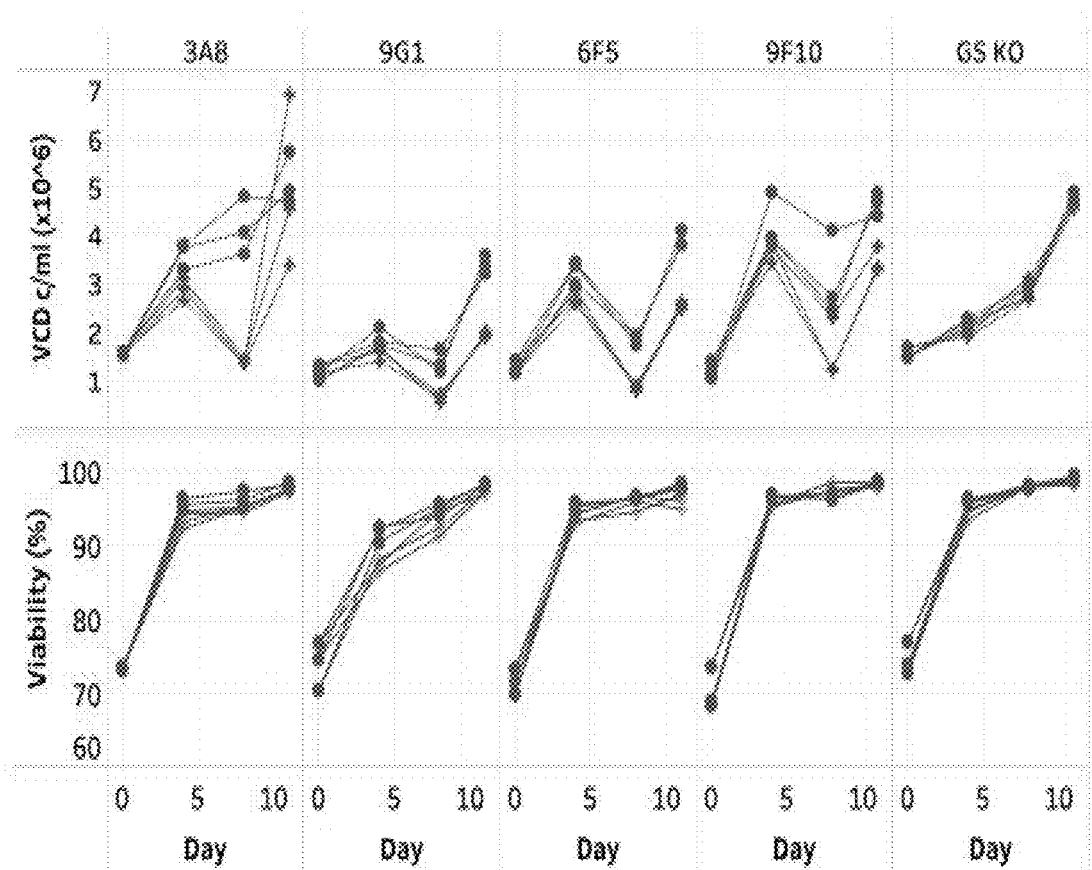
FIG. 22B

SEQUENCE LISTING

```
<160> NUMBER OF SEQ ID NOS: 53

<210> SEQ ID NO 1
<211> LENGTH: 1717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gtcaacagga aagttccatt ggagccaagt acattgagtc aatagggact ttccaatggg     60
ttttgcccag tacataaggt caatgggagg taagccaatg ggtttttccc attactggca    120
cgtatactga gtcattaggg actttccaat gggttttgcc cagtacataa ggtcaatagg    180
ggtgaatcaa caggaaagtc ccattggagc caagtacact gagtcaatag ggactttcca    240
ttgggttttg cccagtacaa aaggtcaata gggggtgagt caatgggttt ttcccattat    300
tggcacgtac ataaggtcaa tagggggtgag tcattgggtt tttccagcca atttaattaa    360
aacgccatgt actttcccac cattgacgtc aatgggctat tgaaactaat gcaacgtgac    420
ctttaaacgg tactttccca tagctgatta atgggaaagt accgttctcg agccaataca    480
cgtcaatggg aagtgaaagg gcagccaaaa cgtaacaccg ccccggtttt cccctggaaa    540
ttccatattg gcacgcattc tattggctga gctgcgttct acgtgggtat aagaggcgcg    600
accagcgtcg gtaccgtacc tcttccgcat cgctgtctgc gagggccagc tgttggggtg    660
```

```
agtggcgggt gtggcttccg cgggccccgg agctggagcc ctgctctgag cgggccgggc    720
tgatatgcga gtgtcgtccg cagggtttag ctgtgagcat tcccacttcg agtggcgggc    780
ggtgcggggg tgagagtgcg aggcctagcg gcaacccgt agcctcgcct cgtgtccggc     840
ttgaggccta gcgtggtgtc cgccgccgcg tgccactccg gccgcactat gcgtttttttg    900 tccttgctgc cctcgattgc cttccagcag catgggctaa caaagggagg gtgtggggct    960
cactcttaag gagcccatga agcttacgtt ggataggaat ggaagggcag gaggggcgac    1020
tggggcccgc ccgccttcgg agcacatgtc cgacgccacc tggatggggc gaggcctgtg    1080
gctttccgaa gcaatcgggc gtgagtttag cctacctggg ccatgtggcc ctagcactgg    1140
gcacggtctg gcctggcggt gccgcgttcc cttgcctccc aacaagggtg aggccgtccc    1200
gcccggcacc agttgcttgc gcggaaagat ggccgctccc ggggcccgt tgcaaggagc     1260 tcaaaatgga ggacgcggca gcccggtgga gcgggcgggt gagtcaccca cacaaaggaa    1320
gagggccttg cccctcgccg gccgctgctt cctgtgaccc cgtggtctat cggccgcata    1380
gtcacctcgg gcttctcttg agcaccgctc gtcgcggcgg ggggagggga tctaatggcg    1440
ttggagtttg ttcacatttg gtgggtggag actagtcagg ccagcctggc gctggaagtc    1500
attcttggaa tttgccccctt tgagtttgga gcgaggctaa ttctcaagcc tcttagcggt    1560
tcaaaggtat tttctaaacc cgtttccagc tcgcggttga ggacaaactc ttcgcggtct    1620
ttccagtact cttggatcgg aaacccgtcg gcctccgaac ggtactccgc caccgaggga    1680
cctgagcgag tccgcatcga ccggatcgga aaacctc                             1717

<210> SEQ ID NO 2
<211> LENGTH: 616
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gtcaacagga aagttccatt ggagccaagt acattgagtc aatagggact ttccaatggg      60
ttttgcccag tacataaggt caatgggagg taagccaatg ggttttttccc attactggca    120 cgtatactga gtcattaggg actttccaat gggttttgcc cagtacataa ggtcaatagg     180
ggtgaatcaa caggaaagtc ccattggagc caagtacact gagtcaatag ggactttcca    240 tgggttttg cccagtacaa aaggtcaata gggggtgagt caatgggttt ttcccattat     300
tggcacgtac ataaggtcaa tagggtgag tcattgggtt tttccagcca atttaattaa     360
aacgccatgt actttcccac cattgacgtc aatgggctat tgaaactaat gcaacgtgac    420
ctttaaacgg tactttccca tagctgatta atgggaaagt accgttctcg agccaataca    480
cgtcaatggg aagtgaaagg gcagccaaaa cgtaacaccg cccggttttt cccctggaaa    540
ttccatattg gcacgcattc tattggctga gctgcgttct acgtgggtat aagaggcgcg    600
accagcgtcg gtaccg                                                    616

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 3
tacctcttcc gcatcgctgt ctgcgagggc cagctgttgg g                          41

<210> SEQ ID NO 4
<211> LENGTH: 932
<212> TYPE: DNA
<213> ORGANISM: Rattus norvegicus

<400> SEQUENCE: 4
gtgagtggcg ggtgtggctt ccgcgggccc cggagctgga gccctgctct gagcgggccg      60
ggctgatatg cgagtgtcgt ccgcagggtt tagctgtgag cattcccact tcgagtggcg     120
ggcggtgcgg gggtgagagt gcgaggccta gcggcaaccc cgtagcctcg cctcgtgtcc     180
ggcttgaggc ctagcgtggt gtccgccgcc gcgtgccact ccggccgcac tatgcgtttt     240
ttgtccttgc tgccctcgat tgccttccag cagcatgggc taacaaaggg agggtgtggg     300
gctcactctt aaggagccca tgaagcttac gttggatagg aatggaaggg caggaggggc     360
gactggggcc cgcccgcctt cggagcacat gtccgacgcc acctggatgg ggcgaggcct     420
gtggctttcc gaagcaatcg ggcgtgagtt tagcctacct gggccatgtg gccctagcac     480
tgggcacggt ctggcctggc ggtgccgcgt tcccttgcct cccaacaagg gtgaggccgt     540
cccgcccggc accagttgct tgcgcggaaa gatggccgct cccggggccc tgttgcaagg     600
agctcaaaat ggaggacgcg gcagcccggt ggagcgggcg ggtgagtcac ccacacaaag     660
gaagagggcc ttgcccctcg ccggccgctg cttcctgtga ccccgtggtc tatcggccgc     720
atagtcacct cgggcttctc ttgagcaccg ctcgtcgcgg cggggggagg ggatctaatg     780
gcgttggagt ttgttcacat ttggtgggtg gagactagtc aggccagcct ggcgctggaa     840
gtcattcttg gaatttgccc ctttgagttt ggagcgaggc taattctcaa gcctcttagc     900
ggttcaaagg tattttctaa acccgtttcc ag                                   932

<210> SEQ ID NO 5
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ctcgcggttg aggacaaaact cttcgcggtc tttccagtac tcttggatcg gaaacccgtc     60
ggcctccgaa cggtactccg ccaccgaggg acctgagcga gtccgcatcg accggatcgg    120
aaaacctc                                                              128

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaaacacga ttgctcgaga gttgccaccc atcatg                                36

<210> SEQ ID NO 7
<211> LENGTH: 66
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
atggacatga gggtgcccgc tcagctcctg gggctcctgc tgctgtggct gagaggtgcg    60
cgctgt                                                               66

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 9
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tatataagca gagctctccc tatcagtgat agagatctcc ctatcagtga tagagatcgt    60
cgacgagct                                                            69

<210> SEQ ID NO 10
<211> LENGTH: 9
<212> TYPE: DNA
<213> ORGANISM: Mus sp.

<400> SEQUENCE: 10 cagcgtcgg                                                             9

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggcgccgcca cc                                                        12

<210> SEQ ID NO 12
<211> LENGTH: 3171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggggggtt ctcatcatca tcatcatcat ggtatggcta gcatgactgg tggacagcaa    60
atgggtcggg atctgtacga cgatgacgat aaggtaccta aggatcagct tggagttgat   120
```

```
cccgtcgttt tacaacgtcg tgactgggaa aaccctggcg ttacccaact taatcgcctt    180
gcagcacatc ccccttttcgc cagctggcgt aatagcgaag aggcccgcac cgatcgccct   240
tcccaacagt tgcgcagcct gaatggcgaa tggcgctttg cctggtttcc ggcaccagaa    300
gcggtgccgg aaagctggct ggagtgcgat cttcctgagg ccgatactgt cgtcgtcccc    360
tcaaactggc agatgcacgg ttacgatgcg cccatctaca ccaacgtaac ctatcccatt    420
acggtcaatc cgccgtttgt tcccacggag aatccgacgg ttgttactc gctcacattt     480
aatgttgatg aaagctggct acaggaaggc cagacgcgaa ttattttga tggcgttaac     540
tcggcgtttc atctgtggtg caacgggcgc tgggtcggtt acggccagga cagtcgtttg    600
ccgtctgaat ttgacctgag cgcattttta cgcgccggag aaaaccgcct cgcggtgatg    660
gtgctgcgtt ggagtgacgg cagttatctg gaagatcagg atatgtggcg gatgagcggc    720
attttccgtg acgtctcgtt gctgcataaa ccgactacac aaatcagcga tttccatgtt    780
gccactcgct ttaatgatga tttcagccgc gctgtactgg aggctgaagt tcagatgtgc    840
ggcgagttgc gtgactacct acgggtaaca gtttctttat ggcagggtga aacgcaggtc    900
gccagcggca ccgcgccttt cggcggtgaa attatcgatg agcgtggtgg ttatgccgat    960
cgcgtcacac tacgtctgaa cgtcgaaaac ccgaaactgt ggagcgccga atcccgaat    1020
ctctatcgtg cggtggttga actgcacacc gccgacggca cgctgattga agcagaagcc   1080
tgcgatgtcg gtttccgcga ggtgcggatt gaaaatggtc tgctgctgct gaacggcaag   1140
ccgttgctga ttcgaggcgt taaccgtcac gagcatcatc ctctgcatgg tcaggtcatg   1200
gatgagcaga cgatggtgca ggatatcctg ctgatgaagc agaacaactt taacgccgtg   1260
cgctgttcgc attatccgaa ccatccgctg tggtacacgc tgtgcgaccg ctacggcctg   1320
tatgtggtgg atgaagccaa tattgaaacc cacggcatgg tgccaatgaa tcgtctgacc   1380
gatgatccgc gctggctacc ggcgatgagc gaacgcgtaa cgcgaatggt gcagcgcgat   1440
cgtaatcacc cgagtgtgat catctggtcg ctggggaatg aatcaggcca cggcgctaat   1500
cacgacgcgc tgtatcgctg gatcaaatct gtcgatcctt cccgcccggt gcagtatgaa   1560
ggcggcggag ccgacaccac ggccaccgat attatttgcc cgatgtacgc gcgcgtggat   1620
gaagaccagc ccttcccggc tgtgccgaaa tggtccatca aaaaatggct ttcgctacct   1680
ggagagacgc gcccgctgat cctttgcgaa tacgcccacg cgatgggtaa cagtcttggc   1740
ggtttcgcta aatactggca ggcgtttcgt cagtatcccc gtttacaggg cggcttcgtc   1800
tgggactggg tggatcagtc gctgattaaa tatgatgaaa cggcaaccc gtggtcggct    1860
tacggcggtg attttggcga tacgccgaac gatcgccagt tctgtatgaa cggtctggtc   1920
tttgccgacc gcacgccgca tccagcgctg acgaagcaa acaccagca gcagtttttc     1980
cagttccgtt tatccgggca aaccatcgaa gtgaccagcg aatacctgtt ccgtcatagc   2040
gataacgagc tcctgcactg gatggtggcg ctggatggta agccgctggc aagcggtgaa   2100
gtgcctctgg atgtcgctcc acaaggtaaa cagttgattg aactgcctga actaccgcag   2160
ccggagagcg ccgggcaact ctggctcaca gtacgcgtag tgcaaccgaa cgcgaccgca   2220
tggtcagaag ccgggcacat cagcgcctgg cagcagtggc gtctggcgga aaacctcagt   2280
gtgacgctcc ccgccgcgtc ccacgccatc ccgcatctga ccaccagcga atggatttt    2340
tgcatcgagc tgggtaataa gcgttggcaa tttaaccgcc agtcaggctt tctttcacag   2400
atgtggattg gcgataaaaa acaactgctg acgccgctgc gcgatcagtt cacccgtgca   2460
```

-continued

| | |
|---|---|
| ccgctggata acgacattgg cgtaagtgaa gcgacccgca ttgaccctaa cgcctgggtc | 2520 |
| gaacgctgga aggcggcggg ccattaccag gccgaagcag cgttgttgca gtgcacggca | 2580 |
| gatacacttg ctgatgcggt gctgattacg accgctcacg cgtggcagca tcaggggaaa | 2640 |
| accttattta tcagccggaa aacctaccgg attgatggta gtggtcaaat ggcgattacc | 2700 |
| gttgatgttg aagtggcgag cgatacaccg catccggcgc ggattggcct gaactgccag | 2760 |
| ctggcgcagg tagcagagcg ggtaaactgg ctcggattag ggccgcaaga aaactatccc | 2820 |
| gaccgcctta ctgccgcctg ttttgaccgc tgggatctgc cattgtcaga catgtatacc | 2880 |
| ccgtacgtct tcccgagcga aaacggtctg cgctgcggga cgcgcgaatt gaattatggc | 2940 |
| ccacaccagt ggcgcggcga cttccagttc aacatcagcc gctacagtca acagcaactg | 3000 |
| atggaaacca gccatcgcca tctgctgcac gcggaagaag gcacatggct gaatatcgac | 3060 |
| ggtttccata tggggattgg tggcgacgac tcctggagcc cgtcagtatc ggcggagttc | 3120 |
| cagctgagcg ccggtcgcta ccattaccag ttggtctggt gtcaaaaata a | 3171 |

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcggccgcgc tagc                                                         14

<210> SEQ ID NO 14
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| cacacatcat aagatacatt gatgagtttg gacaaaccac aactagaatg cagtgaaaaa | 60 |
| aatgctttat ttgtgaaatt tgtgatgcta ttgctttatt tgtaaccatt ataagctgca | 120 |
| ataaacaagt taacaacaac aattgcattc attttatgtt tcaggttcag ggggagatgt | 180 |
| gggaggtttt ttaaagcaag taaaacctct acaaatgtgg ta | 222 |

<210> SEQ ID NO 15
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | |
|---|---|
| gttctacgtg ggtatataag cagagctctc cctatcagtg atagagatct ccctatcagt | 60 |
| gatagagatc gtcgacgagc tcagcgtcgg taccgtacct ct | 102 |

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttctacgtg ggtataagag gcgcgaccag cgtcggtacc gtacctct                48

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tatataagca gagctctccc tatcagtgat agagatctcc ctatcagtga tagaga        56

<210> SEQ ID NO 18
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tatataagca gagctctccc tatcagtgat cagttcctcc ctatcagtga tagaga        56

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tataagaggc gcgaccagcg tcggtaccgt acctct                             36

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tatataagca gagctcgttt agtgaaccgt cagttcgtct ctagacgcca accgcctct     59

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tataagaggc gcgaccagcg tcggtaccg                                     29

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tatataagca gagcagcgtc ggtaccg                    27

<210> SEQ ID NO 23
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctctccctat cagtgataga gatctcccta tcagtgatag agatcgtcga cgagct       56

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tatataagca gagct                                 15

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagcgtcggt accg                                  14

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tataagaggc gcgac                                 15

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gttctacgtg gg                                    12

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
tataagaggc gcgaccagcg tcggtaccg                                    29
```

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
tccctatcag tgatagagat ctccctatca gtgatagaga                        40
```

<210> SEQ ID NO 30
<211> LENGTH: 1771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
gtcaacagga aagttccatt ggagccaagt acattgagtc aatagggact ttccaatggg    60
ttttgcccag tacataaggt caatgggagg taagccaatg ggttttcccc attactggca   120
cgtatactga gtcattaggg actttccaat gggttttgcc cagtacataa ggtcaatagg   180
ggtgaatcaa caggaaagtc ccattggagc caagtacact gagtcaatag gactttcca    240 ttgggttttg cccagtacaa aaggtcaata ggggtgagt caatgggttt ttcccattat    300
tggcacgtac ataaggtcaa tagggtgag tcattgggtt tttccagcca atttaattaa   360
aacgccatgt actttcccac cattgacgtc aatgggctat tgaaactaat gcaacgtgac   420 cttaaacgg tactttccca tagctgatta atgggaaagt accgttctcg agccaataca   480
cgtcaatggg aagtgaaagg gcagccaaaa cgtaacaccg ccccggtttt cccctggaaa   540
ttccatattg gcacgcattc tattggctga gctgcgttct acgtgggtat ataagcagag   600
ctctccctat cagtgataga gatctcccta tcagtgatag agatcgtcga cgagctcagc   660
gtcggtaccg tacctcttcc gcatcgctgt ctgcgagggc cagctgttgg ggtgagtggc   720
gggtgtggct tccgcgggcc ccggagctgg agccctgctc tgagcgggcc gggctgatat   780
gcgagtgtcg tccgcagggt ttagctgtga gcattcccac ttcgagtggc gggcggtgcg   840
ggggtgagag tgcgaggcct agcggcaacc ccgtagcctc gcctcgtgtc cggcttgagg   900
cctagcgtgg tgtccgccgc gcgtgccac tccggccgca ctatgcgttt tttgtccttg   960
ctgccctcga ttgccttcca gcagcatggg ctaacaaagg gagggtgtgg ggctcactct  1020
taaggagccc atgaagctta cgttggatag gaatggaagg gcaggagggg cgactggggc  1080
ccgcccgcct tcggagcaca tgtccgacgc cacctggatg gggcgaggcc tgtggctttc  1140
cgaagcaatc gggcgtgagt ttagcctacc tgggccatgt ggccctagca ctgggcacgg  1200
tctggcctgg cggtgccgcg ttcccttgcc tcccaacaag ggtgaggccg tcccgcccgg  1260
caccagttgc ttgcgcggaa agatggccgc tcccgggggcc ctgttgcaag gagctcaaaa  1320
tggaggacgc ggcagcccgg tggagcgggc gggtgagtca cccacacaaa ggaagagggc  1380
cttgcccctc gccggccgct gcttcctgtg accccgtggt ctatcggccg catagtcacc  1440
tcgggcttct cttgagcacc gctcgtcgcg cgggggggag gggatctaat ggcgttggag  1500
tttgttcaca tttggtgggt ggagactagt caggccagcc tggcgctgga agtcattctt  1560
```

| | |
|---|---|
| ggaatttgcc cctttgagtt tggagcgagg ctaattctca agcctcttag cggttcaaag | 1620 |
| gtattttcta aacccgtttc cagctcgcgg ttgaggacaa actcttcgcg gtctttccag | 1680 |
| tactcttgga tcggaaaccc gtcggcctcc gaacggtact ccgccaccga gggacctgag | 1740 |
| cgagtccgca tcgaccggat cggaaaacct c | 1771 |

<210> SEQ ID NO 31
<211> LENGTH: 1740
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

| | |
|---|---|
| gtcaacagga aagttccatt ggagccaagt acattgagtc aatagggact ttccaatggg | 60 |
| ttttgcccag tacataaggt caatgggagg taagccaatg ggttttttccc attactggca | 120 |
| cgtatactga gtcattaggg actttccaat gggttttgcc cagtacataa ggtcaatagg | 180 |
| ggtgaatcaa caggaaagtc ccattggagc caagtacact gagtcaatag gactttccca | 240 |
| ttgggttttg cccagtacaa aaggtcaata ggggtgagt caatgggttt ttcccattat | 300 |
| tggcacgtac ataaggtcaa taggggtgag tcattgggtt tttccagcca atttaattaa | 360 |
| aacgccatgt actttcccac cattgacgtc aatgggctat tgaaactaat gcaacgtgac | 420 |
| ctttaaacgg tactttccca tagctgatta atgggaaagt accgttctcg agccaataca | 480 |
| cgtcaatggg aagtgaaagg gcagccaaaa cgtaacaccg ccccggtttt ccctggaaa | 540 |
| ttccatattg gcacgcattc tattggctga gctgcgttct acgtgggtat ataagcagag | 600 |
| ctcgtttagt gaaccgtcag ttcgtctcta gacgccaacc gcctcttccg catcgctgtc | 660 |
| tgcgagggcc agctgttggg gtgagtggcg ggtgtggctt ccgcgggccc cggagctgga | 720 |
| gccctgctct gagcgggccg ggctgatatg cgagtgtcgt ccgcagggtt tagctgtgag | 780 |
| cattcccact tcgagtggcg ggcggtgcgg gggtgagagt gcgaggccta gcggcaaccc | 840 |
| cgtagcctcg cctcgtgtcc ggcttgaggc ctagcgtggt gtccgccgcc gcgtgccact | 900 |
| ccggccgcac tatgcgtttt ttgtccttgc tgccctcgat tgccttccag cagcatgggc | 960 |
| taacaaaggg agggtgtggg gctcactctt aaggagccca tgaagcttac gttggatagg | 1020 |
| aatgaaggg caggaggggc gactgggcc cgcccgcctt cggagcacat gtccgacgcc | 1080 |
| acctggatgg ggcgaggcct gtggcttttcc gaagcaatcg ggcgtgagtt tagcctacct | 1140 |
| gggccatgtg gccctagcac tgggcacggt ctggcctggc ggtgccgcgt tcccttgcct | 1200 |
| cccaacaagg gtgaggccgt cccgcccggc accagttgct tgcgcggaaa gatggccgct | 1260 |
| cccgggccc tgttgcaagg agctcaaaat ggaggacgcg gcagcccggt ggagcgggcg | 1320 |
| ggtgagtcac ccacacaaag gaagagggcc ttgccccctcg ccggccgctg cttcctgtga | 1380 |
| ccccgtggtc tatcgccgc atagtcacct cgggcttctc ttgagcaccg ctcgtcgcgg | 1440 |
| cggggggagg ggatctaatg gcgttggagt ttgttcacat ttggtgggtg gagactagtc | 1500 |
| aggccagcct ggcgctggaa gtcattcttg gaatttgccc ctttgagttt ggagcgaggc | 1560 |
| taattctcaa gcctcttagc ggttcaaagg tattttctaa acccgtttcc agctcgcggt | 1620 |
| tgaggacaaa ctcttcgcgg tctttccagt actcttggat cggaaacccg tcggcctccg | 1680 |
| aacggtactc cgccaccgag ggacctgagc gagtccgcat cgaccggatc ggaaaacctc | 1740 |

<210> SEQ ID NO 32

<211> LENGTH: 1771
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
gtcaacagga aagttccatt ggagccaagt acattgagtc aatagggact ttccaatggg      60
ttttgcccag tacataaggt caatgggagg taagccaatg ggttttccc attactggca      120
cgtatactga gtcattaggg actttccaat gggttttgcc cagtacataa ggtcaatagg     180
ggtgaatcaa caggaaagtc ccattggagc caagtacact gagtcaatag ggactttcca     240
ttgggttttg cccagtacaa aggtcaata ggggtgagt caatgggttt tcccattat       300
tggcacgtac ataaggtcaa tagggtgag tcattgggtt tttccagcca atttaattaa     360
aacgccatgt actttcccac cattgacgtc aatgggctat gaaactaat gcaacgtgac     420
ctttaaacgg tactttccca tagctgatta atgggaaagt accgttctcg agccaataca     480
cgtcaatggg aagtgaaagg gcagccaaaa cgtaacaccg ccccggtttt ccctggaaa     540
ttccatattg gcacgcattc tattggctga gctgcgttct acgtgggtat ataagcagag     600
ctctccctat cagtgatcag ttcctcccta tcagtgatag agatcgtcga cgagctcagc    660
gtcggtaccg tacctcttcc gcatcgctgt ctgcgagggc cagctgttgg ggtgagtggc    720
gggtgtggct tccgcgggcc ccggagctgg agccctgctc tgagcgggcc gggctgatat    780
gcgagtgtcg tccgcagggt ttagctgtga gcattccac ttcgagtggc gggcggtgcg    840
ggggtgagag tgcgaggcct agcggcaacc ccgtagcctc gcctcgtgtc cggcttgagg    900
cctagcgtgg tgtccgccgc gcgtgccac tccggccgca ctatgcgttt tttgtccttg    960
ctgccctcga ttgccttcca gcagcatggg ctaacaaagg gagggtgtgg ggctcactct   1020
taaggagccc atgaagctta cgttggatag aatggaagg gcaggagggg cgactggggc    1080
ccgcccgcct tcggagcaca tgtccgacgc cacctggatg gggcgaggcc tgtggctttc   1140
cgaagcaatc gggcgtgagt ttagcctacc tgggccatgt ggccctagca ctgggcacgg   1200
tctggcctgg cggtgccgcg ttcccttgcc tcccaacaag ggtgaggccg tcccgcccgg   1260
caccagttgc ttgcgcggaa agatggccgc tcccggggcc ctgttgcaag gagctcaaaa   1320
tggaggacgc ggcagcccgg tggagcgggc gggtgagtca cccacacaaa ggaagagggc   1380
cttgcccctc gccggccgct gcttcctgtg acccgtggt ctatcggccg catagtcacc    1440
tcgggcttct cttgagcacc gctcgtcgcg gcggggggag gggatctaat ggcgttggag   1500
tttgttcaca tttggtgggt ggagactagt caggccagcc tggcgctgga agtcattctt   1560
ggaatttgcc cctttgagtt tggagcgagg ctaattctca agcctcttag cggttcaaag   1620
gtatttccta aacccgtttc cagctcgcgg ttgaggacaa actcttcgcg gtctttccag   1680
tactcttgga tcggaaaccc gtcggcctcc gaacggtact ccgccaccga gggacctgag   1740
cgagtccgca tcgaccggat cggaaaacct c                                  1771
```

<210> SEQ ID NO 33
<211> LENGTH: 641
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
gtcaacagga aagttccatt ggagccaagt acattgagtc aatagggact ttccaatggg      60
ttttgcccag tacataaggt caatgggagg taagccaatg ggttttccc attactggca      120 cgtatactga gtcattaggg actttccaat gggttttgcc cagtacataa ggtcaatagg      180
ggtgaatcaa caggaaagtc ccattggagc caagtacact gagtcaatag gactttcca      240 ttgggttttg cccagtacaa aaggtcaata ggggtgagt caatgggttt ttcccattat      300
tggcacgtac ataaggtcaa taggggtgag tcattgggtt tttccagcca atttaattaa      360
aacgccatgt actttcccac cattgacgtc aatgggctat tgaaactaat gcaacgtgac      420 cttttaaacgg tactttccca tagctgatta atgggaaagt accgttctcg agccaataca      480
cgtcaatggg aagtgaaagg gcagccaaaa cgtaacaccg ccccggtttt ccctggaaa      540 ttccatattg gcacgcattc tattggctga gctgcgttct acgtgggtat ataagcagag      600
ctcgtttagt gaaccgtcag ttcgtctcta gacgccaacc g                        641

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctccctatca gtgatcagtt cctccctatc agtgatagag a                         41

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tatataagca gagctcgttt agtgaaccgt cagttcgtct ctagacgcca accg           54

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cctggagaaa cctgccaagt atga                                            24

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agaaggtggt gaagcaggca tctgagggcc                                      30

<210> SEQ ID NO 38
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 38
actgttgaag tcgcaggaga caa                                             23

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cccagcacca tgaagatcaa                                                 20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cattgctcct cctgagcgca agta                                            24

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgcttgctga tccacatctc                                                 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gggaacagat gggcaccctt t                                               21

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttggccttcc aatggctttc ctgggc                                          26

<210> SEQ ID NO 44
<211> LENGTH: 25
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 44
acgatatccc tgccataggc tttgt                                          25

<210> SEQ ID NO 45
<211> LENGTH: 309
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
ccctagaaag atagtctgcg taaaattgac gcatgcattc ttgaaatatt gctctctctt    60
tctaaatagc gcgaatccgt cgctgtgcat ttaggacatc tcagtcgccg cttggagctc   120
ccgtgaggcg tgcttgtcaa tgcggtaagt gtcactgatt ttgaactata acgaccgcgt   180
gagtcaaaat gacgcatgat tatctttac gtgacttta agatttaact catacgataa    240
ttatattgtt atttcatgtt ctacttacgt gataacttat tatatatata ttttcttgtt   300
atagatatc                                                           309

<210> SEQ ID NO 46
<211> LENGTH: 154
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46
tcccgcccct aactccgccc agttccgccc attctccgcc ccatggctga ctaattttt    60 ttatttatgc agaggccgag gccgcctcgg cctctgagct attccagaag tagtgaggag   120
gcttttttgg aggcctaggc ttttgcaaaa agct                               154

<210> SEQ ID NO 47
<211> LENGTH: 239
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
gataaaagtt ttgttacttt atagaagaaa ttttgagttt ttgttttttt taataaataa   60
ataaacataa ataaattgtt tgttgaattt attattagta tgtaagtgta aatataataa   120
aacttaatat ctattcaaat taataaataa acctcgatat acagaccgat aaaacacatg   180
cgtcaatttt acacatgatt atctttaacg tacgtcacaa tatgattatc tttctaggg    239

<210> SEQ ID NO 48
<211> LENGTH: 1253
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
agctggttct ttccgcctca gaaggtacct aaccaagttc ctctttcaga ggttatttca   60

```
ggccaccttc caccatggcc acctcagcaa gttcccactt gaacaaaaac atcaagcaaa    120
tgtacttgtg cctgccccag ggtgagaaag tccaagccat gtatatctgg gttgatggta    180
ctggagaagg actgcgctgc aaaacccgca ccctggactg tgagcccaag tgtgtagaag    240
agttacctga gtggaatttt gatggctcta gtacctttca gtctgagggc tccaacagtg    300
acatgtatct cagccctgtt gccatgtttc ggacccctt ccgcagagat cccaacaagc    360
tggtgttctg tgaagttttc aagtacaacc ggaagcctgc agagaccaat ttaaggcact    420
cgtgtaaacg gataatggac atggtgagca accagcaccc ctggtttgga atggaacagg    480
agtatactct gatgggaaca gatgggcacc cttttggttg gccttccaat ggctttcctg    540
ggccccaagg tccgtattac tgtggtgtgg gcgcagacaa agcctatggc agggatatcg    600
tggaggctca ctaccgcgcc tgcttgtatg ctggggtcaa gattacagga acaaatgctg    660
aggtcatgcc tgcccagtgg gaatttcaaa taggaccctg tgaaggaatc cgcatgggag    720
atcatctctg ggtggcccgt ttcatcttgc atcgagtatg tgaagacttt ggggtaatag    780
caacctttga ccccaagccc attcctggga actggaatgg tgcaggctgc ataccaact    840 ttagcaccaa ggccatgcgg gaggagaatg gtctgaagca catcgaggag gccatcgaga    900
aactaagcaa gcggcaccgg taccacattc gagcctacga tcccaagggg ggcctggaca    960
atgcccgtcg tctgactggg ttccacgaaa cgtccaacat caacgacttt tctgctggtg    1020
tcgccaatcg cagtgccagc atccgcattc cccggactgt cggccaggag aagaaaggtt    1080
actttgaaga ccgccgcccc tctgccaatt gtgaccccct tgcagtgaca gaagccatcg    1140
tccgcacatg ccttctcaat gagactggcg acagcccctt ccaatacaaa aactaacgcc    1200
cgccccacga cccgcagcgc ccgaccgaaa ggagcgcacg accccatgca tcg    1253
```

<210> SEQ ID NO 49
<211> LENGTH: 1122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atggccacct cagcaagttc ccacttgaac aaaaacatca agcaaatgta cttgtgcctg     60
ccccagggtg agaaagtcca agccatgtat atctgggttg atggtactgg agaaggactg    120
cgctgcaaaa cccgcaccct ggactgtgag cccaagtgtg tagaagagtt acctgagtgg    180
aattttgatg gctctagtac ctttcagtct gagggctcca acagtgacat gtatctcagc    240
cctgttgcca tgtttcggga ccccttccgc agagatccca acaagctggt gttctgtgaa    300
gttttcaagt acaaccggaa gcctgcagag accaatttaa ggcactcgtg taaacggata    360
atggacatgg tgagcaacca gcaccctgg tttggaatgg aacaggagta tactctgatg    420
ggaacagatg ggcaccettt tggttggcct tccaatggct tcctgggcc caaggtccg     480 tattactgtg gtgtgggcgc agacaaagcc tatggcaggg atatcgtgga ggctcactac    540
cgcgcctgct tgtatgctgg ggtcaagatt acaggaacaa atgctgaggt catgcctgcc    600
cagtgggaat ttcaaatagg accctgtgaa ggaatccgca tgggagatca tctctgggtg    660
gcccgtttca tcttgcatcg agtatgtgaa gactttgggg taatagcaac ctttgacccc    720
aagcccattc tgggaactg gaatggtgca ggctgccata ccaactttag caccaaggcc    780
atgcgggagg agaatggtct gaagcacatc gaggaggcca tcgagaaact aagcaagcgg    840
```

```
caccggtacc acattcgagc ctacgatccc aagggggggcc tggacaatgc ccgtcgtctg        900
actgggttcc acgaaacgtc caacatcaac gactttctg ctggtgtcgc caatcgcagt         960
gccagcatcc gcattcccg gactgtcggc caggagaaga aaggttactt tgaagaccgc         1020 cgccctctg ccaattgtga cccctttgca gtgacagaag ccatcgtccg cacatgcctt         1080
ctcaatgaga ctggcgacga gcccttccaa tacaaaaact aa                          1122
```

<210> SEQ ID NO 50

<400> SEQUENCE: 50

000

<210> SEQ ID NO 51
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
cacacatcat aagatacatt gatgagtttg acaaaccac aactagaatg cagtgaaaaa         60
aatgctttat ttgtgaaatt tgtgatgcta ttgctttatt tgtaaccatt ataagctgca        120
ataaacaagt taacaacaac aattgcattc attttatgtt tcaggttcag ggggagatgt        180
gggaggtttt ttaaagcaag taaaacctct acaaatgtgg ta                          222
```

<210> SEQ ID NO 52
<211> LENGTH: 2750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
ggatccatgg ccggccatct gcagatcata tgatcggatg ccgggaccga cgagtgcaga        60
ggcgtgcaag cgagcttggc gtaatcatgg tcatagctgt ttcctgtgtg aaattgttat        120
ccgctcacaa ttccacacaa catacgagcc ggaagcataa agtgtaaagc ctggggtgcc        180
taatgagtga gctaactcac attaattgcg ttgcgctcac tgcccgcttt ccagtcggga        240
aacctgtcgt gccagctgca ttaatgaatc ggccaacgcg cggggagagg cggtttgcgt        300
attgggcgct cttccgcttc ctcgctcact gactcgctgc gctcggtcgt tcggctgcgg        360
cgagcggtat cagctcactc aaaggcggta atacggttat ccacagaatc agggggataac        420 gcaggaaaga acatgtgagc aaaaggccag caaaaggcca ggaaccgtaa aaaggccgcg        480
ttgctggcgt ttttccatag gctccgcccc cctgacgagc atcacaaaaa tcgacgctca        540
agtcagaggt ggcgaaaccc gacaggacta taaagatacc aggcgtttcc ccctggaagc        600
tccctcgtgc gctctcctgt tccgaccctg ccgcttaccg gatacctgtc gcctttctc        660 ccttcgggaa gcgtggcgct ttctcatagc tcacgctgta ggtatctcag ttcggtgtag        720
gtcgttcgct ccaagctggg ctgtgtgcac gaaccccccg ttcagcccga ccgctgcgcc        780
ttatccggta actatcgtct tgagtccaac ccggtaagac acgacttatc gccactggca        840
gcagccactg gtaacaggat tagcagagcg aggtatgtag cggtgctac agagttcttg        900 aagtggtggc ctaactacgg ctacactaga agaacagtat ttggtatctg cgctctgctg        960
```

```
aagccagtta ccttcggaaa aagagttggt agctcttgat ccggcaaaca aaccaccgct    1020
ggtagcggtg ttttttttgt ttgcaagcag cagattacgc gcagaaaaaa aggatctcaa    1080
gaagatcctt tgatcttttc tacggggtct gacgctcagt ggaacgaaaa ctcacgttaa    1140
gggattttgg tcatgagatt atcaaaaagg atcttcacct agatcctttt aaattaaaaa    1200
tgaagtttta aatcaatcta agtatatat gagtaaactt ggtctgacag ttaccaatgc    1260
ttaatcagtg aggcacctat ctcagcgatc tgtctatttc gttcatccat agttgcctga    1320
ctccccgtcg tgtagataac tacgatacgg gagggcttac catctggccc cagtgctgca    1380
atgataccgc gagacccacg ctcaccggct ccagatttat cagcaataaa ccagccagcc    1440
ggaagggccg agcgcagaag tggtcctgca actttatccg cctccatcca gtctattaat    1500
tgttgccggg aagctagagt aagtagttcg ccagttaata gtttgcgcaa cgttgttgcc    1560
attgctacag gcatcgtggt gtcacgctcg tcgtttggta tggcttcatt cagctccggt    1620
tcccaacgat caaggcgagt tacatgatcc cccatgttgt gcaaaaaagc ggttagctcc    1680
ttcggtcctc cgatcgttgt cagaagtaag ttggccgcag tgttatcact catggttatg    1740
gcagcactgc ataattctct tactgtcatg ccatccgtaa gatgcttttc tgtgactggt    1800
gagtactcaa ccaagtcatt ctgagaatag tgtatgcggc gaccgagttg ctcttgcccg    1860
gcgtcaatac gggataatac cgcgccacat agcagaactt taaaagtgct catcattgga    1920
aaacgttctt cggggcgaaa actctcaagg atcttaccgc tgttgagatc cagttcgatg    1980
taacccactc gtgcacccaa ctgatcttca gcatctttta ctttcaccag cgtttctggg    2040
tgagcaaaaa caggaaggca aaatgccgca aaaagggaa taagggcgac acggaaatgt    2100
tgaatactca tactcttcct ttttcaatat tattgaagca tttatcaggg ttattgtctc    2160
atgagcggat acatatttga atgtatttag aaaaataaac aaataggggt tccgcgcaca    2220
tttccccgaa aagtgccacc tgacgtctaa gaaaccatta ttatcatgac attaacctat    2280 aaaaatagge gtatcacgag gccctttcgt ctcgcgcgtt tcggtgatga cggtgaaaac    2340
ctctgacaca tgcagctccc ggagacggtc acagcttgtc tgtaagcgga tgccgggagc    2400
agacaagccc gtcagggcgc gtcagcgggt gttggcgggt gtcggggctg gcttaactat    2460
gcggcatcag agcagattgt actgagagtg caccatatgc ggtgtgaaat accgcacaga    2520
tgcgtaagga gaaaataccg catcaggcgc cattcgccat tcaggctgcg caactgttgg    2580
gaagggcgat cggtgcgggc ctcttcgcta ttacgccagc tggcgaaagg gggatgtgct    2640
gcaaggcgat taagttgggt aacgccaggg ttttcccagt cacgacgttg taaaacgacg    2700
gccagtgaat tggagatcgg tacttcgcga atgcgtcgag atgtttaaac                2750
```

<210> SEQ ID NO 53
<211> LENGTH: 133
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 53

```
gttccgccca ttctccgccc catggctgac taatttttttt tatttatgca gaggccgagg      60
ccgcctcggc ctctgagcta ttccagaagt agtgaggagg cttttttgga ggcctaggct     120
tttgcaaaaa gct                                                        133
```

EXPRESSION FROM TRANSPOSON-BASED VECTORS AND USES

CROSS-REFERENCES TO RELATED APPLICATIONS

This is application is a division of, and claims priority from, U.S. patent application Ser. No. 16/286,551, filed Feb. 26, 2019, which is a continuation-in-part of, and claims priority from, U.S. patent application Ser. No. 16/072,180, filed Jul. 24, 2018, under 35 U.S.C. § 371, as a U.S. national phase application of United States Patent Cooperation Treaty Application No. PCT/US2017/015130, filed Jan. 26, 2017, which claims priority to provisional application Ser. No. 62/388,391, filed Jan. 27, 2016, all of which are incorporated by reference in their entireties.

SEQUENCE LISTING

The instant application contains a Sequence Listing which has been filed electronically in ASCII format and is hereby incorporated by reference in its entirety. Said ASCII copy, created on Mar. 3, 2021, is named JUST51DIV1_SL.txt and is 36,499 bytes in size.

BACKGROUND

Field of the Invention

This invention relates to recombinant production of proteins in mammalian cells.

Discussion of the Related Art

Industrial scale production of therapeutic proteins by recombinant expression in mammalian cell culture is a relatively recent endeavor that strives for the greatest possible recombinant expression efficiency and product quality characteristics that meet or exceed regulatory guidelines.

Recombinant protein therapeutics offer distinct advantages over small molecule therapeutics in specificity, dosing frequency, and generally lower toxicity. (Catapano, A. L., Papadopoulos, N., The safety of therapeutic monoclonal antibodies: Implications for cardiovascular disease and targeting the PCSK9 pathway, Atherosclerosis 228:18-28 (2013)). The number of recombinant protein therapeutics has increased greatly since the 1980s when this class of therapeutics was first introduced. Despite their advantages, the cost of recombinant protein therapeutics impedes access to most of the world's population. (Moon, S. et al., A win-win solution?: A critical analysis of tiered pricing to improve access to medicines in developing countries, Global. Health 7:1-11 (2011)). A number of strategies to reduce the cost of recombinant protein therapeutics include economies of scale, continuous processing, and process simplification. (Warikoo et al., Integrated continuous production of recombinant therapeutic proteins, Biotechnol. Bioeng. 109:3018-3029 (2012)). In addition, a key factor in reducing cost is increasing the cellular productivity. Significant progress has been made in improving cellular productivity including improvements to expression vectors, cell line engineering, medium development, and as well as other factors. (Dickson, A. J., Cell Line Development, Cell Line Dev. 6:83-96 (2009)).

As higher levels of protein expression in cells are achieved, increasing amounts of cellular machinery are utilized for recombinant protein expression. In microbial systems, the metabolic burden of recombinant protein expression has been shown to slow growth and reduce biomass accumulation. (Wu et al., Metabolic Burden: Cornerstones in Synthetic Biology and Metabolic Engineering Applications, Trends Biotechnol. 34:652-664 (2016)). Depending on the specific expression system, this reduced growth rate and biomass accumulation can be attributed to reduced RNA synthesis, ribosome synthesis, translation initiation, translation elongation, or other factors. (See, e.g., Eames, M., Kortemme, T., Cost-Benefit Tradeoffs in Engineered lac operons, Science 336(6083):911-915 (2012); Kafri et al., The Cost of Protein Production, Cell Rep. 14:22-31 (2016); Scott et al., Interdependence of cell growth and gene expression: origins and consequences, Science 330(6007):1099-1102 (2010)).

Different mammalian cell lines have been used for recombinant protein production, including various lines of Chinese Hamster Ovary (CHO) cells. (See, e.g., Hu et al., Overexpressing Cyclin D1 in a Eukaryotic Cell line, U.S. Pat. No. 6,210,924; Goepfert et al., Protein Expression from Multiple Nucleic Acids, U.S. Pat. No. 8,771,988; and Wurm, F. M., CHO quasispecies—Implications for Manufacturing Processes, Processes 1:296-311; doi:10.3390/pr1030296 (2013)).

In mammalian cells, there tends to be a modest correlation between recombinant protein expression and growth rate indicating that metabolic burden also plays a role in limiting cellular productivity in mammalian expression systems. (Chusainow et al., A study of monoclonal antibody-producing CHO cell lines: What makes a stable high producer? Biotechnol. Bioeng. 102:1182-1196 (2009); Jiang et al., Regulation of recombinant monoclonal antibody production in chinese hamster ovary cells: a comparative study of gene copy number, mRNA level, and protein expression, Biotechnol. Prog. 22:313-318 (2006); Pilbrough, W. et al., Intraclonal protein expression heterogeneity in recombinant CHO cells, PLoS One 4 doi.org/10.1371/journal.pone.0008432 (2009); Wurm, F. M., Production of recombinant protein therapeutics in cultivated mammalian cells, Nat. Biotechnol. 22:1393-1398 (2004)).

Kallehauge et al. showed that reducing expression of a selectable marker using RNAi resulted in increased growth rate. (Kallehauge et al., Ribosome profiling-guided depletion of an mRNA increases cell growth rate and protein secretion, Sci. Rep. 7:40388 (2017)).

Promoters combining enhancer and promoter elements from different genetic sources have been used to enhance recombinant expression in a variety of host cells. (E.g., Harvey, Hybrid promoters, WO 2008/020960 A1; US 2008/12492 A1).

Previous studies have shown that the human CMV promoter and murine CMV promoter can drive high level expression of heterologous expression in mammalian cells. (Mizushima & Nagata, pEF-BOS, a powerful mammalian expression vector. Nucl. Acids Res., 18(17):5322 (1990); Masayuki & Tanaka, The CMV Enhancer Stimulates Expression of Foreign Genes from the Human EF-1a Promoter, Analytical Biochemistry 247:179-181 (1997); Chattellard, P. et al., The Lupac bifunctional marker and its use in protein production, WO 2006/058900 A1; Chattellard, P. et al., Expression vectors comprising the mCMV 1E2 promoter, U.S. Pat. No. 7,824,907; Hjelmstrom et al., Single IFN-beta fused to a mutated IgG Fc fragment, WO 2009/053368 A1; Gaucher et al., Cell line having a high transcription activity for the production of proteins, in particular therapeutic proteins, WO 2008/096070 A2; Flannery et al., Recombinant lubricin molecules and uses thereof, U.S. Pat.

No. 7,642,236; Mosyak et al., Method for identifying or designing a candidate agent that interacts with LINGO-1 polypeptide using a LINGO-1 three-dimensional structure, U.S. Pat. No. 7,693,698; Mosyak et al., WO 2007/092370 A1).

Addition of introns also can increase expression of heterologous proteins (Lacy-Hulbert, A. et al., Interruption of coding sequences by heterologous introns can enhance the functional expression of recombinant genes, Gene Ther. 8(8):649-653 (2001); Brinster, R. L., et al., Introns increase transcriptional efficiency in transgenic mice, Proc. Natl. Acad. Sci. USA 85: 836-40 (1988)). The human and hamster EF-1alpha promoter and introns have been shown to efficiently promote gene expression (Mizushima & Nagata, pEF-BOS, a powerful mammalian expression vector, Nucl. Acids Res. 18(17):5322 (1990); Running Deer, J., & Allison, D. S., High-level expression of proteins in mammalian cells using Transcription Regulatory sequences from Chinese Hamster Ovary EF-1alpha Gene, Biotechnology Progress 20:880-889 (2004); Allison, D. S., Recombinant method for making multimeric proteins, WO 2006/063292 A1; Orlova et al., Improved elongation factor-1alpha-based vectors for stable high-level expression of heterologous proteins in Chinese hamster ovary cells, BMC Biotechnology 14:56 (2014)).

Combinations of human or murine CMV promoters combined with human EF-1alpha introns showed a significant improvement over expression constructs with no intron (Kim, S.-Y. et al., The human elongation factor 1 alpha (EF-1alpha) first intron highly enhances expression of foreign genes from the murine cytomegalovirus promoter, J. Biotechnol. 93(2):183-87 (2002)).

Inducible expression systems have been used in mammalian and microbial cells to control expression levels of recombinant proteins. In order to mitigate the metabolic burden of protein expression during cell growth and to avoid potential toxicity of recombinant proteins in microbial expression systems, an inducible expression system separating growth and recombinant product expression phases is frequently used. This limits the impact of metabolic burden to only the production phase of the culture, when cell growth is not necessarily desirable. (See, e.g., (see, Bentley, W. et al., Plasmid encoded protein: the principal factor in the "metabolic burden" associated with recombinant bacteria, Biotechnology and Bioengineering, Vol. 102, No. 5, 1283-07 (2009); Miroux, B et al., Over-production of proteins in *Escherichia coli* mutant hosts that allow synthesis of some membrane proteins and globular proteins at high levels, J. Mol. Biol. 260:289-298 (1996); Rosano, G L and Ceccarelli, E A, Recombinant protein expression in *Escherichia coli*: Advances and challenges, Front. Microbiol. 5(Art. 172):1-17 (2014)).

In contrast, for isolation of mammalian cell lines suited for industrial production of proteins, constitutive expression vectors are typically employed. Inducible systems are typically utilized for only those proteins that are toxic when over expressed.

There are several reports that expression of toxic proteins in mammalian systems leads to slower growth or cell line instability. (Umana, P. et al., Tetracycline-regulated overexpression of glycosyltransferases in Chinese hamster ovary cells, Biotechnol. Bioeng. 65(5):542-549 (1999); Misaghi, S. et al., It's time to regulate: Coping with product-induced nongenetic clonal instability in CHO cell lines via regulated protein expression, Biotechnol Prog. 2014; 30(6):1432-1440 (2014); Jones, J. et al., Optimization of tetracycline-responsive recombinant protein production and effect on cell growth and ER stress in mammalian cells, Biotechnol Bioeng. 91(6):722-732 (2005)). For example, Misaghi et al. (2014), supra, showed that using a regulated expression system that restricts expression of moderately toxic antibody during cell line development allowed isolation of stable cell lines, whereas constitutive expression of this protein yielded unstable cell lines, consistent with the idea that the metabolic burden of a toxic protein can result in the enrichment of clones with reduced protein expression. Similarly, regulated expression of the moderately toxic protein transferrin showed that clones isolated in the repressed state expressed at higher levels compared to clones where transferrin was constitutively expressed (Jones et al. (2005), supra).

Using a cumate-regulated system, Poulain et al. showed an increase in expression of an Fc fusion protein, as well as an antibody, when cells were selected in the absence of expression, when compared to two constitutive promoters. In this case, neither the Fc fusion protein nor the antibody displayed obvious toxicity. (Poulain, A. et al., Rapid protein production from stable CHO cell pools using plasmid vector and the cumate gene-switch, J Biotechnol. 255:16-27 (2017)).

Using a doxycycline-inducible system, Li et al. observed fewer numbers of clones when cells were selected in presence of protein expression than when compared with non-induced cultures. This observation is also consistent with the hypothesis of metabolic burden impacting growth of transfected cells. (Li, Z et al., Simple piggyBac transposon-based mammalian cell expression system for inducible protein production, Proc Natl Acad Sci USA. 110(13):5004-5009 (2013)).

The Tet repressor (TetR), which is encoded by the bacterial transposon, Tn10, has been used to regulate inducible gene expression in mammalian cells. TetR binds to a DNA sequence (TetO) in the absence of tetracycline. Upon binding to tetracycline, TetR undergoes a conformational change that abrogates the binding of TetR to TetO. Yao et al. had shown that the human CMV enhancer promoter could be regulated by tetracycline by incorporating a TetO sequence between the TATA box and the transcriptional start site (TSS). (See, Yao et al., Tetracycline repressor, tetR, rather than the tetR-mammalian cell transcription factor fusion derivatives, regulates inducible gene expression in mammalian cells, Hum. Gene Ther. 9(13):1939-50 (1998); Yao et al. U.S. Pat. No. 5,972,650; Yao et al., WO99/00510).

There is a need for enhanced recombinant expression of proteins by mammalian cells in large batch or continuous culture to support robust production of biologics in a variety of mammalian cell lines, and there is a need for improved methods of selecting stable mammalian cells lines that can deliver enhanced expression. The present invention provides these.

SUMMARY OF THE INVENTION

The present invention relates to a recombinant expression vector for stable expression of one or more proteins of interest in mammalian host cells, by promoting genomic integration of the expression cassettes included in the vector, by virtue of the 5' and 3' PiggyBac transposon ITRs the vector comprises. In one embodiment, the recombinant expression vector of the invention includes:

(a) a 5' PiggyBac ITR comprising the nucleotide sequence of SEQ ID NO:45;
(b) a first expression cassette, comprising:
  (i) a control sequence comprising:
    (1) a mCMV enhancer sequence, comprising a mCMV enhancer element (mCMV-E) and a CMV promoter (CMV-P) sequence at its 3' end, operably linked 5' to a rat EF-1alpha intron sequence;
    (2) an intervening first leader sequence operably linked, 3' to the CMV-P sequence of the mCMV enhancer sequence, and 5' to the rat EF-1alpha intron sequence; and
    (3) a second leader sequence operably linked 3' to the rat EF-1alpha intron sequence;
  (ii) an open reading frame encoding an protein of interest operably linked to the control sequence; and
  (iii) a polyadenylation site operably linked 3' to the open reading frame;
(c) a second expression cassette, comprising:
  (i) a weak constitutive promoter, operably linked to an open reading frame encoding a selectable marker; and
  (ii) a polyadenylation site operably linked 3' to the open reading frame; and
(d) a 3' PiggyBac ITR comprising the nucleotide sequence of SEQ ID NO:47.

The inventive combination of a mCMV enhancer sequence with a rat EF-1alpha intron sequence in the hybrid promoter facilitates recombinant expression of proteins of interest, particularly by CHO cells, with high titers and high specific productivity suitable for industrial production of biologic molecules, such as, but not limited to, an antigen binding protein, an immunoglobulin, an antibody or antibody fragment, or hormone (e.g., as human therapeutics to prevent or treat disease).

In other embodiments, the recombinant expression vector of the invention allows stable inducible expression of the one or more proteins of interest in mammalian host cells, by virtue of one or more TetO sequences in a control sequence of an expression cassette, while the vector promotes genomic integration of the expression cassettes included in the vector, by virtue of the 5' and 3' PiggyBac transposon ITRs the vector comprises. In particular, the recombinant expression vector, comprises:
(a) a 5' PiggyBac ITR comprising the nucleotide sequence of SEQ ID NO:45;
(b) a first expression cassette, comprising:
  (i) a control sequence comprising:
    (1) a mCMV enhancer sequence, comprising a mCMV enhancer element (mCMV-E) and a CMV promoter (CMV-P) sequence at its 3' end, operably linked 5' to a rat EF-1alpha intron sequence, comprising one or more TetO sequences inserted within the CMV promoter sequence of the first promoter;
    (2) an intervening first leader sequence operably linked, 3' to the CMV-P sequence of the mCMV enhancer sequence, and 5' to the rat EF-1alpha intron sequence; and
    (3) a second leader sequence operably linked 3' to the rat EF-1alpha intron sequence;
  (ii) an open reading frame encoding a protein of interest operably linked to the control sequence; and
  (iii) a polyadenylation site operably linked 3' to the open reading frame;
(c) a second expression cassette, comprising:
  (i) a weak constitutive promoter, operably linked to an open reading frame encoding a selectable marker; and
  (ii) a polyadenylation site operably linked 3' to the open reading frame; and
(d) a 3' PiggyBac ITR comprising the nucleotide sequence of SEQ ID NO:47. An example of such a vector is pJVec_5 (see, FIG. 28), further described herein.

This recombinant expression vector, allowing inducible expression of the protein of interest in a mammalian host cell, stably transfected therewith, is useful, inter alia, for a method of selecting a stable production cell line for manufacturing the protein of interest. The inventive method comprises the following steps:
(a) culturing a mammalian host cell stably transfected with the recombinant expression vector described in the paragraph above (which comprises the one or more TetO sequences in a control sequence of an expression cassette), under selective pressure with respect to a selectable marker constitutively expressed from the weak constitutive promoter, in an aqueous medium under physiological conditions, wherein the mammalian host cell is capable of expressing TetR, in the absence of tetracycline or a tetracycline analog in the medium, whereby expression of protein from the first expression cassette is repressed;
(b) selecting a viable cell line from the host cell(s) cultured in step (a);
(c) culturing the viable cell line from step (b) in an aqueous medium containing tetracycline or a tetracycline analog in an amount sufficient to bind TetR in the host cell(s), whereby expression of the protein of interest by the host cell is derepressed; and
(d) detecting the protein of interest in the culture medium;
(e) selecting a stable production cell line from step (c) that produces a greater amount of the protein of interest relative to a control transfectant in which the aqueous medium in steps (a) and (c) contained tetracycline or a tetracycline analog in an amount sufficient to bind TetR in the host cell, whereby the expression of the protein of interest was derepressed in the control transfectant.

In another aspect, the invention is directed to a recombinant expression vector that is particularly useful for expression of immunoglobulins, e.g., antibodies, and to a mammalian host cell (e.g., a CHO cell) containing the vector. In some embodiments, the recombinant expression vector includes:
(a) a first expression cassette, comprising:
  (i) a control sequence comprising:
    (1) a mCMV enhancer sequence, comprising a mCMV enhancer element (mCMV-E) and a CMV promoter (CMV-P) sequence at its 3' end, operably linked 5' to a rat EF-1alpha intron sequence;
    (2) an intervening first leader sequence operably linked, 3' to the CMV-P sequence of the mCMV enhancer sequence, and 5' to the rat EF-1alpha intron sequence; and
    (3) a second leader sequence operably linked 3' to the rat EF-1alpha intron sequence;
  (ii) an open reading frame encoding a first immunoglobulin subunit operably linked to the control sequence; and
  (iii) a first polyadenylation site operably linked 3' to the open reading frame;
(b) a second expression cassette 3' to the first expression cassette, comprising:
  (i) a control sequence comprising a promoter;
  (ii) an open reading frame encoding a second immunoglobulin subunit operably linked to the promoter; and
  (iii) a second polyadenylation site operably linked 3' to the open reading frame; and (c) a transcription termination sequence 3' to the first expression cassette and 5' to the second expression cassette.

Other embodiments of the recombinant (expression vector of the invention allow inducible expression of the one or more proteins of interest in mammalian host cells, by virtue of one or more TetO sequences in a control sequence of an expression cassette. These embodiments of the recombinant expression vector include:

(a) a first expression cassette, comprising:
   (i) a control sequence comprising:
      (1) a mCMV enhancer sequence, comprising a mCMV enhancer element (mCMV-E) and a CMV promoter (CMV-P) sequence at its 3' end, operably linked 5' to a rat EF-1alpha intron sequence, comprising one or more TetO sequences inserted within the CMV-P sequence;
      (2) an intervening first leader sequence operably linked, 3' to the CMV-P sequence of the mCMV enhancer sequence, and 5' to the rat EF-1alpha intron sequence; and
      (3) a second leader sequence operably linked 3' to the rat EF-1alpha intron sequence;
   (ii) an open reading frame encoding a first immunoglobulin subunit operably linked to the control sequence; and
   (iii) a first polyadenylation site operably linked 3' to the open reading frame;
(b) a second expression cassette 3' to the first expression cassette, comprising:
   (i) a control sequence comprising a promoter;
   (ii) an open reading frame encoding a second immunoglobulin subunit operably linked to the promoter; and
   (iii) a second polyadenylation site operably linked 3' to the open reading frame; and
(c) a transcription termination sequence 3' to the first expression cassette and 5' to the second expression cassette.

The present invention also relates to mammalian host cell (e.g., a CHO cell) containing any of the inventive recombinant expression vector(s) and a method of producing a protein of interest, in vitro, that involves culturing the mammalian host cell containing the inventive expression vector, in an aqueous medium under physiological conditions permitting expression of the protein of interest; and recovering the protein of interest from the medium.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 12 shows a schematic comparison of segments of the DNA sequences of pJV57 and pJV60. In the segment shown of pJV60 (SEQ ID NO:18), the TetO sequences in the corresponding segment of pJV57 (SEQ ID NO:17) were changed to match the sequences that increased expression surrounding the transcription start site in the study by Patwardhan et al., "High-resolution analysis of DNA regulatory elements by synthetic saturation mutagenesis", Nature Biotechnology 27(12):1173-75 (2009).

FIG. 13 shows a schematic comparison of segments of the DNA sequences of pJV56 and pJV59. In this segment of pJV59 (SEQ ID NO:20), optimized hCMV promoter sequences in the corresponding sequence of pJV56 (SEQ ID NO:19) replaced part of the mCMV promoter (mCMV-P) sequence in a variation of the mCMV enhancer/rat EF-1α intron hybrid promoter of the invention.

FIG. 19A shows a schematic representation of vectors pJVEC_2 and pJVec_3 when integrated into the genome to stably transfect TetR-GS KO cells. GS=glutamine synthetase; CP=constitutive promoter; mCMV=mouse cytomegalovirus promoter; TPL=tripartite leader sequence; rEF-1a: =rat EF-1a intron; Fc-A=recombinant Fc-fusion protein; pA=polyA; TetO=Tet-operator sequence. FIG. 19B shows growth profiles, and FIG. 19C shows viability over the first 3 weeks of selection in cell culture medium containing 75 mM L-methionine sulfoximine (MSX). Circles are cultures without the tetracycline analog, doxycycline (−Dox), and star symbols are cultures with doxycycline (+Dox). Each trace represents a transfection replicate. n=4.

FIG. 20A shows Day 10 titers of production cultures in CD OptiCHO™ medium. (−) denotes pools that did not receive doxycycline (Dox) during selection. FIG. 20B shows viable cell density (VCD) and average viability over time. Circles are cultures without Dox and star symbols are cultures with Dox. Each trace represents a transfection replicate. n=4.

FIG. 21A shows a schematic representation of the vector map of inducible, pJVec_4, when integrated into the genome. FIG. 21B shows titer and qP of pools on day 10 of fed-batch cultures in CD OptiCHO™ medium. n=4. FIG. 21C shows a correlation between protein production (qP) and mAb light chain (LC) and heavy chain (HC) mRNA levels during fed-batch production. Data represented by "+" symbols are +Dox; and circles represent −Dox.

FIG. 22A-B illustrates expression vector pJVec_5 and expression by transfected CHO cells. FIG. 22A shows a schematic representation of the vector map of pJVec_5, when integrated into the genome. FIG. 22B shows selection curves of transfected pools in CD OptiCHO™ medium −glutamine (−Q) and +/−Dox. n=3 each. Circles represent data points for cultures without Dox, and "+" symbols represent data points for cultures with Dox.

FIG. 23A shows Day 10 titers/qP from a fed-batch protein production in a chemically defined culture medium without growth factors or other proteins, with Hyclone feeds A/B. n=3. FIG. 23B shows growth curves with Dox added during production. FIG. 23C shows growth curves of cultures in which Dox was not added during production. (−) denotes pools that did not receive Dox during selection.

FIG. 24B shows the LC/HC ratio.

DETAILED DESCRIPTION OF EMBODIMENTS

Figure 1:
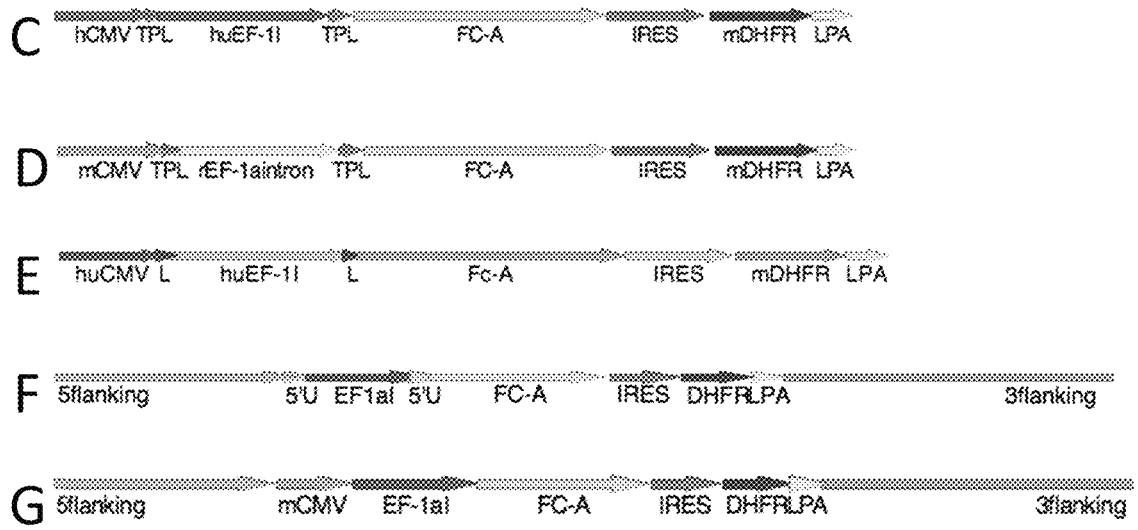
FIG. 1 shows schematic maps of some exemplary expression constructs.

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

In some embodiments, the present invention relates to a recombinant PiggyBac transposon-based vector for stable expression of one or more proteins of interest in mammalian host cells. The PiggyBac (PB) transposon is a mobile genetic element that efficiently transposes between vectors and host cell chromosomes via a "cut and paste" transposition mechanism. During transposition, the PB transposase recognizes transposon-specific inverted terminal repeat sequences (ITRs) located on both the 5' and 3' ends of the transposon-based vector and moves the vector contents between the 5' and 3' ITRs from the original vector sites and integrates them into TTAA chromosomal sites. For purposes of the invention the "5' PiggyBac ITR" comprises the nucleotide sequence of SEQ ID NO:45: CCCTAGAAAGA-TAGTCTGCGTAAAATTGACGCATGCATTCTTGAAAT-ATTGCTCT CTCTTTCTAAATAGCGCGAATCCG TCGCTGTGCATTTAGGACATCTCAGTCGCCG CTTG-GAGCTCCCGTGAGGCGTGCTTGTCAATGCGGTA AGTGTCACTGATTTTGAA CTATAACGACCGCGT-GAGTCAAAATGACGCATGATTATCTTT-TACGTGACTTTTA AGATTTAACTCATACGATAAT-TATATTGTTATTTCATGTTCTACTTACGTGATAAC TTATTATATATATATTTTCTTGTTATAGATATC//SEQ ID NO:45. For purposes of the invention "3' PiggyBac ITR" comprises the nucleotide sequence of SEQ ID NO:47:

```
                                SEQ ID NO: 47
GATAAAAGTTTTGTTACTTTATAGAAGA

AATTTTGAGTTTTTGTTTTTTTTAATAA

ATAAATAAACATAAATAAATTGTTTGTT

GAATTTATTATTAGTATGTAAGTGTAA

ATATAATAAAACTTAATATCTATTCAAA

TTAATAAATAAACCTCGATATACAGAC

CGATAAAACACATGCGTCAATTTTACAC
```

```
ATGATTATCTTTAACGTACGTCACAAT

ATGATTATCTTTCTAGGG//.
```

The present invention relates to a hybrid promoter for regulating recombinant expression of one or more proteins of interest. The inventive promoter includes a mCMV enhancer sequence operably linked to a rat EF-1alpha intron sequence. The term "mCMV," used interchangeably with "muCMV," refers to murine cytomegalovirus, which is a herpesvirus of the subfamily betaherpesviridae. The mCMV is a double-stranded enveloped DNA virus with host specificity for mice. Similarly, the term "hCMV," or interchangeably "huCMV," refers to human cytomegalovirus.

The "mCMV enhancer sequence," with respect to the present invention, includes:
(i) a mCMV enhancer element ("mCMV-E"); and, at the 3' end of the mCMV enhancer sequence,
(ii) a CMV promoter sequence ("CMV-P"; i.e., a nucleotide sequence segment beginning at, and including, the TATA box through the start site of transcription); the CMV promoter sequence can be derived from mCMV, hCMV, simian CMV, rat CMV, or any other variety of CMV, or it can be an optimized version of a CMV-P, which is functional to enable transcription in mammalian cells, such as CHO cells.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., Molecular Cloning. A Laboratory Manual. Cold Spring Harbor Laboratory, Cold Spring Harbor, N.Y. (1982). A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

The term "naturally occurring" as used throughout the specification in connection with biological materials such as polypeptides, nucleic acids, host cells, and the like, refers to materials which are found in nature.

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes, including mammalian cells, can include promoters comprising one or a plurality of recognition sites for transcription factors, transcription enhancer sequences or elements, intron sequences, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

A "promoter" is a region of DNA including a site at which RNA polymerase binds to initiate transcription of messenger RNA by one or more downstream structural genes. Promoters are located near the transcription start sites of genes, on the same strand and upstream on the DNA (towards the 5' region of the sense strand). Promoters are typically about 100-1000 bp in length. A common feature of promoter regions in eukaryotes is the TATA box, it is found about 25 bases upstream from the transcription start site and has the ideal sequence of TATAAAT. The closeness of the actual sequence to this ideal sequence effects the ability of the RNA polymerase complex to bind to the DNA and hence initiate the transcription process.

In some embodiments, the inventive recombinant expression vector includes an expression cassette comprising a weak constitutive promoter, operably linked to an open reading frame encoding a selectable marker. A "constitutive promoter" is: (1) a promoter sequence that initiates mRNA synthesis independent of the influence of regulation, or (2) a promoter sequence that initiates mRNA synthesis independent, or substantially independent, of the influence of regulation, under physiological conditions normally associated with cell culture for the expression of a protein of interest in an industrial protein manufacturing setting. The specific nucleic acid (i.e., nucleotide) sequence of the promoter determines the strength of the promoter (a strong promoter leads to a relatively high rate of transcription initiation). Commonly used constitutive promoters for mammalian cell systems include simian virus 40 early promoter (SV40), cytomegalovirus immediate-early promoter (CMV), human Ubiquitin C promoter (UBC), human elongation factor 1a promoter (EF1A), mouse phosphoglycerate kinase 1 promoter (PGK), and chicken β-Actin promoter coupled with CMV early enhancer (CAGG). A "weak constitutive promoter" is a constitutive promoter that will not initiate transcription as efficiently as a strong promoter, for example, a modified version of one of the foregoing list of constitutive promoters. Thus, an example of a weak constitutive promoter is a deleted SV40 promoter. (See, e.g., Hartman et al., Vectors and host cells comprising a modified SV40 promoter for protein expression, U.S. Ser. No. 10/053, 720; and Hartman et al., DAC HYP compositions and methods, U.S. Pat. No. 9,260,528B2). Another useful example of a weak constitutive promoter for purposes of the present invention is the PGK promoter described in Qin J Y et al. (Qin, J Y, Zhang L, Clift K L, Hulur I, Xiang A P, Ren B-Z, et al. (2010), Systematic Comparison of Constitutive Promoters and the Doxycycline-Inducible Promoter. PLoS ONE 5(5): e10611. doi.org/10.1371/journal.pone.0010611; see, also, e.g., Li, J. & Zhang, Y., Relationship between promoter sequence and its strength in gene expression, Eur. Phys. J. E 37: 86 (2014)). One particularly useful example of a weak constitutive promoter for purposes of the present invention is a deleted SV40 promoter comprising the nucleotide sequence of SEQ ID NO:46:

```
                                           SEQ ID NO: 46
TCCCGCCCCTAACTCCGCCCAGTTCCGC

CCATTCTCCGCCCCATGGCTGACTAATT

TTTTTTATTTATGCAGAGGCCGAGGCCG

CCTCGGCCTCTGAGCTATTCCAGAAGT

AGTGAGGAGGCTTTTTTGGAGGCCTAGG

CTTTTGCAAAAAGCT//.
```

Figure 28:
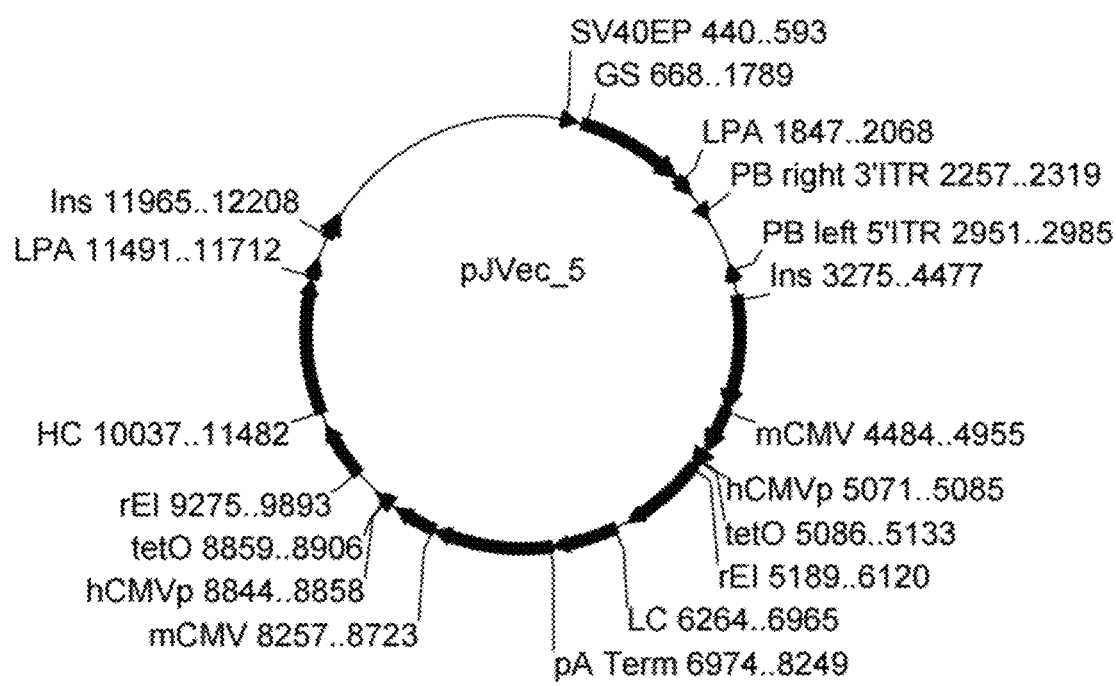
FIG. 28 shows a schematic representation of the vector map of inducible, pJVec_5.

The deleted SV40 promoter comprising the nucleotide sequence of SEQ ID NO:46 is used, e.g., in vector pJVec_5 (see, FIG. 28). Another useful example is a further truncation of the SV40 promoter that further weakens the promoter, e.g., a deleted SV40 promoter comprising the nucleotide sequence of SEQ ID NO:53: GTTCCGCCCATTCTCCGCCCCATGGCTGACTAAT-TTTTTTTATTTATGCAGAGGCC GAGGCCGCCTCGGCCTCTGAGCTAT-TCCAGAAGTAGTGAGGAGGCTTTTTTGGAG GCCTAGGCTTTTGCAAAAAGCT//SEQ ID NO:53. The weak constitutive promoter is operably linked to an open reading frame encoding a selectable marker, which selectable marker confers upon cells transfected with an expression vector, as described herein, a trait or characteristic that be used to identify transfected cells from non-transfected cells. Useful selectable markers and there coding sequences are well known in the art. They can confer traits such as, but not limited to, resistance to a toxin, heavy metal, antibiotic, or other agent, prototrophy in an auxotrophic host, the ability to grow in a medium free of an essential nutrient, the ability to synthesize an essential metabolite. Selectable markers commonly used in transfecting mammalian cells, such as CHO cells, include, but are not limited to, glutamine synthetase (GS), puromycin resistance (PurR), neomycin resistance (NeoR), zeomycin resistance (ZeoR), or dihydrofolate reductase (DHFR). A useful example of a glutamine synthetase coding sequence has the nucleotide sequence of SEQ ID NO:49, or a degenerate DNA sequence:

```
                                           SEQ ID NO: 49
ATGGCCACCTCAGCAAGTTCCCACTTGAACAAAAACATCAAGCA

AATGTACTTGTGCCTGCCCCAGGGTGAGAAAGTCCAAGCCATGT

ATATCTGGGTTGATGGTACTGGAGAAGGACTGCGCTGCAAAACC

CGCACCCTGGACTGTGAGCCCAAGTGTGTAGAAGAGTTACCTGA

GTGGAATTTTGATGGCTCTAGTACCTTTCAGTCTGAGGGCTCCA

ACAGTGACATGTATCTCAGCCCTGTTGCCATGTTTCGGGACCCC

TTCCGCAGAGATCCCAACAAGCTGGTGTTCTGTGAAGTTTTCAA

GTACAACCGGAAGCCTGCAGAGACCAATTTAAGGCACTCGTGTA

AACGGATAATGGACATGGTGAGCAACCAGCACCCCTGGTTTGGA

ATGGAACAGGAGTATACTCTGATGGGAACAGATGGGCACCCTTT

TGGTTGGCCTTCCAATGGCTTTCCTGGGCCCCAAGGTCCGTATT

ACTGTGGTGTGGGCGCAGACAAAGCCTATGGCAGGGATATCGTG

GAGGCTCACTACCGCGCCTGCTTGTATGCTGGGGTCAAGATTAC

AGGAACAAATGCTGAGGTCATGCCTGCCCAGTGGGAATTTCAAA
```

-continued
```
TAGGACCCTGTGAAGGAATCCGCATGGGAGATCATCTCTGGGTG

GCCCGTTTCATCTTGCATCGAGTATGTGAAGACTTTGGGGTAAT

AGCAACCTTTGACCCCAAGCCCATTCCTGGGAACTGGAATGGTG

CAGGCTGCCATACCAACTTTAGCACCAAGGCCATGCGGGAGGAG

AATGGTCTGAAGCACATCGAGGAGGCCATCGAGAAACTAAGCAA

GCGGCACCGGTACCACATTCGAGCCTACGATCCCAAGGGGGCC

TGGACAATGCCCGTCGTCTGACTGGGTTCCACGAAACGTCCAAC

ATCAACGACTTTTCTGCTGGTGTCGCCAATCGCAGTGCCAGCAT

CCGCATTCCCCGGACTGTCGGCCAGGAGAAGAAAGGTTACTTTG

AAGACCGCCGCCCCTCTGCCAATTGTGACCCCTTTGCAGTGACA

GAAGCCATCGTCCGCACATGCCTTCTCAATGAGACTGGCGACGA

GCCCTTCCAATACAAAAACTAA//.
```

In general, an "enhancer" is a short (50-1500 bp) region of DNA that can be bound with one or more activator proteins (transcription factors) to activate transcription of a gene.

A mCMV enhancer sequence useful in the inventive hybrid promoter comprises a nucleotide sequence at least 95%, at least 96%, at least 97%, at least 98%, at least 99%, or 100% identical to the nucleotide sequence of SEQ ID NO:2, which contains a CMV promoter (CMV-P) sequence at its 3' end (bold underlined sequence in SEQ ID NO:2) beginning at nucleotide position 588 (including a TATA-box and transcriptional start site, i.e., TATAAGAGG CGCGA C CAGCG TCGG TACCG//SEQ ID NO:28; bold underlined in SEQ ID NO:2 below; SEQ ID NO:28 also comprises SEQ ID NO:26):

```
                            SEQ ID NO: 2
GTCAACAGGA AAGTTCCATT GGAGCCAAGT ACATTGAGTC

AATAGGGACT TTCCAATGGG TTTTGCCCAG TACATAAGGT

CAATGGGAGG TAAGCCAATG GGTTTTTCCC ATTACTGGCA

CGTATACTGA GTCATTAGGG ACTTTCCAAT GGGTTTTGCC

CAGTACATAA GGTCAATAGG GGTGAATCAA CAGGAAAGTC

CCATTGGAGC CAAGTACACT GAGTCAATAG GGACTTTCCA

TTGGGTTTTG CCCAGTACAA AAGGTCAATA GGGGGTGAGT

CAATGGGTTT TTCCCATTAT TGGCACGTAC ATAAGGTCAA

TAGGGGTGAG TCATTGGGTT TTTCCAGCCA ATTTAATTAA

AACGCCATGT ACTTTCCCAC CATTGACGTC AATGGGCTAT

TGAAACTAAT GCAACGTGAC CTTTAAACGG TACTTTCCCA

TAGCTGATTA ATGGGAAAGT ACCGTTCTCG AGCCAATACA

CGTCAATGGG AAGTGAAAGG GCAGCCAAAA CGTAACACCG

CCCCGGTTTT CCCCTGGAAA TTCCATATTG GCACGCATTC

TATTGGCTGA GCTGCGTTCT ACGTGGG

TAT AAGAGGCGCG ACCAGCGTCG GTACCG//.
```

Another exemplary mCMV enhancer sequence useful in the inventive hybrid promoter comprises a nucleotide sequence at least 95%, at least 96%, at least 97%, at least 98%, at least 99%, or 100% identical to the nucleotide sequence of SEQ ID NO:33, which contains a CMV promoter sequence at its 3' end (bold underlined sequence in SEQ ID NO:33) beginning at position 588, which includes a TATA-box and transcriptional start site, i.e., TATATAAGCAGAGCTCGTTTAGT-GAACCGTCAGTTCGTCTCTAGACGCCAACCG//SEQ ID NO:35; bold underlined sequence in SEQ ID NO:33 below; SEQ ID NO:35 also comprises SEQ ID NO:24):

```
                            SEQ ID NO: 33
GTCAACAGGAAAGTTCCATTGGAGCCAAGTACATTGAGTCAAT

AGGGACTTTCCAATGGGTTTTGCCCAGTACATAAGGTCAATGG

GAGGTAAGCCAATGGGTTTTTCCCATTACTGGCACGTATACTG

AGTCATTAGGGACTTTCCAATGGGTTTTGCCCAGTACATAAGG

TCAATAGGGGTGAATCAACAGGAAAGTCCCATTGGAGCCAAGT

ACACTGAGTCAATAGGGACTTTCCATTGGGTTTTGCCCAGTAC

AAAAGGTCAATAGGGGGTGAGTCAATGGGTTTTTCCCATTATT

GGCACGTACATAAGGTCAATAGGGGTGAGTCATTGGGTTTTTC

CAGCCAATTTAATTAAAACGCCATGTACTTTCCCACCATTGAC

GTCAATGGGCTATTGAAACTAATGCAACGTGACCTTTAAACGG

TACTTTCCCATAGCTGATTAATGGGAAAGTACCGTTCTCGAGC

CAATACACGTCAATGGGAAGTGAAAGGGCAGCCAAAACGTAAC

ACCGCCCCGGTTTTCCCCTGGAAATTCCATATTGGCACGCATT

CTATTGGCTGAGCTGCGTTCTACGTGGGTATATAAGCAGAGCT

CGTTTAGTGAACCGTCAGTTCGTCTCTAGACGCCAACCG//.
```

In some useful embodiments, in which tetracycline-inducible expression is desired, the inventive hybrid promoter comprises one or more TetO sequences operably linked 3' to the mCMV enhancer sequence, inserted within the CMV promoter (CMV-P) sequence at the 3' end of the mCMV enhancer sequence. A "TetO" sequence means a nucleotide sequence, which maintains the ability to bind tetracycline repressor protein (TetR). The TetO sequence is placed so that, in the presence of TetR protein, there is binding of TetR to the TetO sequence, thereby disrupting transcription to a detectable extent, compared to a control not having TetO in the promoter driving transcription of a gene of interest, or to a control not having TetR. Examples of the TetO sequence include a sequence having at least 95%, at least 96%, at least 97%, at least 98%, at least 99%, or 100% sequence identity to SEQ ID NO:29 (TCCCTATCAGTGA-TAGAGATCTCCCTATCAGTGATAGAGA//SEQ ID NO:29) or having at least 95%, at least 96%, at least 97%, at least 98%, at least 99%, or 100% sequence identity to SEQ ID NO:34 (CTCCCTATCAGTGATCAGTTCCTCCC-TATCAGTGATAGAGA//SEQ ID NO:34). In some useful embodiments, there can be additional nucleotide residues 5' or 3' to the TetO sequence(s), or there can be intervening nucleotide linker sequences, as long as the ability to bind TetR protein is not eliminated.

"Repression," or "repressed," within the context of the invention, refers to the interference of transcription of a gene of interest (encoding a protein of interest), occurring when TetR protein binds to a TetO binding site in the promoter that drives expression of the gene of interest, resulting in decreased expression of the protein of interest by the cell(s)

(which are cell(s) that express TetR). Expression of a gene of interest or of a protein of interest is said to be "derepressed," when, in the presence of tetracycline in the medium, expression of the protein of interest is at least 1.5-fold over the basal levels of expression by the cell(s) in the absence of tetracycline in the medium.

"Tetracycline" means tetracycline or an analog of tetracycline, such as doxycycline, anhydrotetracycline, minocycline, oxytetracycline, methacycline, chlortetracycline, or COL-3 (Chemically modified tetracycline-3).

The recombinant expression vectors of the present invention can optionally contain one or more insulator elements, if desired. "Insulator elements," or interchangeably, "insulator sequences," are DNA sequences that protect transcription units from outside regulatory influence. When placed between a transcription unit and an enhancer sequence, these elements can block the action of the enhancer sequence on the transcription unit. In constructs where insulator sequences flank a transcription unit, they can confer position independent expression when transfected in cells. Many insulator elements have been identified and characterized including the chicken HS4, mouse H19, and *Xenopus* ARS. (See, e.g., Kanduri, C. et al., The 5' flank of mouse H19 in an unusual chromatin conformation unidirectionally blocks enhancer-promoter communication, Current Biology 10(8): 449-457 (2000); Recillas-Targa, F. et al., Position-effect protection and enhancer blocking by the chicken beta-globin insulator are separable activities. Proc. Nat. Acad. Sci. USA 99(10):6883-6888 (2002); Valenzuela, L., & Kamakaka, R. T., Chromatin Insulators, Annu. Rev. Genet. 40:107-38 (2006); Watanabe, S. et al., Functional analysis of the sea urchin-derived arylsulfatase (Ars)-element in mammalian cells. Genes to Cells, 11(9), 1009-1021 (2006)).

A rat EF-1alpha intron sequence useful in the inventive hybrid promoter comprises a nucleotide sequence at least 95%, at least 96%, at least 97%, at least 98%, at least 99%, or 100% identical to the nucleotide sequence of SEQ ID NO:4:

```
                                              SEQ ID NO: 4
GTGAGTGGCGGGTGTGGCTTCCGCGGGCCCCGGAGCTGGAGCCC

TGCTCTGAGCGGGCCGGGCTGATATGCGAGTGTCGTCCGCAGGG

TTTAGCTGTGAGCATTCCCACTTCGAGTGGCGGGCGGTGCGGGG

GTGAGAGTGCGAGGCCTAGCGGCAACCCCGTAGCCTCGCCTCGT

GTCCGGCTTGAGGCCTAGCGTGGTGTCCGCCGCCGCGTGCCACT

CCGGCCGCACTATGCGTTTTTTGTCCTTGCTGCCCTCGATTGCC

TTCCAGCAGCATGGGCTAACAAAGGGAGGGTGTGGGGCTCACTC

TTAAGGAGCCCATGAAGCTTACGTTGGATAGGAATGGAAGGGCA

GGAGGGGCGACTGGGGCCCGCCCGCCTTCGGAGCACATGTCCGA

CGCCACCTGGATGGGGCGAGGCCTGTGGCTTTCCGAAGCAATCG

GGCGTGAGTTTAGCCTACCTGGGCCATGTGGCCCTAGCACTGGG

CACGGTCTGGCCTGGCGGTGCCGCGTTCCCTTGCCTCCCAACAA

GGGTGAGGCCGTCCCGCCCGGCACCAGTTGCTTGCGCGGAAAGA

TGGCCGCTCCCGGGGCCCTGTTGCAAGGAGCTCAAAATGGAGGA

CGCGGCAGCCCGGTGGAGCGGGCGGGTGAGTCACCCACACAAG

GAAGAGGGCCTTGCCCCTCGCCGGCCGCTGCTTCCTGTGACCCC
```

```
GTGGTCTATCGGCCGCATAGTCACCTCGGGCTTCTCTTGAGCAC

CGCTCGTCGCGGCGGGGGAGGGGATCTAATGGCGTTGGAGTTT

GTTCACATTTGGTGGGTGGAGACTAGTCAGGCCAGCCTGGCGCT

GGAAGTCATTCTTGGAATTTGCCCCTTTGAGTTTGGAGCGAGGC

TAATTCTCAAGCCTCTTAGCGGTTCAAAGGTATTTTCTAAACCC

GTTTCCAG//.
```

The inventive hybrid promoter also includes an intervening first leader sequence, operably linked 3' to the mCMV enhancer and 5' to the EF-1alpha intron sequence in an operable orientation. The intervening first leader sequence is about 10 to 200 nucleotide residues in length—more preferably about 10 to 60 nucleotide residues in length or even more preferably about 20-50 nucleotide residues in length—and lacks any secondary structure with stability greater than 20 kcal and lacks any ATG translational start sites. An example of a useful first leader sequence is an untranslated (5'UTR) leader sequence derived from adenovirus tripartite leader (TPL), i.e., the nucleotide sequence of SEQ ID NO:3:

```
                                              SEQ ID NO: 3
TACCTCTTCCGCATCGCTGTCTGCGAGGGCCAGCTGTTGGG//.
```

The inventive hybrid promoter also includes a second leader sequence operably linked 3' to the EF-1 alpha intron sequence in an operable orientation. The second leader sequence is about 5 to 200 nucleotide residues in length—more preferably about 10 to 200 nucleotide residues in length or even more preferably about 10-150 nucleotide residues in length—and lacks any secondary structure with stability greater than 20 kcal and lacks any ATG translational start sites. An example of a useful second leader sequence is another untranslated (5'UTR) leader sequence region derived from adenovirus tripartite leader (TPL), i.e., the nucleotide sequence of SEQ ID NO:5:

```
                                              SEQ ID NO: 5
CTCGCGGTTGAGGACAAACTCTTCGCGGTCTTTCCAGTACTCTT

GGATCGGAAACCCGTCGGCCTCCGAACGGTACTCCGCCACCGAG

GGACCTGAGCGAGTCCGCATCGACCGGATCGGAAAACCTC//.
```

For other examples of useful leader sequences and design principles, see, e.g., Mignone, F. et al., Untranslated regions of mRNAs. Genome Biology, 3(3): reviews0004.1-0004.10 (2002)), incorporated herein by reference in its entirety. Any suitable leader sequences, with the above mentioned characteristics, can be used in practicing the present invention.

One useful embodiment of the inventive hybrid promoter is a promoter that comprises a nucleotide sequence at least 95%, at least 96%, at least 97%, at least 98%, at least 99%, or 100% identical to the nucleotide sequence of SEQ ID NO:1, following, which contains mCMV GenBank: L06816.1, nucleotides 4067-4682, Rat EF-1alpha intron Genbank: AC158987.3, nucleotides 22137-21728; and an intervening first leader sequence underlined in lower case letters (SEQ ID NO:3); and a second leader sequence underlined in italic lower case letters (SEQ ID NO:5):

Examples of additional useful embodiments of the inventive hybrid promoter include (i) SEQ ID NO:30 (hybrid promoter sequence including TetO, as in pJV57), (ii) SEQ ID NO:31 (hybrid promoter including a mCMV enhancer element with optimized hCMV promoter sequence, as in pJV59), and (iii) SEQ ID NO:32 (hybrid promoter including mCMV enhancer element with optimized hCMV promoter sequence and optimized TetO sequence, as in pJV60):

```
                                         SEQ ID NO: 1
GTCAACAGGAAAGTTCCATTGGAGCCAAGTACATTGAGTCAAT
AGGGACTTTCCAATGGGTTTTGCCCAGTACATAAGGTCAATGG
GAGGTAAGCCAATGGGTTTTTCCCATTACTGGCACGTATACTG
AGTCATTAGGGACTTTCCAATGGGTTTTGCCCAGTACATAAGG
TCAATAGGGGTGAATCAACAGGAAAGTCCCATTGGAGCCAAGT
ACACTGAGTCAATAGGGACTTTCCATTGGGTTTTGCCCAGTAC
AAAAGGTCAATAGGGGGTGAGTCAATGGGTTTTTCCCATTATT
GGCACGTACATAAGGTCAATAGGGGTGAGTCATTGGGTTTTTC
CAGCCAATTTAATTAAAACGCCATGTACTTTCCCACCATTGAC
GTCAATGGGCTATTGAAACTAATGCAACGTGACCTTTAAACGG
TACTTTCCCATAGCTGATTAATGGGAAAGTACCGTTCTCGAGC
CAATACACGTCAATGGGAAGTGAAAGGGCAGCCAAAACGTAAC
ACCGCCCCGGTTTTCCCCTGGAAATTCCATATTGGCACGCATT
CTATTGGCTGAGCTGCGTTCTACGTGGGTATAAGAGGCGCGAC
CAGCGTCGGTACCGtacctcttccgcatcgctgtctgcgaggg
ccagctgttgggGTGAGTGGCGGGTGTGGCTTCCGCGGGCCCC
GGAGCTGGAGCCCTGCTCTGAGCGGGCCGGGCTGATATGCGAG
TGTCGTCCGCAGGGTTTAGCTGTGAGCATTCCCACTTCGAGTG
GCGGGCGGTGCGGGGGTGAGAGTGCGAGGCCTAGCGGCAACCC
CGTAGCCTCGCCTCGTGTCCGGCTTGAGGCCTAGCGTGGTGTC
CGCCGCCGCGTGCCACTCCGGCCGCACTATGCGTTTTTTGTCC
TTGCTGCCCTCGATTGCCTTCCAGCAGCATGGGCTAACAAAGG
GAGGGTGTGGGGCTCACTCTTAAGGAGCCCATGAAGCTTACGT
TGGATAGGAATGGAAGGGCAGGAGGGGCGACTGGGGCCCGCCC
GCCTTCGGAGCACATGTCCGACGCCACCTGGATGGGGCGAGGC
CTGTGGCTTTCCGAAGCAATCGGGCGTGAGTTTAGCCTACCTG
GGCCATGTGGCCCTAGCACTGGGCACGGTCTGGCCTGGCGGTG
CCGCGTTCCCTTGCCTCCCAACAAGGGTGAGGCCGTCCCGCCC
GGCACCAGTTGCTTGCGCGGAAAGATGGCCGCTCCCGGGCCC
TGTTGCAAGGAGCTCAAAATGGAGGACGCGGCAGCCCGGTGGA
GCGGGCGGGTGAGTCACCCACACAAAGGAAGAGGGCCTTGCCC
CTCGCCGGCCGCTGCTTCCTGTGACCCCGTGGTCTATCGGCCG
CATAGTCACCTCGGGCTTCTCTTGAGCACCGCTCGTCGCGGCG
GGGGGAGGGGATCTAATGGCGTTGGAGTTTGTTCACATTTGGT
GGGTGGAGACTAGTCAGGCCAGCCTGGCGCTGGAAGTCATTCT
TGGAATTTGCCCCTTTGAGTTTGGAGCGAGGCTAATTCTCAAG
CCTCTTAGCGGTTCAAAGGTATTTTCTAAACCCGTTTCCAGct
cgcgttgaggacaaactcttcgcggtctttccagtactcttgg
atcggaaacccgtcggcctccgaacggtactccgccaccgagg
gacctgagcgagtccgcatcgaccggatcggaaaacctc//.
```

```
                                        SEQ ID NO: 30
GTCAACAGGAAAGTTCCATTGGAGCCAAGTACATTGAGTCAAT
AGGGACTTTCCAATGGGTTTTGCCCAGTACATAAGGTCAATGG
GAGGTAAGCCAATGGGTTTTTCCCATTACTGGCACGTATACTG
AGTCATTAGGGACTTTCCAATGGGTTTTGCCCAGTACATAAGG
TCAATAGGGGTGAATCAACAGGAAAGTCCCATTGGAGCCAAGT
ACACTGAGTCAATAGGGACTTTCCATTGGGTTTTGCCCAGTAC
AAAAGGTCAATAGGGGGTGAGTCAATGGGTTTTTCCCATTATT
GGCACGTACATAAGGTCAATAGGGGTGAGTCATTGGGTTTTTC
CAGCCAATTTAATTAAAACGCCATGTACTTTCCCACCATTGAC
GTCAATGGGCTATTGAAACTAATGCAACGTGACCTTTAAACGG
TACTTTCCCATAGCTGATTAATGGGAAAGTACCGTTCTCGAGC
CAATACACGTCAATGGGAAGTGAAAGGGCAGCCAAAACGTAAC
ACCGCCCCGGTTTTCCCCTGGAAATTCCATATTGGCACGCATT
CTATTGGCTGAGCTGCGTTCTACGTGGGTATATAAGCAGAGCT
CTCCCTATCAGTGATAGAGATCTCCCTATCAGTGATAGAGATC
GTCGACGAGCTCAGCGTCGGTACCGTACCTCTTCCGCATCGCT
GTCTGCGAGGGCAGCTGTTGGGGTGAGTGGCGGGTGTGGCTT
CCGCGGGCCCCGGAGCTGGAGCCCTGCTCTGAGCGGGCCGGGC
TGATATGCGAGTGTCGTCCGCAGGGTTTAGCTGTGAGCATTCC
CACTTCGAGTGGCGGGCGGTGCGGGGGTGAGAGTGCGAGGCCT
AGCGGCAACCCCGTAGCCTCGCCTCGTGTCCGGCTTGAGGCCT
AGCGTGGTGTCCGCCGCCGCGTGCCACTCCGGCCGCACTATGC
GTTTTTTGTCCTTGCTGCCCTCGATTGCCTTCCAGCAGCATGG
GCTAACAAAGGGAGGGTGTGGGGCTCACTCTTAAGGAGCCCAT
GAAGCTTACGTTGGATAGGAATGGAAGGGCAGGAGGGGCGACT
GGGGCCCGCCCGCCTTCGGAGCACATGTCCGACGCCACCTGGA
TGGGGCGAGGCCTGTGGCTTTCCGAAGCAATCGGGCGTGAGTT
TAGCCTACCTGGGCCATGTGGCCCTAGCACTGGGCACGGTCTG
GCCTGGCGGTGCCGCGTTCCCTTGCCTCCCAACAAGGGTGAGG
CCGTCCCGCCCGGCACCAGTTGCTTGCGCGGAAAGATGGCCGC
TCCCGGGCCCTGTTGCAAGGAGCTCAAAATGGAGGACGCGGC
AGCCCGGTGGAGCGGGCGGGTGAGTCACCCACACAAAGGAAGA
GGGCCTTGCCCCTCGCCGGCCGCTGCTTCCTGTGACCCCGTGG
TCTATCGGCCGCATAGTCACCTCGGGCTTCTCTTGAGCACCGC
TCGTCGCGGCGGGGGGAGGGGATCTAATGGCGTTGGAGTTTGT
```

```
TCACATTTGGTGGGTGGAGACTAGTCAGGCCAGCCTGGCGCTG
GAAGTCATTCTTGGAATTTGCCCCTTTGAGTTTGGAGCGAGGC
TAATTCTCAAGCCTCTTAGCGGTTCAAAGGTATTTTCTAAACC
CGTTTCCAGCTCGCGGTTGAGGACAAACTCTTCGCGGTCTTTC
CAGTACTCTTGGATCGGAAACCCGTCGGCCTCCGAACGGTACT
CCGCCACCGAGGGACCTGAGCGAGTCCGCATCGACCGGATCGG
AAAACCTC//;

SEQ ID NO: 31
GTCAACAGGAAAGTTCCATTGGAGCCAAGTACATTGAGTCAAT
AGGGACTTTCCAATGGGTTTTGCCCAGTACATAAGGTCAATGG
GAGGTAAGCCAATGGGTTTTTCCCATTACTGGCACGTATACTG
AGTCATTAGGGACTTTCCAATGGGTTTTGCCCAGTACATAAGG
TCAATAGGGGTGAATCAACAGGAAAGTCCCATTGGAGCCAAGT
ACACTGAGTCAATAGGGACTTTCCATTGGGTTTTGCCCAGTAC
AAAAGGTCAATAGGGGGTGAGTCAATGGGTTTTTCCCATTATT
GGCACGTACATAAGGTCAATAGGGGTGAGTCATTGGGTTTTTC
CAGCCAATTTAATTAAAACGCCATGTACTTTCCCACCATTGAC
GTCAATGGGCTATTGAAACTAATGCAACGTGACCTTTAAACGG
TACTTTCCCATAGCTGATTAATGGGAAAGTACCGTTCTCGAGC
CAATACACGTCAATGGGAAGTGAAAGGGCAGCCAAAACGTAAC
ACCGCCCCGGTTTTCCCCTGGAAATTCCATATTGGCACGCATT
CTATTGGCTGAGCTGCGTTCTACGTGGGTATATAAGCAGAGCT
CGTTTAGTGAACCGTCAGTTCGTCTCTAGACGCCAACCGCCTC
TTCCGCATCGCTGTCTGCGAGGGCCAGCTGTTGGGGTGAGTGG
CGGGTGTGGCTTCCGCGGGCCCCGGAGCTGGAGCCCTGCTCTG
AGCGGGCCGGGCTGATATGCGAGTGTCGTCCGCAGGGTTTAGC
TGTGAGCATTCCCACTTCGAGTGGCGGGCGGTGCGGGGGTGAG
AGTGCGAGGCCTAGCGGCAACCCCGTAGCCTCGCCTCGTGTCC
GGCTTGAGGCCTAGCGTGGTGTCCGCCGCCGCGTGCCACTCCG
GCCGCACTATGCGTTTTTTGTCCTTGCTGCCCTCGATTGCCTT
CCAGCAGCATGGGCTAACAAAGGGAGGGTGTGGGGCTCACTCT
TAAGGAGCCCATGAAGCTTACGTTGGATAGGAATGGAAGGGCA
GGAGGGGCGACTGGGGCCCGCCCGCCTTCGGAGCACATGTCCG
ACGCCACCTGGATGGGCGAGGCCTGTGGCTTTCCGAAGCAAT
CGGGCGTGAGTTTAGCCTACCTGGGCCATGTGGCCCTAGCACT
GGGCACGGTCTGGCCTGGCGGTGCCGCGTTCCCTTGCCTCCCA
ACAAGGGTGAGGCCGTCCCGCCCGGCACCAGTTGCTTGCGCGG
AAAGATGGCCGCTCCCGGGGCCCTGTTGCAAGGAGCTCAAAAT
GGAGGACGCGGCAGCCCGGTGGAGCGGGCGGGTGAGTCACCCA
CACAAAGGAAGAGGGCCTTGCCCCTCGCCGGCCGCTGCTTCCT
GTGACCCCGTGGTCTATCGGCCGCATAGTCACCTCGGGCTTCT
```

```
CTTGAGCACCGCTCGTCGCGGCGGGGGGAGGGGATCTAATGGC
GTTGGAGTTTGTTCACATTTGGTGGGTGGAGACTAGTCAGGCC
AGCCTGGCGCTGGAAGTCATTCTTGGAATTTGCCCCTTTGAGT
TTGGAGCGAGGCTAATTCTCAAGCCTCTTAGCGGTTCAAAGGT
ATTTTCTAAACCCGTTTCCAGCTCGCGGTTGAGGACAAACTCT
TCGCGGTCTTTCCAGTACTCTTGGATCGGAAACCCGTCGGCCT
CCGAACGGTACTCCGCCACCGAGGGACCTGAGCGAGTCCGCAT
CGACCGGATCGGAAAACCTC//;
and
                                  SEQ ID NO: 32
GTCAACAGGAAAGTTCCATTGGAGCCAAGTACATTGAGTCAAT
AGGGACTTTCCAATGGGTTTTGCCCAGTACATAAGGTCAATGG
GAGGTAAGCCAATGGGTTTTTCCCATTACTGGCACGTATACTG
AGTCATTAGGGACTTTCCAATGGGTTTTGCCCAGTACATAAGG
TCAATAGGGGTGAATCAACAGGAAAGTCCCATTGGAGCCAAGT
ACACTGAGTCAATAGGGACTTTCCATTGGGTTTTGCCCAGTAC
AAAAGGTCAATAGGGGGTGAGTCAATGGGTTTTTCCCATTATT
GGCACGTACATAAGGTCAATAGGGGTGAGTCATTGGGTTTTTC
CAGCCAATTTAATTAAAACGCCATGTACTTTCCCACCATTGAC
GTCAATGGGCTATTGAAACTAATGCAACGTGACCTTTAAACGG
TACTTTCCCATAGCTGATTAATGGGAAAGTACCGTTCTCGAGC
CAATACACGTCAATGGGAAGTGAAAGGGCAGCCAAAACGTAAC
ACCGCCCCGGTTTTCCCCTGGAAATTCCATATTGGCACGCATT
CTATTGGCTGAGCTGCGTTCTACGTGGGTATATAAGCAGAGCT
CTCCCTATCAGTGATCAGTTCCTCCCTATCAGTGATAGAGATC
GTCGACGAGCTCAGCGTCGGTACCGTACCTCTTCCGCATCGCT
GTCTGCGAGGGCCAGCTGTTGGGGTGAGTGGCGGGTGTGGCTT
CCGCGGGCCCCGGAGCTGGAGCCCTGCTCTGAGCGGGCCGGGC
TGATATGCGAGTGTCGTCCGCAGGGTTTAGCTGTGAGCATTCC
CACTTCGAGTGGCGGGCGGTGCGGGGTGAGAGTGCGAGGCCT
AGCGGCAACCCCGTAGCCTCGCCTCGTGTCCGGCTTGAGGCCT
AGCGTGGTGTCCGCCGCCGCGTGCCACTCCGGCCGCACTATGC
GTTTTTTGTCCTTGCTGCCCTCGATTGCCTTCCAGCAGCATGG
GCTAACAAAGGGAGGGTGTGGGGCTCACTCTTAAGGAGCCCAT
GAAGCTTACGTTGGATAGGAATGGAAGGGCAGGAGGGGCGACT
GGGGCCCGCCCGCCTTCGGAGCACATGTCCGACGCCACCTGGA
TGGGGCGAGGCCTGTGGCTTTCCGAAGCAATCGGGCGTGAGTT
TAGCCTACCTGGGCCATGTGGCCCTAGCACTGGGCACGGTCTG
GCCTGGCGGTGCCGCGTTCCCTTGCCTCCCAACAAGGGTGAGG
CCGTCCCGCCCGGCACCAGTTGCTTGCGCGGAAAGATGGCCGC
TCCCGGGGCCCTGTTGCAAGGAGCTCAAAATGGAGGACGCGGC
```

```
                    -continued
AGCCCGGTGGAGCGGGCGGGTGAGTCACCCACACAAAGGAAGA

GGGCCTTGCCCCTCGCCGGCCGCTGCTTCCTGTGACCCCGTGG

TCTATCGGCCGCATAGTCACCTCGGGCTTCTCTTGAGCACCGC

TCGTCGCGGCGGGGGAGGGGATCTAATGGCGTTGGAGTTTGT

TCACATTTGGTGGGTGGAGACTAGTCAGGCCAGCCTGGCGCTG

GAAGTCATTCTTGGAATTTGCCCCTTTGAGTTTGGAGCGAGGC

TAATTCTCAAGCCTCTTAGCGGTTCAAAGGTATTTTCTAAACC

CGTTTCCAGCTCGCGGTTGAGGACAAACTCTTCGCGGTCTTTC

CAGTACTCTTGGATCGGAAACCCGTCGGCCTCCGAACGGTACT

CCGCCACCGAGGGACCTGAGCGAGTCCGCATCGACCGGATCGG

AAAACCTC//.
```

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques.

A "variant" of a polypeptide (e.g., an immunoglobulin, or an antibody) comprises an amino acid sequence wherein one or more amino acid residues are inserted into, deleted from and/or substituted into the amino acid sequence relative to another polypeptide sequence. Variants include fusion proteins.

The term "fusion protein" indicates that the protein includes polypeptide components derived from more than one parental protein or polypeptide. Typically, a fusion protein is expressed from a "fusion gene" in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments of the inventive method, the protein of interest can be synthesized by the host cell as a secreted protein, which can then be further purified from the extracellular space and/or medium.

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes, or, in vitro, is dissolved, or is capable of being dissolved in an aqueous buffer under physiological conditions without forming significant amounts of insoluble aggregates (i.e., forms aggregates less than 10%, and typically less than about 5%, of total protein) when it is suspended without other proteins in an aqueous buffer of interest under physiological conditions, such buffer not containing a detergent or chaotropic agent, such as urea, guanidinium hydrochloride, or lithium perchlorate. In contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc., or in an in vitro aqueous buffer under physiological conditions forms significant amounts of insoluble aggregates (i.e., forms aggregates equal to or more than about 10% of total protein) when it is suspended without other proteins (at physiologically compatible temperature) in an aqueous buffer of interest under physiological conditions, such buffer not containing a detergent or chaotropic agent, such as urea, guanidinium hydrochloride, or lithium perchlorate.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the immunoglobulin (e.g., antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

The present invention relates to an expression cassette that includes the inventive hybrid promoter. A eukaryotic "expression cassette" refers to the part of an expression vector that enables production of protein in a eukaryotic cell, such as a mammalian cell. It includes a promoter, operable in a eukaryotic cell, for mRNA transcription, one or more gene(s) encoding protein(s) of interest and a mRNA termination and processing signal. An expression cassette can usefully include among the coding sequences, a gene useful as a selective marker. In the expression cassette of the present invention, the hybrid promoter (or control sequence) is operably linked 5' to an open reading frame encoding an exogenous protein of interest; and a polyadenylation site is operably linked 3' to the open reading frame. The protein of interest encoded by the open reading frame can be a monomeric protein or fusion protein, or it can be a subunit of a larger multimeric protein. The protein of interest expressed from a second or third expression cassette can be different or the same as the protein of interest encoded by the open reading frame of the first expression cassette; for example, a first expression cassette can include the coding sequence for a light chain subunit of an immunoglobulin, and a second or third expression cassette in the expression vector can include the coding sequence for the immunoglobulin heavy chain subunit, or vice versa, with each of the subunits being the "protein of interest" with respect to the expression cassette in which its coding sequence is included. One embodiment of a useful polyadenylation site sequence is a SV40 late polyadenylation site SEQ ID NO:14:

```
                                            SEQ ID NO: 14
    CACACATCATAAGATACATTGATGAGTTTGGACAAACCACAAC

TAGAATGCAGTGAAAAAAATGCTTTATTTGTGAAATTTGTGAT

GCTATTGCTTTATTTGTAACCATTATAAGCTGCAATAAACAAG

TTAACAACAACAATTGCATTCATTTTATGTTTCAGGTTCAGGG

GGAGATGTGGGAGGTTTTTTAAAGCAAGTAAAACCTCTACAA

ATGTGGTA//.
```

Other suitable control sequences can also be included as long as the expression cassette remains operable. The open reading frame can optionally include a coding sequence for more than one protein of interest.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The present invention also encompasses a recombinant expression vector comprising the inventive expression cassette.

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., Protein expression vector and utilization thereof, U.S. Pat. No. 7,029,909; Ruben et al., 27 human secreted proteins, US 2003/0104400 A1). For expression of multi-subunit proteins of interest, separate expression vectors in suitable numbers and proportions, each containing a coding sequence for each of the different monomers, can be used to transform a host cell. In other embodiments a single expression vector can be used to express the different subunits of the protein of interest.

The present invention also relates to a mammalian host cell comprising the inventive recombinant expression vector.

The term "host cell" means a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

Examples of useful mammalian host cell lines are Chinese hamster ovary cells, including CHO-K1 cells (e.g., ATCC CCL61), DXB-11, DG-44, and Chinese hamster ovary cells/-DHFR (CHO, Urlaub et al, Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al, J. Gen Virol. 36: 59 (1977)]; baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al, Annals N.Y Acad. Sci. 383: 44-68 (1982)); MRC 5 cells or FS4 cells; or mammalian myeloma cells.

"Cell," "cell line," and "cell culture" are often used interchangeably and all such designations herein include cellular progeny. For example, a cell "derived" from a CHO cell is a cellular progeny of a Chinese Hamster Ovary cell, which may be removed from the original primary cell parent by any number of generations, and which can also include a transformant progeny cell. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Host cells are transformed or transfected with the above-described nucleic acids or vectors for production of polypeptides (including antigen binding proteins, such as antibodies) and are cultured in conventional nutrient medium modified as appropriate for inducing promoters, selecting transformants, or amplifying the genes encoding the desired sequences. In addition, novel vectors and transfected cell lines with multiple copies of transcription units separated by a selective marker are particularly useful for the expression of polypeptides, such as antibodies.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The present invention also relates to a method of producing a protein of interest involving culturing the mammalian host cell, in aqueous medium under physiological conditions permitting expression of the protein of interest; and recovering the protein of interest from the medium.

The host cells used to produce the polypeptides useful in the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source, such that the physiological conditions of the cell in, or on, the medium promote expression of the protein of interest by the host cell; any other necessary supplements may also be included at appropriate concentrations that would be known to those skilled in the art. The culture conditions, such as temperature (typically, but not necessarily, about 37° C.), pH (typically, but not necessarily, about pH 6.5-7.5), oxygenation, and the like, are those previously used with the host cell selected for expression of the protein of interest, and will be apparent to the ordinarily skilled artisan. The culture medium can include a suitable amount of serum such a fetal bovine serum (FBS), or preferably, the host cells can be adapted for culture in serum-free medium. In some embodiments, the aqueous medium is liquid, such that the host cells are cultured in a cell suspension within the liquid medium. The host cells can be usefully grown in batch culture or in continuous culture systems.

In other embodiments, the mammalian host cells can be cultured on solid or semisolid aqueous medium, for example, containing agar or agarose, to form a medium or substrate surface to which the cells adhere and form an adhesion layer.

Upon culturing the host cells, the recombinant polypeptide can be produced intracellularly, in the periplasmic space, or directly secreted into the medium. If the polypeptide, such as an antigen binding protein (e.g., an antibody), is produced intracellularly, as a first step, the particulate debris, either host cells or lysed fragments, is removed, for example, by centrifugation or ultrafiltration.

A protein of interest, such as an antibody or antibody fragment can be purified using, for example, hydroxylapatite chromatography, cation or anion exchange chromatography, or preferably affinity chromatography, using the antigen of interest or protein A or protein G as an affinity ligand. Protein A can be used to purify proteins that include polypeptides are based on human γ1, γ2, or γ4 heavy chains (Lindmark et al., J. Immunol. Meth. 62: 1-13 (1983)). Protein G is recommended for all mouse isotypes and for human γ3 (Guss et al, EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a CH 3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

"Under physiological conditions" with respect to incubating buffers and immunoglobulins, or other binding assay reagents means incubation under conditions of temperature, pH, and ionic strength, that permit a biochemical reaction, such as a non-covalent binding reaction, to occur. Typically, the temperature is at room or ambient temperature up to about 37° C. and at pH 6.5-7.5.

"Physiologically acceptable salt" of a composition of matter, for example a salt of an immunoglobulin, such as an antibody, or other protein of interest, means any salt, or salts, that are known or later discovered to be pharmaceutically acceptable. Some non-limiting examples of pharmaceutically acceptable salts are: acetate; trifluoroacetate; hydrohalides, such as hydrochloride and hydrobromide; sulfate; citrate; maleate; tartrate; glycolate; gluconate; succinate; mesylate; besylate; salts of gallic acid esters (gallic acid is also known as 3,4, 5 trihydroxybenzoic acid) such as PentaGalloylGlucose (PGG) and epigallocatechin gallate (EGCG), salts of cholesteryl sulfate, pamoate, tannate and oxalate salts.

A "reaction mixture" is an aqueous mixture containing all the reagents and factors necessary, which under physiological conditions of incubation, permit an in vitro biochemical reaction of interest to occur, such as a covalent or non-covalent binding reaction.

A "domain" or "region" (used interchangeably herein) of a polynucleotide is any portion of the entire polynucleotide, up to and including the complete polynucleotide, but typically comprising less than the complete polynucleotide. A domain can, but need not, fold independently (e.g., DNA hairpin folding) of the rest of the polynucleotide chain and/or be correlated with a particular biological, biochemical, or structural function or location, such as a coding region or a regulatory region.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')$_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

An "isolated" protein, e.g., an immunoglobulin, such as an antibody or antibody fragment, is one that has been identified and separated from one or more components of its natural environment or of a culture medium in which it has been secreted by a producing cell. In some embodiments, the isolated protein is substantially free from proteins or polypeptides or other contaminants that are found in its natural or culture medium environment that would interfere with its therapeutic, diagnostic, prophylactic, research or other use. "Contaminant" components of its natural environment or medium are materials that would interfere with diagnostic or therapeutic uses for the protein, e.g., an antibody, and may include enzymes, hormones, and other proteinaceous or nonproteinaceous (e.g., polynucleotides, lipids, carbohydrates) solutes. Typically, an "isolated protein" constitutes at least about 5%, at least about 10%, at least about 25%, or at least about 50% of a given sample. In some embodiments, the protein of interest, e.g., an antibody will be purified (1) to greater than 95% by weight of protein, and most preferably more than 99% by weight, or (2) to homogeneity by SDS-PAGE under reducing or nonreducing conditions, optionally using a stain, e.g., Coomassie blue or silver stain. Isolated naturally occurring antibody includes the antibody in situ within recombinant cells since at least one component of the protein's natural environment will not be present. Typically, however, the isolated protein of interest (e.g., an antibody) will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies that are antigen binding proteins are highly specific binders, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab, Fab', F(ab)$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 [1991] and Marks et al., J. Mol. Biol., 222:581-597 (1991), for example.

A "multispecific" binding agent or antigen binding protein or antibody is one that targets more than one antigen or epitope.

A "bispecific," "dual-specific" or "bifunctional" binding agent or antigen binding protein or antibody is a hybrid having two different antigen binding sites. Biantigen binding proteins, antigen binding proteins and antibodies are a species of multiantigen binding protein, antigen binding protein or multispecific antibody and may be produced by a variety of methods including, but not limited to, fusion of hybridomas or linking of Fab' fragments. (See, e.g., Songsivilai and Lachmann, 1990, Clin. Exp. Immunol. 79:315-321; Kostelny et al., 1992, J. Immunol. 148:1547-1553; Spiess et al., Alternative molecular formats and therapeutic applications for bispecific antibodies, Mol. Immunol. 67:95-106 (2015)). The two binding sites of a bispecific antigen binding protein or antibody will bind to two different epitopes, which may reside on the same or different protein targets.

The term "immunoglobulin" encompasses full antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody"). An "immunoglobulin" is a protein, but is not necessarily an antigen binding protein.

In an "antibody", each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen in the case of an antibody that is an antigen binding protein. However, within the scope of the present invention, an embodiment of the immunoglobulin, e.g., an antibody, need not be an antigen binding protein, or need not be known to specifically bind to an antigen. The variable domain residues between the hypervariable regions are called the framework residues and generally are somewhat homologous among different antibodies. Immunoglobulins can be assigned to different classes depending on the amino acid sequence of the constant domain of their heavy chains. Human light chains are classified as kappa (.kappa.) and lambda (.lamda.) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). Within the scope of the invention, an "antibody" also encompasses a recombinantly made antibody, and antibodies that are glycosylated or lacking glycosylation.

The term "light chain" or "immunoglobulin light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_H$ domains are at the carboxyl-terminus, with the $C_{H3}$ being closest to the carboxy-terminus of the polypeptide. Heavy chains are classified as mu (μ), delta (δ), gamma (γ), alpha (α), and epsilon (ε), and define the antibody's isotype as IgM, IgD, IgG, IgA, and IgE, respectively. In separate embodiments of the invention, heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA1 and IgA2. Different IgG isotypes may have different effector functions (mediated by the Fc region), such as antibody-dependent cellular cytotoxicity (ADCC) and complement-dependent cytotoxicity (CDC). In ADCC, the Fc region of an antibody binds to Fc receptors (Fc.gamma.Rs) on the surface of immune effector cells such as natural killers and macrophages, leading to the phagocytosis or lysis of the targeted cells. In CDC, the antibodies kill the targeted cells by triggering the complement cascade at the cell surface.

An "Fc region", or used interchangeably herein, "Fc domain" or "immunoglobulin Fc domain", contains two heavy chain fragments, which in a full antibody comprise the $C_{H1}$ and $C_{H2}$ domains of the antibody. The two heavy chain fragments are held together by two or more disulfide bonds and by hydrophobic interactions of the $C_{H3}$ domains.

The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

In many embodiments of the invention, the protein of interest is an antigen binding protein, such as but not limited to, an antibody, antibody subunit, or antibody fragment. For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, th Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or "FR" residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')$_2$, and Fv fragments; diabodies; linear antibodies (Zapata et al., Protein Eng., 8(10): 1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')$_2$ fragment that has two "Single-chain Fv" or "scFv" antibody fragments comprising the $V_H$ and $V_L$ domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 1 13, Rosenburg and Moore eds., Springer-Verlag, New York, pp. 269-315 (1994).

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and a portion of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. A single variable domain (or half of an Fv comprising only three CDRs specific for an antigen) has the ability to recognize and bind antigen, although at a lower affinity than the entire binding site.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference in their entireties.

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science 242:423-426, 1988, and Huston et al., Proc. Natl. Acad. Sci. USA 85:5879-5883, 1988). An "Fd" fragment consists of the $V_H$ and $C_{H1}$ domains.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "antigen binding protein" (ABP) includes antibodies or antibody fragments, as defined above, and recombinant peptides or other compounds that contain sequences derived from CDRs having the desired antigen-binding properties such that they specifically bind a target antigen of interest.

In general, an antigen binding protein, e.g., an antibody or antibody fragment, "specifically binds" to an antigen of interest when it has a significantly higher binding affinity for, and consequently is capable of distinguishing, that antigen, compared to its affinity for other unrelated proteins, under similar binding assay conditions. Typically, an antigen binding protein is said to "specifically bind" its target antigen when the dissociation constant ($K_D$) is $10^{-8}$ M or lower. The antigen binding protein specifically binds antigen with "high affinity" when the $K_D$ is $10^{-9}$ M or lower, and with "very high affinity" when the $K_D$ is $10^{-10}$ M or lower.

"Antigen binding region" or "antigen binding site" means a portion of a protein that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions ("FRs"). A "CDR" is an amino acid sequence that contributes to antigen binding specificity and affinity. "Framework" regions can aid in maintaining the proper conformation of the CDRs to promote binding between the antigen binding region and an antigen. In a traditional antibody, the CDRs are embedded within a framework in the heavy and light chain variable region where they constitute the regions responsible for antigen binding and recognition. A variable region of an immunoglobulin antigen binding protein comprises at least three heavy or light chain CDRs, see, supra (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991, supra; see also Chothia and Lesk, 1987, supra).

The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., in a single-chain polypeptide, amino acid residues that are not contiguous to one another in the polypeptide sequence but that within the context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The term "modification" when used in connection with proteins of interest (e.g., immunoglobulins, including antibodies and antibody fragments), include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. Modified immunoglobulins of the invention will retain the binding (or non-binding) properties of unmodified molecules of the invention. By methods known to the skilled artisan, immunoglobulins, such as antibodies, or other proteins, can be "engineered" or modified for improved target affinity, selectivity, stability, and/or manufacturability before the coding sequence of the "engineered" protein is included in the inventive expression cassette.

The term "derivative" when used in connection with proteins of interest, such as immunoglobulins (including antibodies and antibody fragments) refers to proteins that are covalently modified by conjugation to therapeutic or diagnostic agents, labeling (e.g., with radionuclides or various enzymes), covalent polymer attachment such as PEGylation (derivatization with polyethylene glycol) and insertion or substitution by chemical synthesis of non-natural amino acids. Derivatives of the invention will retain the binding properties of un-derivatized molecules.

Within the scope of the invention, proteins of interest can be therapeutic proteins (so-called "biologics.") The term "therapeutic protein" means a pharmacologically active protein applicable to the prevention, treatment, or cure of a disease, disorder, or medical condition of human beings or other mammals. Examples of therapeutic proteins include, but are not limited to, monoclonal antibodies, recombinant forms of a native protein (e.g., a receptor, ligand, hormone, enzyme or cytokine), fusion proteins, peptibodies, and/or a monomer domain binding proteins, e.g., based on a domain selected from LDL receptor A-domain, thrombospondin domain, thyroglobulin domain, trefoil/PD domain, VEGF binding domain, EGF domain, Anato domain, Notch/LNR domain, DSL domain, integrin beta domain, and Ca-EGF domain. The preceding are merely exemplary, and a therapeutic protein can comprise any clinically relevant polypeptide target moiety or polypeptide ligand.

"Treatment" or "treating" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. "Treatment" includes any indication(s) of success in the amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination by a physician or other health care provider, self-reporting by a patient, neuropsychiatric exams, and/or a psychiatric evaluation.

An "effective amount" of a therapeutic is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with migraine headache. In some embodiments, the effective amount is a therapeutically effective amount or a prophylactically effective amount. A "therapeutically effective amount" is an amount sufficient to remedy a disease state (e.g., transplant rejection or GVHD, inflammation, multiple sclerosis, cancer, cardiovascular disease, diabetes, neuropathy, pain) or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of a pharmaceutical composition that, when administered to a subject, will have the intended prophylactic effect, e.g., preventing or delaying the onset (or reoccurrence) of migraine headache or multiple sclerosis symptoms, or reducing the likelihood of the onset (or reoccurrence) of migraine headache, migraine headache symptoms, or multiple sclerosis symptoms. The full therapeutic or prophylactic effect does not necessarily occur by administration of one dose, and may occur only after administration of a series of doses. Thus, a therapeutically or prophylactically effective amount may be administered in one or more administrations.

The protein of interest can be any protein, but in in many embodiments the protein is a pharmacologically active protein or peptide.

In some embodiments of the invention, the protein of interest can be a mimetic or agonist peptide. The terms "-mimetic peptide," "peptide mimetic," and "-agonist peptide" refer to a peptide or protein having biological activity comparable to a naturally occurring protein of interest. These terms further include peptides that indirectly mimic the activity of a naturally occurring peptide molecule, such as by potentiating the effects of the naturally occurring molecule.

In some embodiments of the invention, the protein of interest can be an antagonist peptide or inhibitor peptide. The term "-antagonist peptide," "peptide antagonist," and "inhibitor peptide" refer to a peptide that blocks or in some way interferes with the biological activity of a receptor of interest, or has biological activity comparable to a known antagonist or inhibitor of a receptor of interest (such as, but not limited to, an ion channel or a G-Protein Coupled Receptor (GPCR)).

Examples of pharmacologically active proteins that can be used within the present invention include, but are not limited to, a toxin peptide, an IL-6 binding peptide, a CD3 binding protein, a CD19 binding protein, a CD20 binding protein, a CD22 binding protein, a HER2 binding protein, a HER5 binding protein, a VEGF-A binding protein, a TNF-α binding protein, an EGFR binding protein, a RANK ligand binding protein, an IL-1α binding protein, an IL-1β binding protein, an IL-17A binding protein, an EPCAM (CD326) binding protein, a CGRP peptide antagonist, a bradykinin B1 receptor peptide antagonist, a parathyroid hormone (PTH) agonist peptide, a parathyroid hormone (PTH) antagonist peptide, an ang-1 binding peptide, an ang-2 binding peptide, a myostatin binding peptide, an erythropoietin-mimetic (EPO-mimetic) peptide, a FGF21 peptide, a thrombopoietin-mimetic (TPO-mimetic) peptide (e.g., AMP2 or AMP5), a nerve growth factor (NGF) binding peptide, a B cell activating factor (BAFF) binding peptide, and a glucagon-like peptide (GLP)-1 or a peptide mimetic thereof or GLP-2 or a peptide mimetic thereof.

The term peptide or protein "analog" refers to a polypeptide having a sequence that differs from a peptide sequence existing in nature by at least one amino acid residue substitution, internal addition, or internal deletion of at least one amino acid, and/or amino- or carboxy-terminal end truncations, or additions). An "internal deletion" refers to absence of an amino acid from a sequence existing in nature at a position other than the N- or C-terminus. Likewise, an "internal addition" refers to presence of an amino acid in a sequence existing in nature at a position other than the N- or C-terminus.

Cloning DNA

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody; e.g., ATGGACATGAGGGTGCCCGCTCAGCTCCTGG GGCTCCTGCTGCTGTGGCTGAGAG GT GCGCGCTGT//SEQ ID NO:7, which encodes the VK-1 signal peptide sequence MDMRVPAQLLGLLLLWLR-GARC//SEQ ID NO:8), an origin of replication, one or more selective marker genes (that may, for example, confer antibiotic or other drug resistance, complement auxotrophic deficiencies, or supply critical nutrients not available in the medium), an enhancer element, a promoter, and a transcription termination sequence, all of which are well known in the art.

By way of further illustration, the following numbered embodiments are encompassed by the present invention:

Embodiment 1: A hybrid promoter (or control sequence) comprising:
(i) a mCMV enhancer sequence, comprising a mCMV enhancer element (mCMV-E) and a CMV promoter (CMV-P) sequence at its 3' end, operably linked 5' to a rat EF-1alpha intron sequence;
(ii) an intervening first leader sequence operably linked, 3' to the CMV promoter sequence of the mCMV enhancer sequence, and 5' to the rat EF-1alpha intron sequence; and
(iii) a second leader sequence operably linked 3' to the rat EF-1alpha intron sequence.

Embodiment 2: The hybrid promoter of Embodiment 1, wherein the CMV promoter sequence at the 3' end of the mCMV enhancer sequence comprises a segment having the nucleotide sequence of SEQ ID NO:24 or SEQ ID NO:26.

Embodiment 3: The hybrid promoter of any of Embodiments 1-2, wherein the rat EF-1alpha intron sequence comprises the nucleotide sequence of SEQ ID NO:4.

Embodiment 4: The hybrid promoter of any of Embodiments 1-3, wherein the mCMV enhancer sequence comprises the nucleotide sequence of SEQ ID NO:2 or SEQ ID NO:33; and the rat EF-1alpha intron sequence comprises the nucleotide sequence of SEQ ID NO:4.

Embodiment 5: The hybrid promoter of any of Embodiments 1-4, wherein the first leader sequence comprises the nucleotide sequence of SEQ ID NO:3.

Embodiment 6: The hybrid promoter of any of Embodiments 1-5, wherein the second leader sequence comprises the nucleotide sequence of SEQ ID NO:5.

Embodiment 7: The hybrid promoter of any of Embodiments 1-6, further comprising one or more TetO sequences inserted within the CMV promoter sequence.

Embodiment 8: The hybrid promoter of any of Embodiments 1-7, comprising a nucleotide sequence having at least 95% sequence identity to the nucleotide sequence of any of SEQ ID NO:1, SEQ ID NO:30, SEQ ID NO:31, or SEQ ID NO:32.

Embodiment 9: An expression cassette, comprising:
the hybrid promoter (or control sequence) of any of Embodiments 1-8, operably linked 5' to an open reading frame encoding an exogenous protein of interest; and a polyadenylation site operably linked 3' to the open reading frame.

Embodiment 10: A recombinant expression vector comprising the expression cassette of Embodiment 9.

Embodiment 11: A mammalian host cell comprising the recombinant expression vector of Embodiment 10.

Embodiment 12: The mammalian host cell of Embodiment 11, further being capable of expressing TetR.

Embodiment 13: The mammalian host cell of any of Embodiments 11-12, being derived from a Chinese Hamster Ovary (CHO) cell.

Embodiment 14: The mammalian host cell of any of Embodiments 11-13, selected from the group consisting of a CHO-K1 cell, a DXB11 cell, and a DG44 cell.

Embodiment 15: A method of producing a protein of interest, comprising:
(a) culturing the mammalian host cell of any of Embodiments 11-14, in an aqueous medium under physiological conditions permitting expression of the protein of interest; and
(b) recovering the protein of interest from the medium.

Embodiment 16: A method of producing a protein of interest, comprising:
(a) culturing a mammalian host cell that comprises an expression vector comprising the hybrid promoter (or control sequence) of any of Embodiments 7-8, in an aqueous medium under physiological conditions, wherein the mammalian host cell is capable of expressing TetR, whereby, in the absence of tetracycline in the medium, the expression of the protein of interest is repressed;
(b) adding tetracycline to the aqueous medium in an amount sufficient to bind TetR in the host cell, whereby expression of the protein of interest by the host cell is derepressed; and
(c) recovering the protein of interest from the medium.

Embodiment 17: The method of any of Embodiments 15-16, wherein the aqueous medium is serum-free.

Embodiment 18: The method of any of Embodiments 15-16, wherein culturing the mammalian host cell is in a suspension in liquid aqueous medium.

Embodiment 19: The method of any of Embodiments 15-16, wherein culturing the mammalian host cell is in an adhesion layer on a solid or semisolid substrate.

Embodiment 20: A recombinant expression vector, comprising:
(a) a 5' PiggyBac ITR comprising the nucleotide sequence of SEQ ID NO:45;
(b) a first expression cassette, comprising:
(i) a control sequence comprising:
(1) a mCMV enhancer sequence, comprising a mCMV enhancer element (mCMV-E) and a CMV promoter (CMV-P) sequence at its 3' end, operably linked 5' to a rat EF-1alpha intron sequence;

(2) an intervening first leader sequence operably linked, 3' to the CMV-P sequence of the mCMV enhancer sequence, and 5' to the rat EF-1alpha intron sequence; and (3) a second leader sequence operably linked 3' to the rat EF-1alpha intron sequence;

(ii) an open reading frame encoding a protein of interest operably linked to the control sequence; and (iii) a polyadenylation site operably linked 3' to the open reading frame;

(c) a second expression cassette, comprising:

(i) a weak constitutive promoter, operably linked to an open reading frame encoding a selectable marker; and (ii) a polyadenylation site operably linked 3' to the open reading frame; and (d) a 3' PiggyBac ITR comprising the nucleotide sequence of SEQ ID NO:47.

Embodiment 21: The vector of Embodiment 20, further comprising:

(e) a third expression cassette comprising:

(i) a control sequence comprising a promoter;

(ii) an open reading frame encoding a protein of interest (different or the same as the protein of interest encoded by the open reading frame of the first expression cassette) operably linked to the control sequence; and (iii) a second polyadenylation site operably linked 3' to the open reading frame.

Embodiment 22: The vector of Embodiment 21, wherein the control sequence (i) of the third expression cassette comprises:

(1) a mCMV enhancer sequence, comprising a mCMV enhancer element (mCMV-E) and a CMV promoter (CMV-P) sequence at its 3' end, operably linked 5' to a rat EF-1alpha intron sequence;

(2) an intervening first leader sequence operably linked, 3' to the CMV-P sequence of the mCMV enhancer sequence, and 5' to the rat EF-1alpha intron sequence; and (3) a second leader sequence operably linked 3' to the rat EF-1alpha intron sequence.

Embodiment 23: The recombinant expression vector of any of Embodiments 20-22, wherein the weak constitutive promoter is a deleted SV40 promoter.

Embodiment 24: The recombinant expression vector of any of Embodiments 20-23, wherein the deleted SV40 promoter comprises the nucleotide sequence of SEQ ID NO:53.

Embodiment 25: The recombinant expression vector of any of Embodiments 20-24, wherein the deleted SV40 promoter comprises the nucleotide sequence of SEQ ID NO:46.

Embodiment 26: The recombinant expression vector of any of Embodiments 20-25, wherein the selectable marker is glutamine synthetase, puromycin resistance, neomycin resistance, zeomycin resistance, or dihydrofolate reductase.

Embodiment 27: The recombinant expression vector of any of Embodiments 20-26, wherein the selectable marker is glutamine synthetase.

Embodiment 28: The recombinant expression vector of any of Embodiments 20-27, wherein the selectable marker is encoded by the nucleotide sequence of SEQ ID NO:49, or a degenerate DNA sequence.

Embodiment 29: A recombinant expression vector, comprising:

(a) a first expression cassette, comprising:

(i) a control sequence comprising:

(1) a mCMV enhancer sequence, comprising a mCMV enhancer element (mCMV-E) and a CMV promoter (CMV-P) sequence at its 3' end, operably linked 5' to a rat EF-1alpha intron sequence;

(2) an intervening first leader sequence operably linked, 3' to the CMV-P sequence of the mCMV enhancer sequence, and 5' to the rat EF-1alpha intron sequence; and (3) a second leader sequence operably linked 3' to the rat EF-1alpha intron sequence;

(ii) an open reading frame encoding a first immunoglobulin subunit operably linked to the control sequence; and (iii) a first polyadenylation site operably linked 3' to the open reading frame;

(b) a second expression cassette 3' to the first expression cassette, comprising:

(i) a control sequence comprising a promoter;

(ii) an open reading frame encoding a second immunoglobulin subunit operably linked to the promoter; and (iii) a second polyadenylation site operably linked 3' to the open reading frame; and (c) a transcription termination sequence 3' to the first expression cassette and 5' to the second expression cassette.

Embodiment 30: The vector of Embodiment 29, wherein the control sequence (i) of the second expression cassette comprises:

(1) a mCMV enhancer sequence, comprising a mCMV enhancer element (mCMV-E) and a CMV promoter (CMV-P) sequence at its 3' end, operably linked 5' to a rat EF-1alpha intron sequence;

(2) an intervening first leader sequence operably linked, 3' to the CMV-P sequence of the mCMV enhancer sequence, and 5' to the rat EF-1alpha intron sequence; and (3) a second leader sequence operably linked 3' to the rat EF-1alpha intron sequence.

Embodiment 31: The vector of any of Embodiments 29-30, further comprising:

(d) a third expression cassette comprising:

(i) a weak constitutive promoter, operably linked to an open reading frame encoding a selectable marker; and (ii) a polyadenylation site operably linked 3' to the open reading frame.

Embodiment 32: The vector of Embodiment 31, wherein the weak constitutive promoter is a deleted SV40 promoter.

Embodiment 33: The vector of Embodiment 32, wherein the deleted SV40 promoter comprises the nucleotide sequence of SEQ ID NO:53.

Embodiment 34: The vector of any of Embodiments 32-33, wherein the deleted SV40 promoter comprises the nucleotide sequence of SEQ ID NO:46.

Embodiment 35: The vector of any of Embodiments 31-34, wherein the selectable marker is glutamine synthetase, puromycin resistance, neomycin resistance, zeomycin resistance, or dihydrofolate reductase.

Embodiment 36: The vector of any of Embodiments 31-35, wherein the selectable marker is glutamine synthetase.

Embodiment 37: The vector of any of Embodiments 31-36, wherein the selectable marker is encoded by the nucleotide sequence of SEQ ID NO:49, or a degenerate DNA sequence.

Embodiment 38: A mammalian host cell, comprising the recombinant expression vector of any of Embodiments 20-37.

Embodiment 39: The mammalian host cell of Embodiment 38, wherein the mammalian host cell is a CHO cell.

Embodiment 40: The mammalian host cell of Embodiment 39, wherein the CHO cell is a CHO-K1 cell, a DXB11 cell, or a DG44 cell.

Embodiment 41: A method of producing a protein of interest, in vitro, comprising culturing the mammalian host cell of any of Embodiments 38-40 in an aqueous medium under physiological conditions permitting expression of the protein of interest; and recovering the protein of interest from the medium.

Embodiment 42: A recombinant expression vector, comprising:
(a) a 5' PiggyBac ITR comprising the nucleotide sequence of SEQ ID NO:45;
(b) a first expression cassette, comprising:
  (i) a control sequence comprising:
    (1) a mCMV enhancer sequence, comprising a mCMV enhancer element (mCMV-E) and a CMV promoter (CMV-P) sequence at its 3' end, operably linked 5' to a rat EF-1alpha intron sequence, comprising one or more TetO sequences inserted within the CMV-P sequence;
    (2) an intervening first leader sequence operably linked, 3' to the CMV-P sequence of the mCMV enhancer sequence, and 5' to the rat EF-1alpha intron sequence; and
    (3) a second leader sequence operably linked 3' to the rat EF-1alpha intron sequence;
  (ii) an open reading frame encoding a protein of interest operably linked to the control sequence; and
  (iii) a polyadenylation site operably linked 3' to the open reading frame;
(c) a second expression cassette, comprising:
  (i) a weak constitutive promoter, operably linked to an open reading frame encoding a selectable marker; and
  (ii) a polyadenylation site operably linked 3' to the open reading frame; and
(d) a 3' PiggyBac ITR comprising the nucleotide sequence of SEQ ID NO:47.

Embodiment 43: The recombinant expression vector of Embodiment 42, further comprising:
(e) a third expression cassette comprising:
  (i) a control sequence comprising an inducible promoter comprising one or more TetO sequences;
  (ii) an open reading frame encoding a protein of interest (different or the same as the protein of interest encoded by the open reading frame of the first expression cassette) operably linked to the control sequence; and
  (iii) a second polyadenylation site operably linked 3' to the open reading frame.

Embodiment 44: The recombinant expression vector of Embodiment 43, wherein the control sequence (i) of the third expression cassette comprises:
(1) a mCMV enhancer sequence, comprising a mCMV enhancer element (mCMV-E) and a CMV promoter (CMV-P) sequence at its 3' end, operably linked 5' to a rat EF-1alpha intron sequence, comprising one or more TetO sequences inserted within the CMV-P sequence;
(2) an intervening first leader sequence operably linked, 3' to the CMV-P sequence of the mCMV enhancer sequence, and 5' to the rat EF-1alpha intron sequence; and
(3) a second leader sequence operably linked 3' to the rat EF-1alpha intron sequence.

Embodiment 45: The recombinant expression vector of any of Embodiments 42-44, wherein the weak constitutive promoter is a deleted SV40 promoter.

Embodiment 46: The recombinant expression vector of any of Embodiments 42-45, wherein the deleted SV40 promoter comprises the nucleotide sequence of SEQ ID NO:53.

Embodiment 47: The recombinant expression vector of any of Embodiments 42-46, wherein the deleted SV40 promoter comprises the nucleotide sequence of SEQ ID NO:46.

Embodiment 48: The recombinant expression vector of any of Embodiments 42-47, wherein the selectable marker is glutamine synthetase, puromycin resistance, neomycin resistance, zeomycin resistance, or dihydrofolate reductase.

Embodiment 49: The recombinant expression vector of any of Embodiments 42-48, wherein the selectable marker is glutamine synthetase.

Embodiment 50: The recombinant expression vector of any of Embodiments 42-49, wherein the selectable marker is encoded by the nucleotide sequence of SEQ ID NO:49, or a degenerate DNA sequence.

Embodiment 51: A method of selecting a stable production cell line for manufacturing a protein of interest, comprising the following steps:
(a) culturing a mammalian host cell stably transfected with the recombinant expression vector of any of Embodiments 42-44, under selective pressure with respect to a selectable marker constitutively expressed from the weak constitutive promoter, in an aqueous medium under physiological conditions, wherein the mammalian host cell is capable of expressing TetR, in the absence of tetracycline or a tetracycline analog in the medium, whereby expression of protein from the first expression cassette and, if present in the vector, from the third expression cassette, is repressed;
(b) selecting a viable cell line from the host cell(s) cultured in step (a);
(c) culturing the viable cell line from step (b) in an aqueous medium containing tetracycline or a tetracycline analog in an amount sufficient to bind TetR in the host cell(s), whereby expression of the protein of interest by the host cell is derepressed; and
(d) detecting the protein of interest in the culture medium;
(e) selecting a stable production cell line from step (c) that produces a greater amount of the protein of interest relative to a control transfectant in which the aqueous medium in steps (a) and (c) contained tetracycline or a tetracycline analog in an amount sufficient to bind TetR in the host cell, whereby the expression of the protein of interest was derepressed in the control transfectant.

Embodiment 52: The method of Embodiment 51, wherein the mammalian host cell is a CHO cell.

Embodiment 53: The method of any of Embodiments 51-52, wherein the CHO cell is a CHO-K1 cell, a DXB11 cell, or a DG44 cell.

Embodiment 54: A recombinant expression vector, comprising:
(a) a first expression cassette, comprising:
(i) a control sequence comprising:
(1) a mCMV enhancer sequence, comprising a mCMV enhancer element (mCMV-E) and a CMV promoter (CMV-P) sequence at its 3' end, operably linked 5' to a rat EF-1alpha intron sequence, comprising one or more TetO sequences inserted within the CMV-P sequence;

(2) an intervening first leader sequence operably linked, 3' to the CMV-P sequence of the mCMV enhancer sequence, and 5' to the rat EF-1alpha intron sequence; and (3) a second leader sequence operably linked 3' to the rat EF-1alpha intron sequence;

(ii) an open reading frame encoding a first immunoglobulin subunit operably linked to the control sequence; and (iii) a first polyadenylation site operably linked 3' to the open reading frame;

(b) a second expression cassette 3' to the first expression cassette, comprising:

(i) a control sequence comprising a promoter;

(ii) an open reading frame encoding a second immunoglobulin subunit operably linked to the promoter; and (iii) a second polyadenylation site operably linked 3' to the open reading frame; and (c) a transcription termination sequence 3' to the first expression cassette and 5' to the second expression cassette.

Embodiment 55: The recombinant expression vector of Embodiment 54, wherein the control sequence (i) of the second expression cassette comprises:

(1) a mCMV enhancer sequence, comprising a mCMV enhancer element (mCMV-E) and a CMV promoter (CMV-P) sequence at its 3' end, operably linked 5' to a rat EF-1 alpha intron sequence, comprising one or more TetO sequences inserted within the CMV-P sequence;

(2) an intervening first leader sequence operably linked, 3' to the CMV-P sequence of the mCMV enhancer sequence, and 5' to the rat EF-1alpha intron sequence; and (3) a second leader sequence operably linked 3' to the rat EF-1alpha intron sequence.

Embodiment 56: The recombinant expression vector of any of Embodiments 54-55, further comprising:

(d) a third expression cassette comprising:

(i) a weak constitutive promoter, operably linked to an open reading frame encoding a selectable marker; and (ii) a polyadenylation site operably linked 3' to the open reading frame.

Embodiment 57: The recombinant expression vector of Embodiment 56, wherein the weak constitutive promoter is a deleted SV40 promoter.

Embodiment 58: The recombinant expression vector of any of Embodiments 56-57, wherein the deleted SV40 promoter comprises the nucleotide sequence of SEQ ID NO:53.

Embodiment 59: The recombinant expression vector of any of Embodiments 56-58, wherein the deleted SV40 promoter comprises the nucleotide sequence of SEQ ID NO:46.

Embodiment 60: The recombinant expression vector of any of Embodiments 56-59, wherein the selectable marker is glutamine synthetase, puromycin resistance, neomycin resistance, zeomycin resistance, or dihydrofolate reductase.

Embodiment 61: The recombinant expression vector of any of Embodiments 56-60, wherein the selectable marker is glutamine synthetase.

Embodiment 62: The recombinant expression vector of any of Embodiments 56-61, wherein the selectable marker is encoded by the nucleotide sequence of SEQ ID NO:49, or a degenerate DNA sequence.

Embodiment 63: A mammalian host cell, comprising the recombinant expression vector of any of Embodiments 42-50 and 54-62.

Embodiment 64: The mammalian host cell of Embodiment 63, wherein the mammalian host cell is a CHO cell.

Embodiment 65: The mammalian host cell of Embodiment 64, wherein the CHO cell is a CHO-K1 cell, a DXB11 cell, or a DG44 cell.

Embodiment 66: A method of producing a protein of interest, in vitro, comprising culturing the mammalian host cell of any of Embodiments 63-65 in an aqueous medium under physiological conditions permitting expression of the protein of interest; and recovering the protein of interest from the medium.

The following working examples are illustrative and not to be construed in any way as limiting the scope of the invention.

EXAMPLES

Example 1. Materials and Methods

Vector construction. All vectors C, D, E, F, and G included a DNA sequence encoding an exogenous protein of interest "Fc-A" (or "FC-A"; an exemplary Fc fusion with a therapeutic anti-inflammatory antibody), an IRES derived from EMCV virus, the murine dihydrofolate reductase gene, and a 221-bp late polyadenylation derived from SV40 virus as described previously (Kaufman, R. J. et al., "Improved vectors for stable expression of foreign genes in mammalian cells by use of the untranslated leader sequence from EMC virus", Nucl. Acids Res. 19(16): 4485-4490 (1991); Schek, et al., "Definition of the upstream efficiency element of the simian virus 40 late polyadenylation signal by using in vitro analyses", Mol. Cell. Biol. 12(12):5386-93 (1992)). The junction between the IRES and DHFR was aaaaacacgat-TGCTCGAGAGTTGCCACCCATCatg//SEQ ID NO:6, where the lower case letters represent the endogenous IRES sequence and the ATG transcription start site of DHFR is italicized lower case. A single transcript is initiated from these various constructs, which then includes the Fc-A gene, the EMCV IRES, the murine DHFR gene and terminates at the SV40 polyadenylation site.

Various transcription promoting sequences were included either 5' or both 5' and 3' to the sequence described above. This allowed all plasmids to be selected using the DHFR gene and Fc-A as a marker for relative expression. The plasmid backbone for all plasmids was pUC57-simple Genscript (Piscataway, N.J.).

Figure 2:
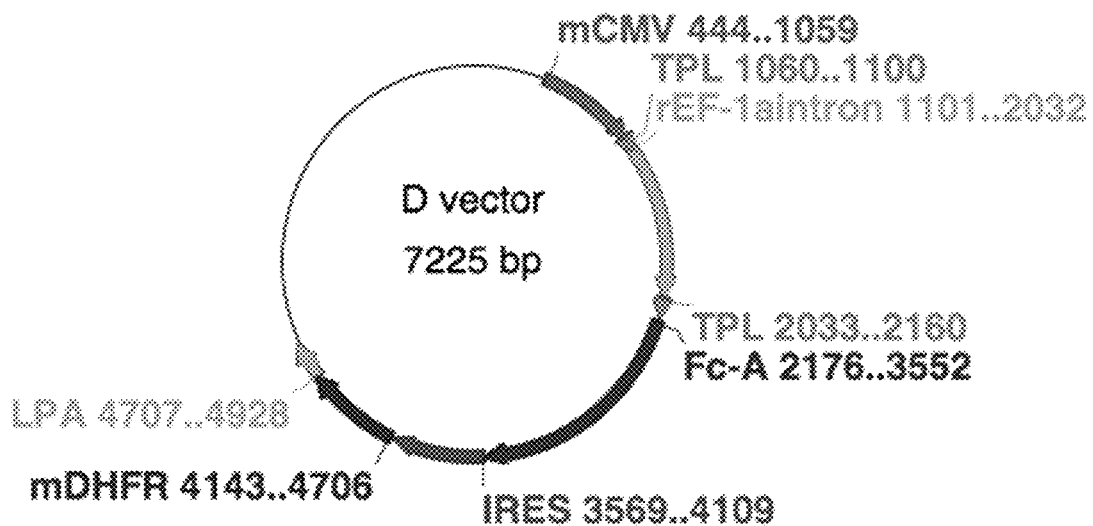
FIG. 2 shows a schematic map of exemplary Vector D.

Several exemplary plasmids are represented schematically in FIG. 1. Vector C contained the human CMV and human EF-1alpha intron sequences described previously (Kim, Lee, Shin, Kang, & Kim, 2002). Vector F (FIG. 1) contained sequences flanking the endogenous Chinese hamster ovary (CHO) EF-1alpha gene as described (Running Deer, J., & Allison, D. S., High-level expression of proteins in mammalian cells using Transcription Regulatory sequences from Chinese Hamster Ovary EF-1alpha Gene, Biotechnology Progress 20:880-889 (2004)) with 4083 bp 5' sequences flanking the ATG and 4174 bp 3' flanking sequences following the polyadenylation site. Vector G (FIG. 1) was constructed by deleting a 240 bp sequence from the transcription start site of the CHO EF-1alpha gene to the FSEI site and replacing it with a DNA fragment encompassing the murine CMV fragment from position −615 to the transcriptional start site. Vector D (FIG. 1) was constructed by synthesizing the fragment shown in SEQ ID NO:1 (containing murine CMV GenBank: L06816.1, nucleotides 4067-4682, Rat EF-1alpha intron Genbank: AC158987.3, nucleotides 22137-21728) and placing these sequences 5' of the Fc-A coding sequence. Vector C and Vector D also contained the adenovirus tripartite leader that replaces the endogenous 3' untranslated leader sequence (Kaufman et al., 1991). The pUC57-simple vector is not shown in FIG. 1. The complete map of Vector D is shown in FIG. 2.

Electroporation and culture of cells. Long duration electroporation were performed as described previously (Bodwell, et al., "Long Duration electroporation for achieving high level expression of glucocorticoi receptors n mammalian cell lines", J. Steriod Biochem. and Mol. Biol., 68(e 8), 77-82 (1999)). Briefly, $2 \times 10^7$ cells were resuspended in 0.3 mL of HBS buffer (0.01 M HEPES pH 7.4, 0.15 M NaCl, 3 mM EDTA, 0.005% v/v Polysorbate20), 25 mg of DNA was added, and electroporated in a 4 mm gap cuvette using a BTX EM 600 with a capacitance of 3175 µF, 720 ohms, and 200 volts.

DXB11 and DG44 cells were cultured in either Power-CHO2 (Lonza), ProCHO4 (Lonza) or Ex-cell 302 (Sigma) according to the manufacturer's instructions. Cells were cultured every 3-4 days and seeded at $4 \times 10^5$ cells/ml for a 3-day culture or $3 \times 10^5$ cells/ml for a 4-day culture.

Protein titer was determined by affinity High Performance Liquid Chromatography (HPLC) using POROS A/20 Protein A column.

Example 2. Transfection of CHO Cells

CHO cells were transfected with various constructs expressing the Fc-A fusion protein. These constructs are shown in FIG. 1 and FIG. 2. Transfected pools of cells were compared for their expression of Fc-A fusion protein.

Transfection of DXB11 cells. The various Fc-A expression plasmids were used to transfect DXB11, a DHFR mutant CHO cell line, using electroporation. These cells were grown in ProCHO4 and were first selected for growth in culture medium lacking hypoxanthine and thymidine and then selected at 150 nM methotrexate (MTX). Pools of cells selected with 150 nM MTX were seeded at $1 \times 10^6$ cells/ml and fed Ex-cell Advanced CHO Feed 1 (SAFC) and glucose on days 2, 4 and 7. Supernatant fluid was harvested on day 8 and analyzed by poros protein A as described above.

Figure 3A:
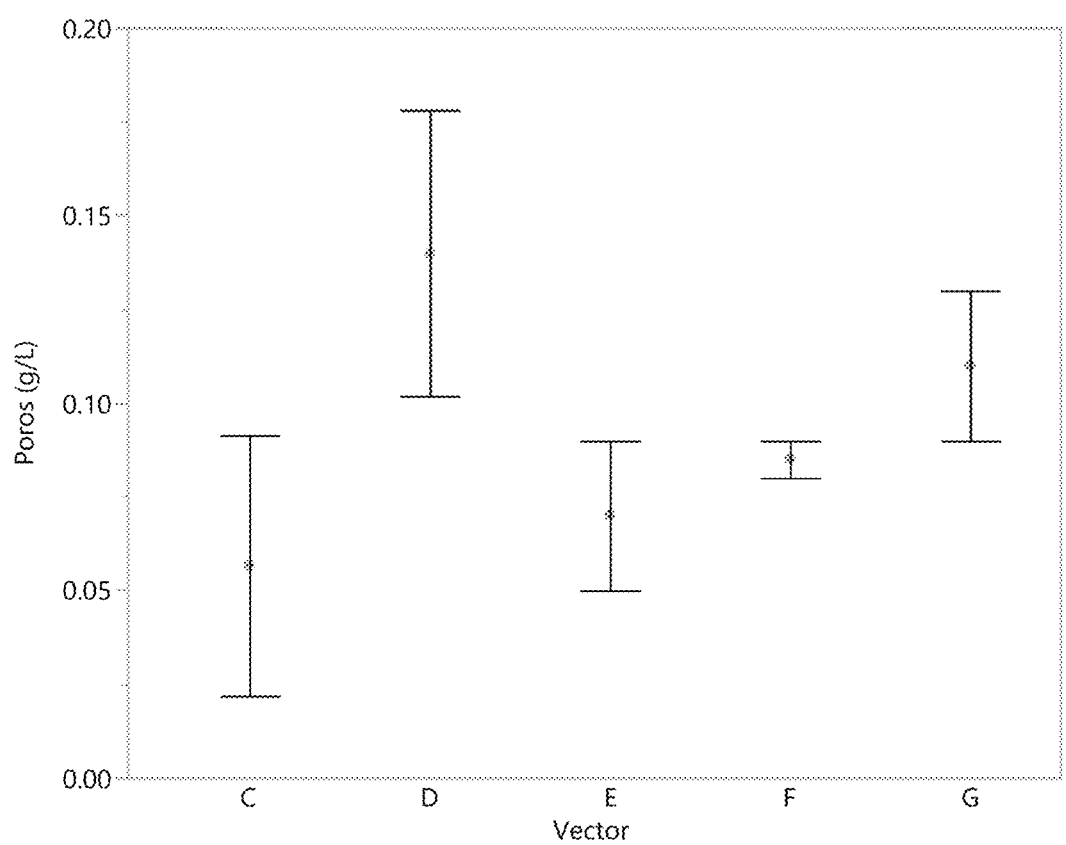
FIGS. 3A and 3B shows DXB11 cell produced Fc-A protein titer (FIG. 3A) and specific productivity (FIG. 3B) in ProCHO™ 4 culture medium containing 150 nM methotrexate (MTX) on Day 8. Each error bar is constructed using 1 standard error of the mean.
Figure 3B:
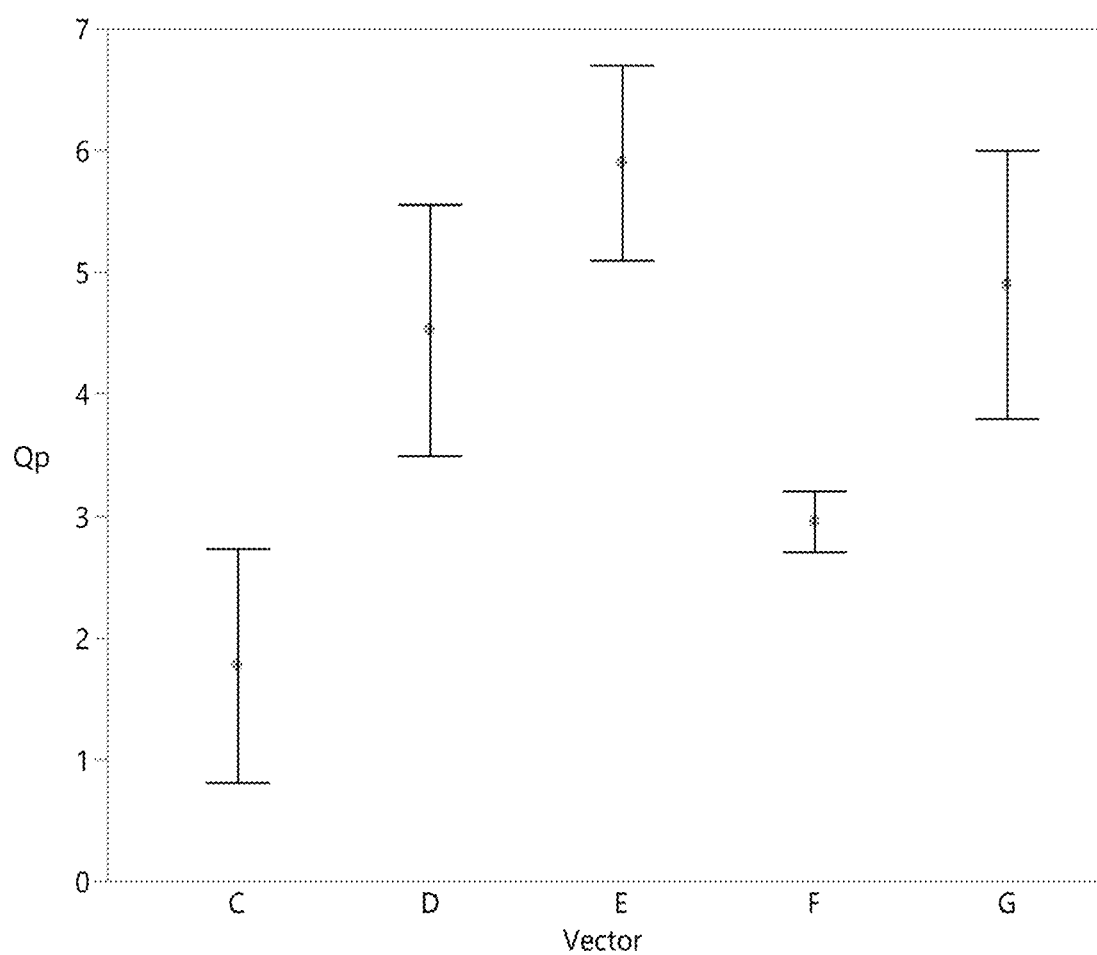

The Fc-A protein titer and specific productivity (picograms per cell per day) are shown in FIG. 3A and FIG. 3B, respectively. The results demonstrated that the hybrid promoter containing murine CMV enhancer combined with the rat EF-1alpha intron and suitable leader sequences (e.g., here the adenovirus tripartite leader; vector D), enhanced expression of the Fc-A recombinant protein by pools of transfected cells. The protein titers achieved were superior to other constructs and specific productivity was as good or better than that obtained using other constructs.

Figure 4A:
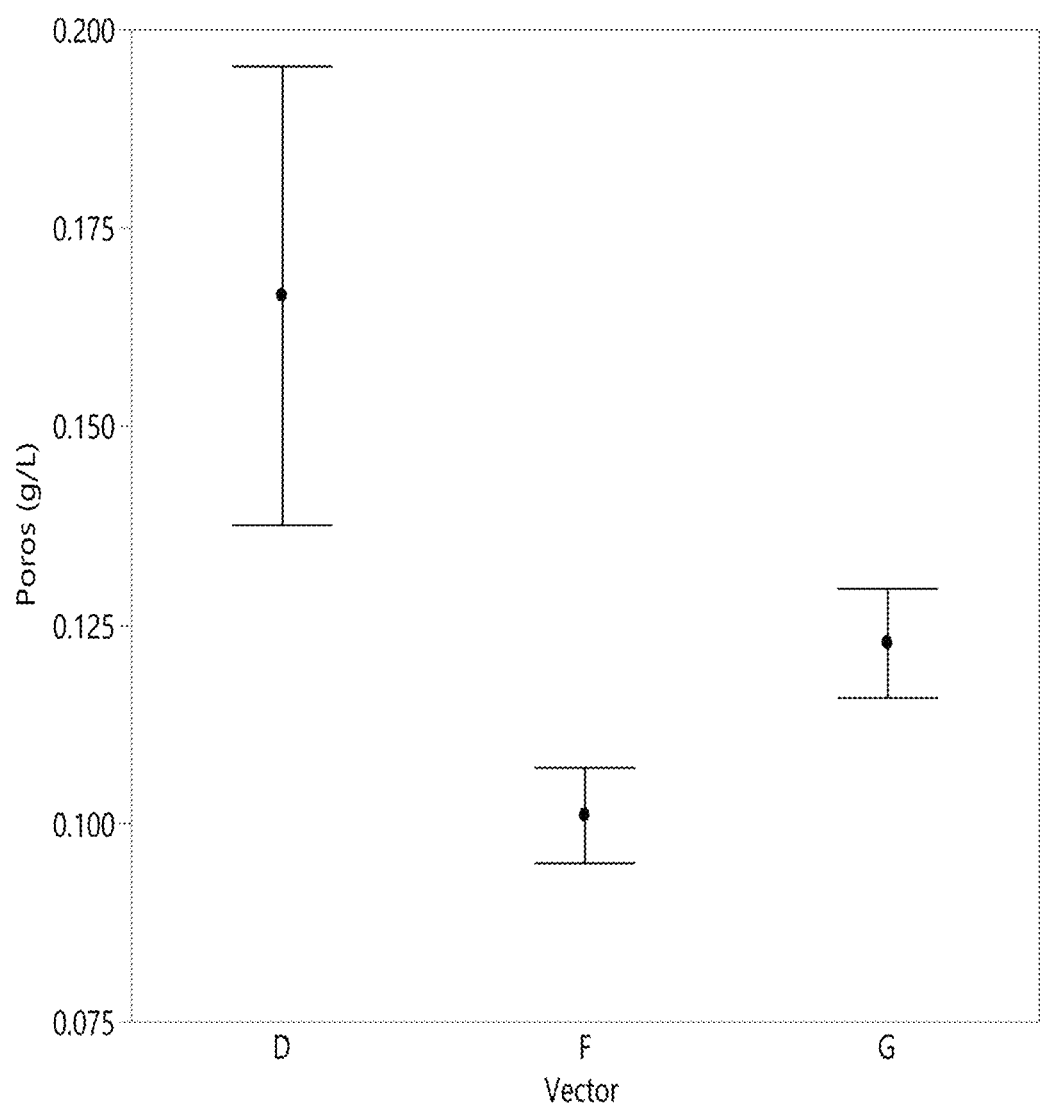
FIGS. 4A and 4B shows DXB11 cell produced Fc-A protein titer (FIG. 4A) and specific productivity (FIG. 4B) in PowerCHO™ 2 medium at 500 nM MTX on Day 8. Each error bar is constructed using 1 standard error of the mean.
Figure 4B:
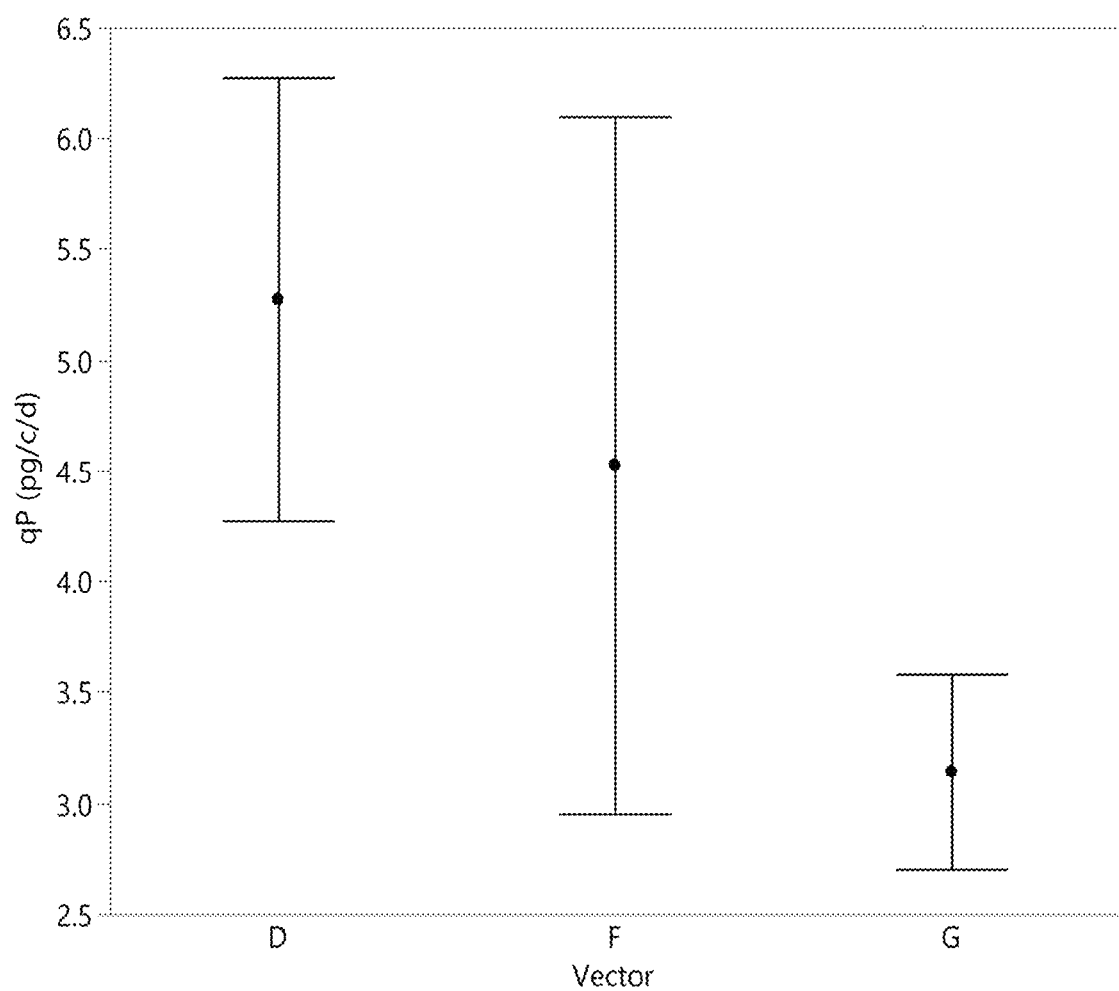

Transfection of DXB-11 with Vectors D, F, and G. Vectors D, F, and G (FIG. 1) were used to transfect DXB11 cells growing in PowerCHO2. Cells were first selected for the growth in medium lacking hypoxanthine and thymidine, amplified to 150 nM MTX and then re-amplified to 500 nM MTX to further enhance expression. These pools were seeded at $1 \times 10^6$ cells/ml and fed with Ex-cell Advanced CHO Feed 1 and glucose on days 2, 3 and 6. Supernatant fluid was harvested on day 8. As shown in FIG. 4A and FIG. 4B, respectively, the titer of those pools transfected with Vector D were significantly higher compared to Vectors F and G. The specific productivities of Vector D were generally higher than Vector F and G.

Figure 5A:
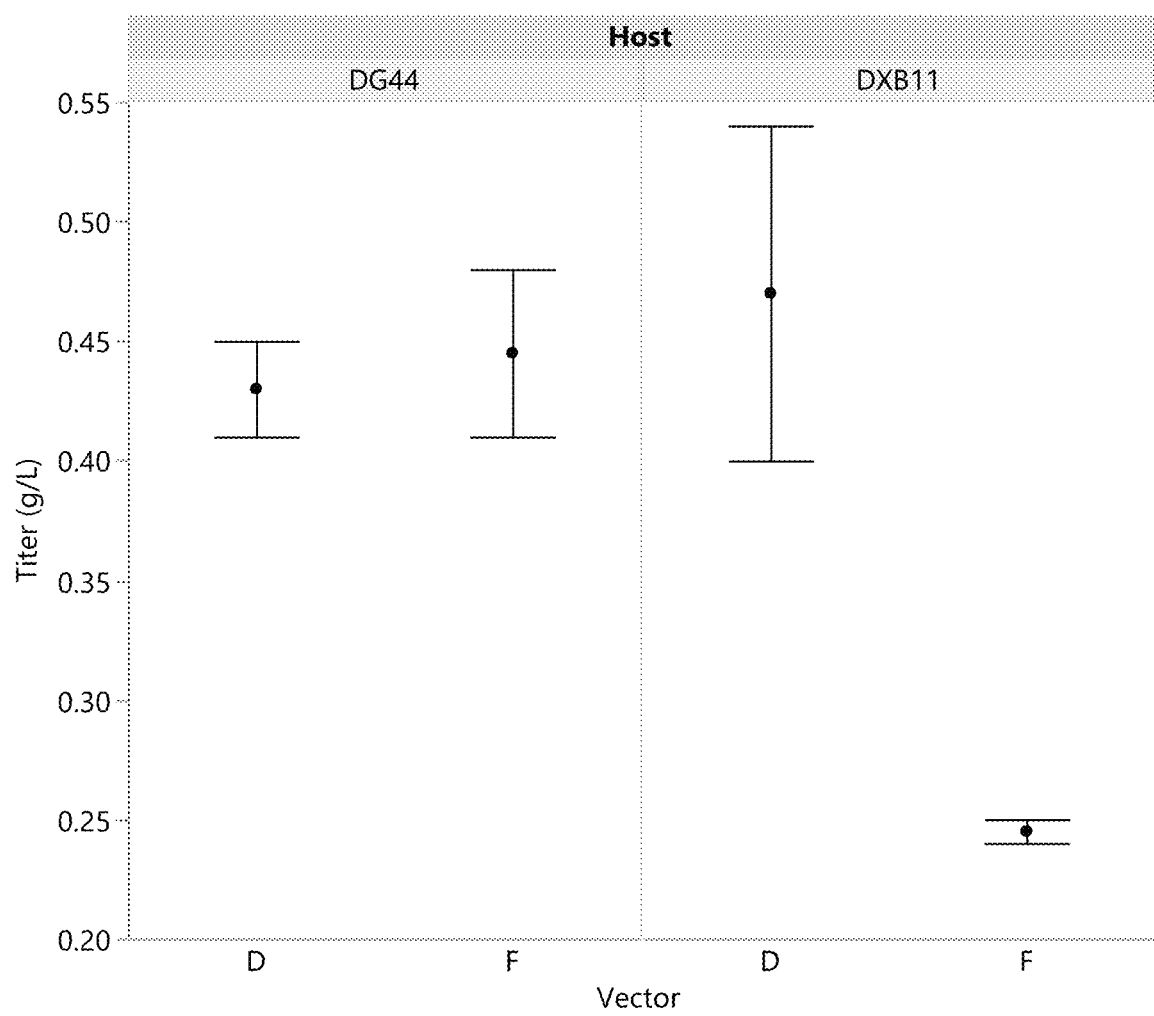
FIGS. 5A and 5B shows Fc-A protein titer (FIG. 5A) and specific productivity (FIG. 5B) for DG44 in PowerCHO™ 2 medium at 1 µM MTX and DXB11 in Excell302 medium at 500 nM MTX, on Day 10. Each error bar is constructed using 1 standard error of the mean.
Figure 5B:
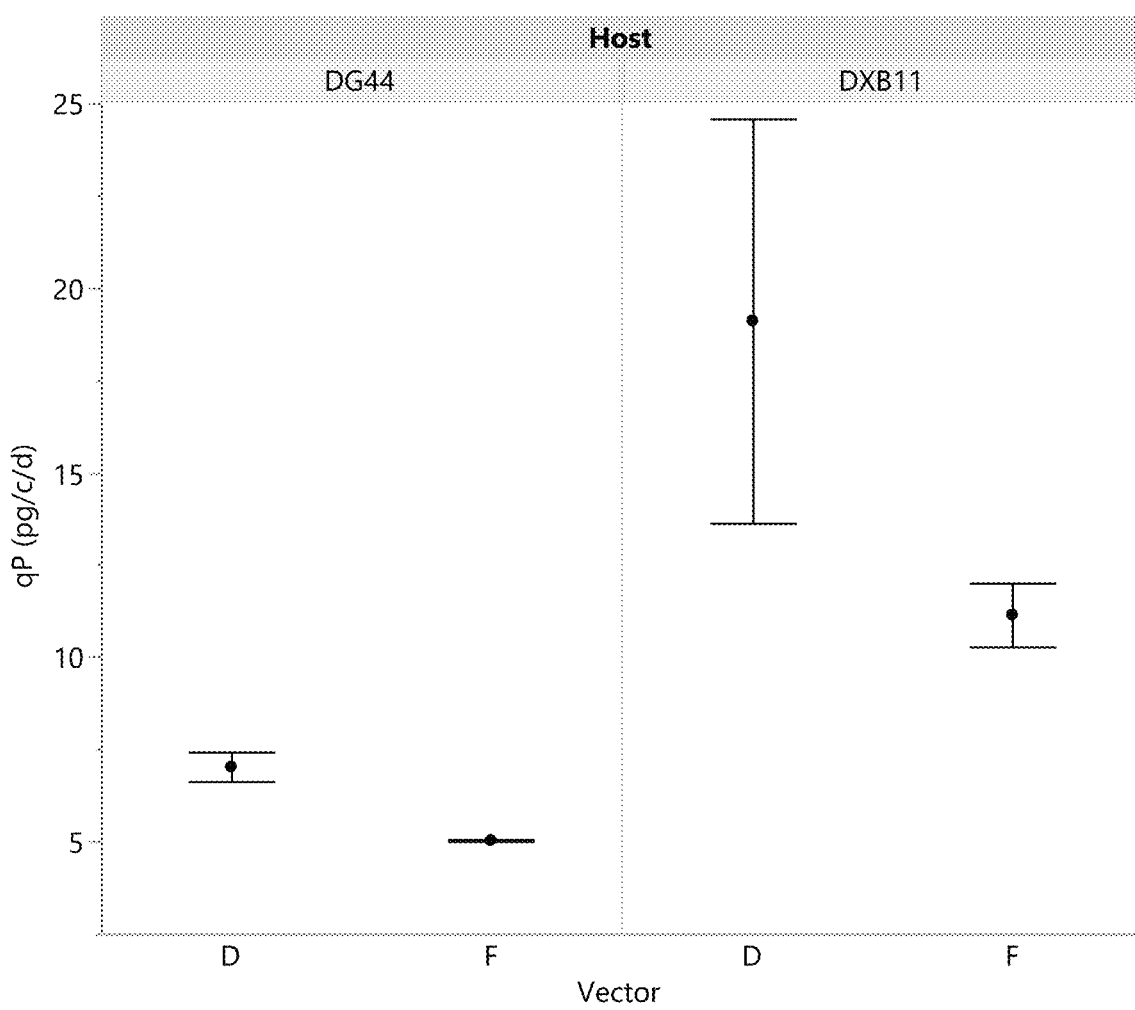

Transfection of DG44 and DXB-11 with Vectors D and F. CHO cells were transfected with Vectors D and F expressing Fc-A fusion protein. DXB11 cells growing in Ex-cell 302 were transfected as described above. DG44, another DHFR mutant cell line, was grown in PowerCHO2 and transfected identically to the DXB11 cells. Transfected pools of cells were compared for their expression of Fc-A. Cells were transfected using electroporation, selected for growth in culture medium lacking hypoxanthine and thymidine, and then amplified to 150 nM MTX. The DXB11 were further amplified to 500 nM MTX and the DG44 cells were further amplified to 1 uM MTX. Pools of cells were then seeded by a 1:5 dilution into growth medium supplemented with Ex-cell Advanced CHO Feed 1, fed on days 3, 6 and 8 with Ex-cell Advanced CHO Feed 1 and glucose. Supernatant fluid was harvested on day 10 and analyzed by poros protein A as described above. The titer and specific productivity are shown in FIG. 5A and FIG. 5B, respectively.

DXB11 Pools transfected with Vector D expressed nearly twice as much Fc-A fusion protein as those pools transfected with Vector F. Pools of DG44 cells transfected with Vectors D and F expressed at similar levels. However, the pools transfected with the Vector D had slightly higher specific productivity. The lower specific productivity of DG44 cells compared to DXB11 cells implies that DG44 cells are less sensitive to the MTX than DXB11 cells.

Vector D also included a 5' untranslated (5'UTR) leader sequence derived from adenovirus tripartite leader (TPL). The TPL has been shown to enhance expression of proteins under stress conditions (Logan & Shenk, "Adenovirus tripartite leader sequence enhances translation of mRNAs late after infection", Proc. Natl. Acad. Sci. USA 81(12): 3655-59 (1984)). Whether the TPL is enhancing expression in these studies is unclear, but other studies have shown that the exact nucleotide sequences of the 5'UTR that one may use in this position varies as long, as they do not contain extensive secondary structures or initiator codons prior to the authentic initiator codon (Mignone, F. et al., Untranslated regions of mRNAs. Genome Biology, 3(3):reviews0004.1-0004.10 (2002)).

Example 3. Tetracycline-Inducible Expression from the Inventive Hybrid Promoter (Control Sequence)

In cells expressing the Tet repressor (TetR), tetracycline can be used to regulate expression from promoters containing the Tet operator sequence (Yao et al.). Introduction of the Tet operator (TetO) sequence just 3' of the TATA box prevents transcription from this promoter in the presence of the TetR. Presumably, TetR binds to TetO and prevents transcription factors from interacting with the transcription start site or interfere with the transcription initiation complex formation (Yao et al). Notably, positioning of the TetO sequences is critical in determining if TetR can effectively modulate transcription. (See, Yao et al., Tetracycline repressor, tetR, rather than the tetR-mammalian cell transcription factor fusion derivatives, regulates inducible gene expression in mammalian cells, Hum. Gene Ther. 9(13):1939-50 (1998)).

Yao et al. hypothesized that positioning the TetO sequence 10 bp downstream of the TATATAA sequence allows binding of the TetR to the same surface as the TATA binding protein. Consistent with this hypothesis, Kim et al. found that insertion of TetO sequences at position 0 or 15 downstream of the hCMV US11 TATAAG sequence failed to preserve repression in the presence of TetR. (See, Kim et al., "Tetracycline repressor-regulated gene repression in recombinant human cytomegalovirus", J. Virol. 69: 2565-257 (1995)).

Figure 6:
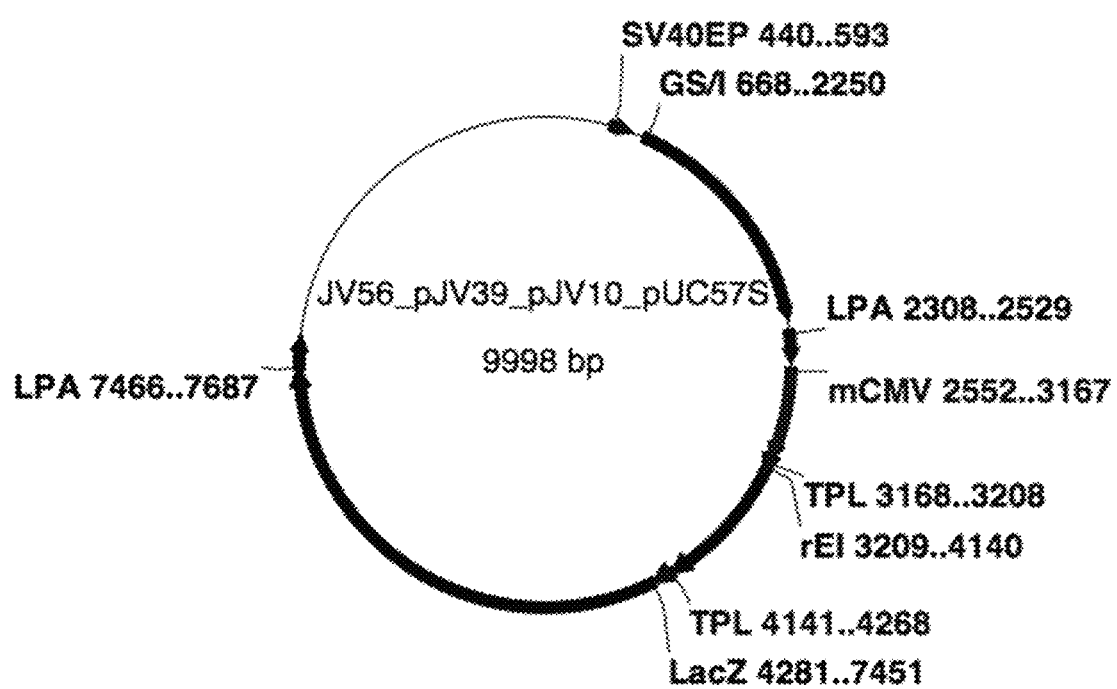
FIG. 6 shows a schematic map of pJV56 with the inventive mCMV enhancer/rEF-1α intron hybrid promoter driving LacZ expression.

Tetracycline (Tet), when added to the culture, will bind TetR and inhibit binding to the TetO sequence, thus allowing transcription. To create a powerful Tet-regulated promoter based on the inventive mCMV enhancer sequence/rat EF-1a intron hybrid promoter sequences, we first generated a plasmid driving LacZ (beta-galactosidase protein) expression, JV56_pJV39_pJV10_pUC57S (herein abbreviated as "pJV56"; FIG. 6). The LacZ open reading frame is SEQ ID NO:12:

```
                                        SEQ ID NO: 12
ATGGGGGGTTCTCATCATCATCATCATCATGGTATGGCTAGCA
TGACTGGTGGACAGCAAATGGGTCGGGATCTGTACGACGATGA
CGATAAGGTACCTAAGGATCAGCTTGGAGTTGATCCCGTCGTT
TTACAACGTCGTGACTGGGAAAACCCTGGCGTTACCCAACTTA
ATCGCCTTGCAGCACATCCCCCTTTCGCCAGCTGGCGTAATAG
CGAAGAGGCCCGCACCGATCGCCCTTCCCAACAGTTGCGCAGC
CTGAATGGCGAATGGCGCTTTGCCTGGTTTCCGGCACCAGAAG
CGGTGCCGGAAAGCTGGCTGGAGTGCGATCTTCCTGAGGCCGA
TACTGTCGTCGTCCCCTCAAACTGGCAGATGCACGGTTACGAT
GCGCCCATCTACACCAACGTAACCTATCCCATTACGGTCAATC
CGCCGTTTGTTCCCACGGAGAATCCGACGGGTTGTTACTCGCT
CACATTTAATGTTGATGAAAGCTGGCTACAGGAAGGCCAGACG
CGAATTATTTTTGATGGCGTTAACTCGGCGTTTCATCTGTGGT
GCAACGGGCGCTGGGTCGGTTACGGCCAGGACAGTCGTTTGCC
GTCTGAATTTGACCTGAGCGCATTTTTACGCGCCGGAGAAAAC
CGCCTCGCGGTGATGGTGCTGCGTTGGAGTGACGGCAGTTATC
TGGAAGATCAGGATATGTGGCGGATGAGCGGCATTTTCCGTGA
CGTCTCGTTGCTGCATAAACCGACTACACAAATCAGCGATTTC
CATGTTGCCACTCGCTTTAATGATGATTTCAGCCGCGCTGTAC
TGGAGGCTGAAGTTCAGATGTGCGGCGAGTTGCGTGACTACCT
ACGGGTAACAGTTTCTTTATGGCAGGGTGAAACGCAGGTCGCC
AGCGGCACCGCGCCTTTCGGCGGTGAAATTATCGATGAGCGTG
GTGGTTATGCCGATCGCGTCACACTACGTCTGAACGTCGAAAA
CCCGAAACTGTGGAGCGCCGAAATCCCGAATCTCTATCGTGCG
GTGGTTGAACTGCACACCGCCGACGGCACGCTGATTGAAGCAG
AAGCCTGCGATGTCGGTTCCGCGAGGTGCGGATTGAAAATGG
TCTGCTGCTGCTGAACGGCAAGCCGTTGCTGATTCGAGGCGTT
AACCGTCACGAGCATCATCCTCTGCATGGTCAGGTCATGGATG
AGCAGACGATGGTGCAGGATATCCTGCTGATGAAGCAGAACAA
CTTTAACGCCGTGCGCTGTTCGCATTATCCGAACCATCCGCTG
TGGTACACGCTGTGCGACCGCTACGGCCTGTATGTGGTGGATG
AAGCCAATATTGAAACCCACGGCATGGTGCCAATGAATCGTCT
GACCGATGATCCGCGCTGGCTACCGGCGATGAGCGAACGCGTA
ACGCGAATGGTGCAGCGCGATCGTAATCACCCGAGTGTGATCA
TCTGGTCGCTGGGGAATGAATCAGGCCACGGCGCTAATCACGA
CGCGCTGTATCGCTGGATCAAATCTGTCGATCCTTCCCGCCCG
GTGCAGTATGAAGGCGGCGGAGCCGACACCACGGCCACCGATA
TTATTTGCCCGATGTACGCGCGCGTGGATGAAGACCAGCCCTT
CCCGGCTGTGCCGAAATGGTCCATCAAAAAATGGCTTTCGCTA
CCTGGAGAGACGCGCCCGCTGATCCTTTGCGAATACGCCCACG
CGATGGGTAACAGTCTTGGCGGTTTCGCTAAATACTGGCAGGC
GTTTCGTCAGTATCCCCGTTTACAGGGCGGCTTCGTCTGGGAC
TGGGTGGATCAGTCGCTGATTAAATATGATGAAAACGGCAACC
CGTGGTCGGCTTACGGCGGTGATTTTGGCGATACGCCGAACGA
TCGCCAGTTCTGTATGAACGGTCTGGTCTTTGCCGACCGCACG
CCGCATCCAGCGCTGACGGAAGCAAAACACCAGCAGCAGTTTT
TCCAGTTCCGTTTATCCGGGCAAACCATCGAAGTGACCAGCGA
ATACCTGTTCCGTCATAGCGATAACGAGCTCCTGCACTGGATG
GTGGCGCTGGATGGTAAGCCGCTGGCAAGCGGTGAAGTGCCTC
TGGATGTCGCTCCACAAGGTAAACAGTTGATTGAACTGCCTGA
ACTACCGCAGCCGGAGAGCGCCGGGCAACTCTGGCTCACAGTA
CGCGTAGTGCAACCGAACGCGACCGCATGGTCAGAAGCCGGGC
ACATCAGCGCCTGGCAGCAGTGGCGTCTGGCGGAAAACCTCAG
TGTGACGCTCCCCGCCGCGTCCCACGCCATCCCGCATCTGACC
ACCAGCGAAATGGATTTTTGCATCGAGCTGGGTAATAAGCGTT
GGCAATTTAACCGCCAGTCAGGCTTTCTTTCACAGATGTGGAT
TGGCGATAAAAAACAACTGCTGACGCCGCTGCGCGATCAGTTC
ACCCGTGCACCGCTGGATAACGACATTGGCGTAAGTGAAGCGA
CCCGCATTGACCCTAACGCCTGGGTCGAACGCTGGAAGGCGGC
GGGCCATTACCAGGCCGAAGCAGCGTTGTTGCAGTGCACGGCA
GATACACTTGCTGATGCGGTGCTGATTACGACCGCTCACGCGT
GGCAGCATCAGGGGAAAACCTTATTTATCAGCCGGAAAACCTA
CCGGATTGATGGTAGTGGTCAAATGGCGATTACCGTTGATGTT
GAAGTGGCGAGCGATACACCGCATCCGGCGCGGATTGGCCTGA
ACTGCCAGCTGGCGCAGGTAGCAGAGCGGGTAAACTGGCTCGG
ATTAGGGCCGCAAGAAAACTATCCCGACCGCCTTACTGCCGCC
TGTTTTGACCGCTGGGATCTGCCATTGTCAGACATGTATACCC
CGTACGTCTTCCCGAGCGAAAACGGTCTGCGCTGCGGGACGCG
CGAATTGAATTATGGCCCACACCAGTGGCGCGGCGACTTCCAG
TTCAACATCAGCCGCTACAGTCAACAGCAACTGATGGAAACCA
GCCATCGCCATCTGCTGCACGCGGAAGAAGGCACATGGCTGAA
TATCGACGGTTTCCATATGGGGATTGGTGGCGACGACTCCTGG
AGCCCGTCAGTATCGGCGGAGTTCCAGCTGAGCGCCGGTCGCT
ACCATTACCAGTTGGTCTGGTGTCAAAAATAA//.
```

The basic idea was to exchange part of the mCMV promoter (mCMV-P) element sequence with the human CMV promoter (hCMV-P) element that includes the TetO binding sites responsible for regulation by tetracycline (Tet).

Figure 7:
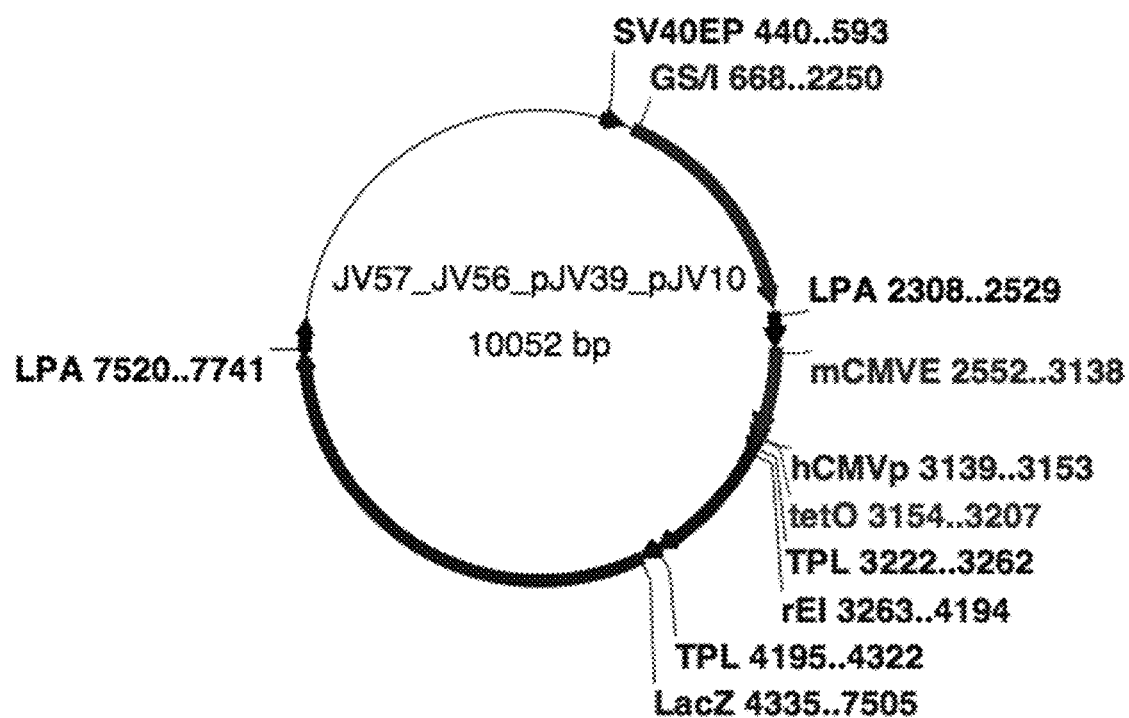
FIG. 7 shows a schematic map of pJV57, which was the same as pJV56, except that part of the mCMV promoter (mCMV-P) was replaced with human CMV promoter (hCMV-P) and TetO sequences.
Figure 8:
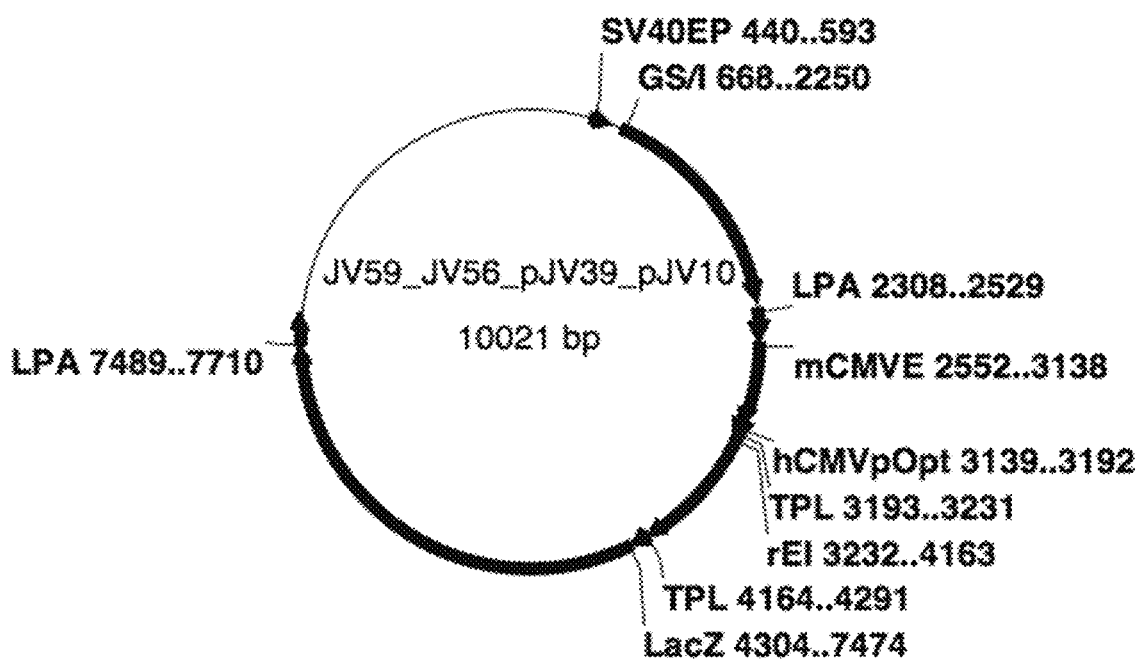
FIG. 8 shows a schematic map of pJV59, which was the same as pJV56, but with an optimized human CMV promoter ((hCMV-P); after Patwardhan et al., "High-resolution analysis of DNA regulatory elements by synthetic saturation mutagenesis", Nature Biotechnology 27(12):1173-75 (2009)), substituted for part of the mCMV promoter (mCMV-P) sequence.
Figure 9:
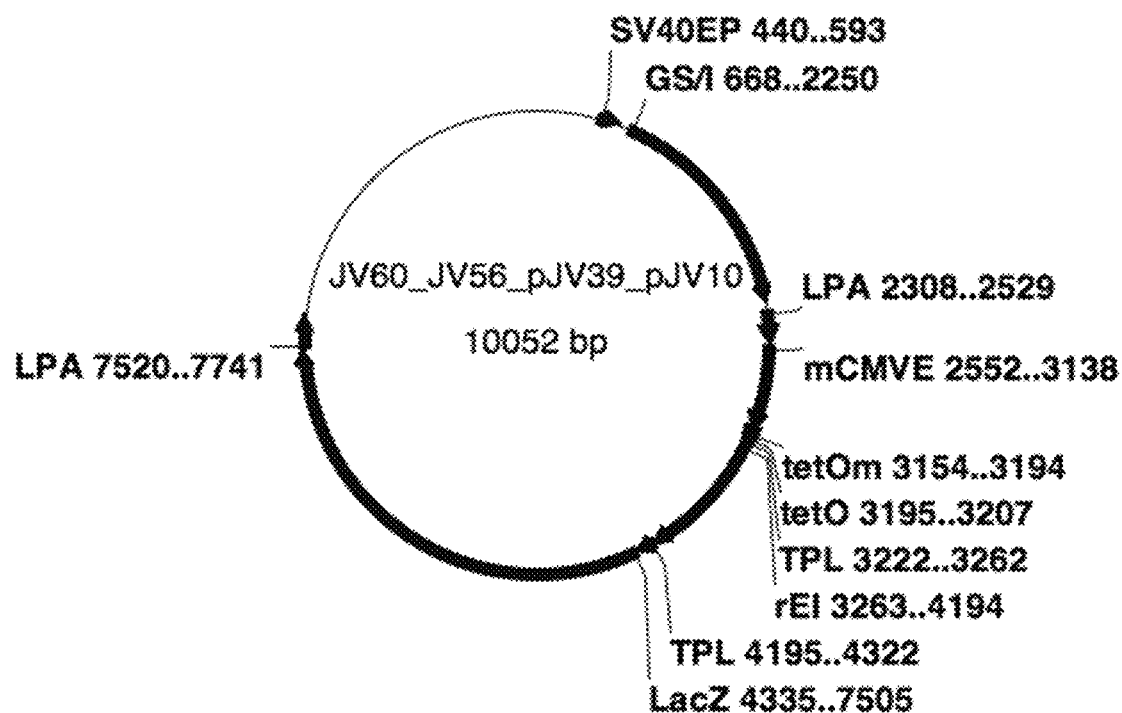
FIG. 9 shows a schematic map of pJV60, which was the same as pJV57, except for changes to the TetO sequences (maintaining TetR binding) to match the optimized human CMV promoter (hCMV-P) sequence.
Figure 10:
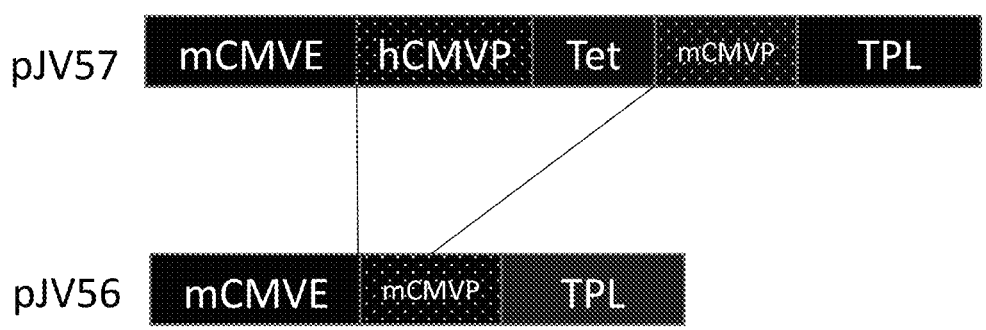
FIG. 10 shows a schematic representation of the human CMV promoter-Tet operator (TetO; "Tet") inserted into the mCMV promoter ("mCMVP") sequence, 3' to the mCMV enhancer element ("MCVE") sequence. This insertion replaced part of the mCMV promoter with a hCMV promoter (hCMVP) sequence. The relative position of the first leader sequence is also represented by "TPL."

This construct, JV57_JV56_pJV39_pJV10 (herein abbreviated as "pJV57"; FIG. 7), includes the tetracycline-sensitive TetO regulatory element for expression of LacZ. FIG. 10 shows schematically the hCMV-P/TetO inserted into the mCMV promoter sequence. This insertion replaces part of the mCMV-P promoter sequence with a part of the hCMV-P promoter sequence. Another construct was made to incorporate expression-increasing changes in a hCMV promoter described by Patwardhan et al. in the context of an unregulated promoter (hybrid mCMV enhancer/(partial) hCMV promoter/rat EF-1alpha intron). (Patwardhan et al., "High-resolution analysis of DNA regulatory elements by synthetic saturation mutagenesis", Nature Biotechnology 27(12): 1173-75 (2009)). This construct was JV59_JV56_pJV39_pJV10 (abbreviated herein as "pJV59"; FIG. 8). In another construct, JV60_JV56_pJV39_pJV10 (herein abbreviated as "pJV60"; FIG. 9), the TetO sequences of pJV57 were changed to match the sequences that increased expression surrounding the transcription start site in the study by Patwardhan et al. (see, FIG. 9 and FIG. 12).

Figure 11:
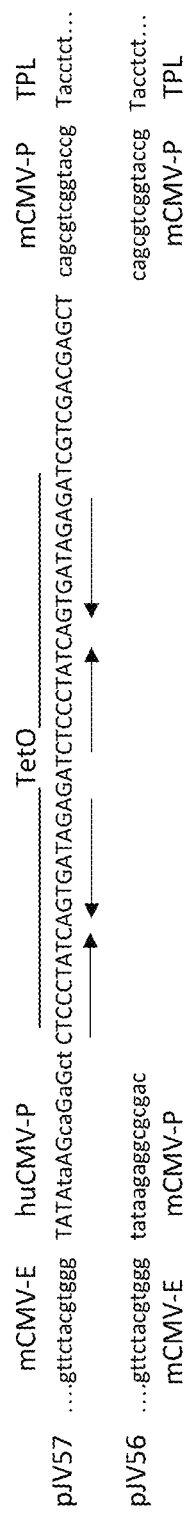
FIG. 11 shows a schematic comparison of the DNA sequences of a segment of pJV56 (SEQ ID NO:16) and a segment of pJV57 (SEQ ID NO:15). The segment of pJV57 shown in SEQ ID NO:15 includes a segment (SEQ ID NO:9) that incorporates a partial hCMV promoter sequence (SEQ ID NO:24) and, 3' to SEQ ID NO:24, a TetO sequence (SEQ ID NO:23, which contains a smaller TetO sequence SEQ ID NO:29). Arrows shown in the TetO sequence (SEQ ID NO:29) indicate palindromic TetR binding sites. The mCMV promoter (mCMV-P) sequence and hCMV promoter (hCMV-P) sequence are those sequences from the TATA box through the start site of transcription. SEQ ID NO:25 is the 3' end of a mCMV-P sequence found in both pJV57 and pJV56, and in pJV57 is found 3' to SEQ ID NO:9. The transcription start is the guanine residue in the 3' subsequence taccg of SEQ ID NO:25. Note that the inserted TetO sequence (SEQ ID NO:23) most certainly impacts the transcription start site, since the transcription start site is typically ~30 bases 3' to the 5' T of the TATA box. The relative position of the first leader sequence is also represented by "TPL," and some nucleotide residues at the 5' end of the TPL are shown.

FIG. 11 shows the DNA sequence of hCMV-P/TetO that we used to replace the mCMV promoter (mCMV-P) sequences. Arrows indicate palindromic TetR binding sites. The mCMV-P and hCMV-P promoter sequences shown are those sequences from the TATA box through the start site of transcription. The transcription start is the g residue in the 3' sequence taccg. Note that the TetO sequence most certainly impacts the transcription start site, since the transcription start site is typically ~30 bases 3' to the 5' T of the TATA box.

Figure 14:
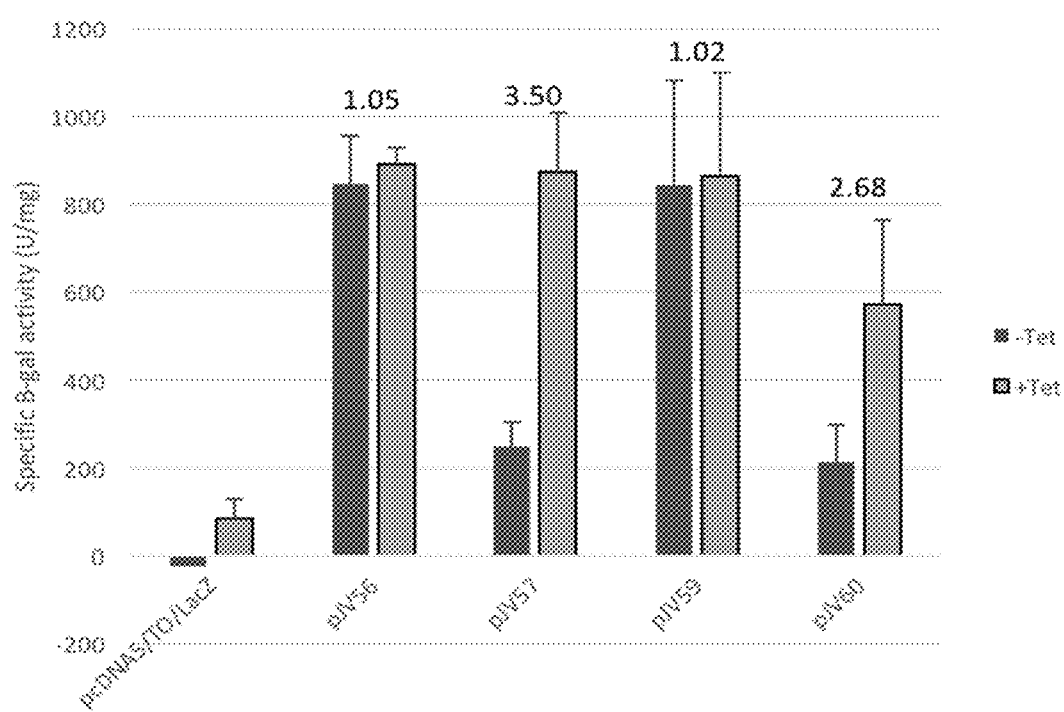
FIG. 14 shows regulation of specific β-galactosidase expression for each of the indicated vectors. T-REx™-CHO cells expressing TetR were transiently transfected with pJV56, pJV57, pJV59, pJV60, or the control plasmid pcDNA5/TO/LacZ. Cell were incubated for 24 hours and then treated with tetracycline (Tet) or left untreated for 24 hours. Cells were lysed and LacZ was analyzed enzymatically. The fold-difference between the (+Tet) compared to (−Tet) is shown above the bars, except for the positive control (pcDNA5/TO/LacZ).

We expressed beta-galactosidase from various constructs to monitor the level of protein expression. This inserted substitute sequence, which includes muCMV enhancer element (mCMV-E)/(partial) huCMV promoter/TetO/ratEF-1alpha intron, was indeed regulated by tetracycline in the medium (See, e.g., FIG. 14, pJV57+/−Tet). Furthermore, the construct pJV57 yielded approximately 10-fold as much recombinant protein as a human CMV/TetO control (pcDNA5/TO/LacZ; Thermo Fisher Scientific), when Tet was present in the medium, but about 3.5-fold less beta-galactosidase in the absence of tetracycline, as shown in FIG. 14. T-Rex CHO cells bearing the muCMV enhancer/ratEF-1alpha intron hybrid promoter in pJV56, absent a TetO sequence within the CMV-P segment of the mCMV enhancer sequence, also expressed approximately 10 times more protein than the human CMV/TetO control (pcDNA5/TO/LacZ), regardless of whether tetracycline was in the medium.

Materials and Methods

T-REx™-CHO cells. T-REx-CHO cell line (Thermo Fisher Scientific, Product No. R71807) were cultured in Ham's F12 medium+glutamine+10 µg/ml Blast per manufacturer's protocol. T-REx-CHO cells were electroporated using the long duration electroporation (LDE) method as described by Bodwell et al. (Bodwell et al., "Long Duration Electroporation for Achieving High Level Expression of Glucocorticoid Receptors in Mammalian Cell Lines", J. Steroid Biochem. Molec. Biol. 68:77-82 (1999)), with various constructs pJV56, pJV57, pJV59, and pJV60, expressing the beta-galactosidase protein, as shown in FIG. 6, FIG. 7, FIG. 8, and FIG. 9, respectively. Transfected cells were allowed to recover for 24 hours and then were treated with or without 1 µg/ml tetracycline for 24 hours. Cells were lysed and beta-galactosidase activity was assayed using a β-Gal Assay Kit per manufacturer's protocol (Thermo Fisher Scientific, Product No. K1455-01). Briefly, lysates were diluted 10-fold and 10-µl aliquots were assayed using a BCA protein assay kit (Thermo Fisher Scientific, Product No. 23227) to determine protein concentration of the lysate. Lysates were diluted 100-fold and 10-µl aliquots were assayed for beta-galactosidase activity. All samples were transfected at least in duplicates. Specific beta-galactosidase activity was normalized to the amount of protein assayed and background activity of mock-transfected cells was subtracted from transfected samples. Results were graphed with standard deviation shown (FIG. 14).

Figure 15:
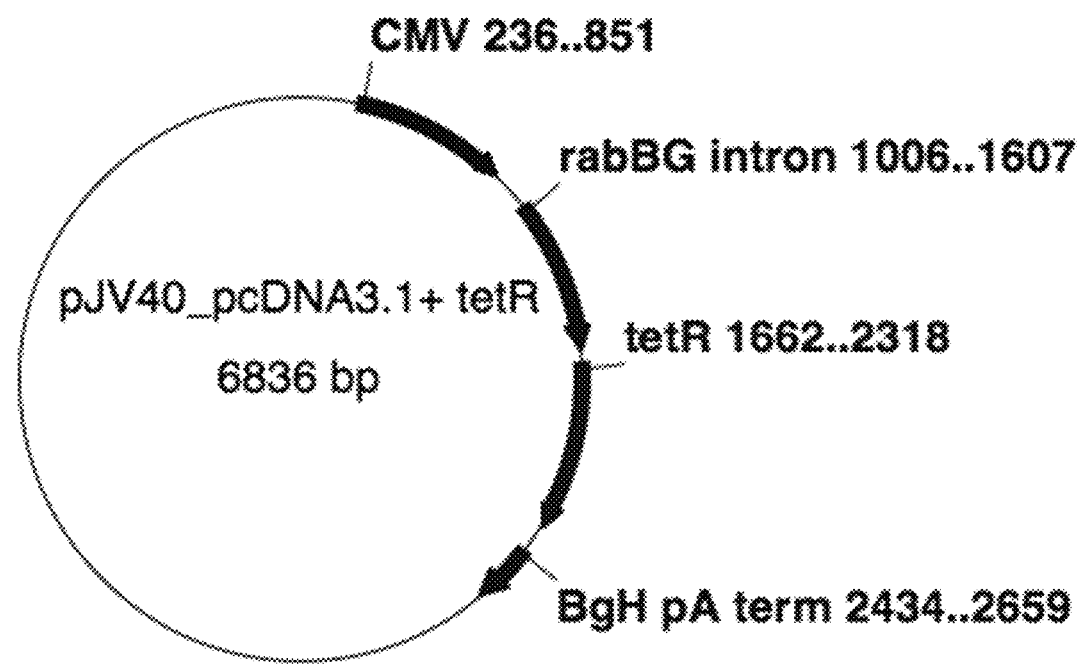
FIG. 15 shows a schematic map of pJV40, including an open reading frame for TetR.

CHO-K1/TetR cells. In separate experiments, tetracycline repressor (TetR) was subcloned by Genscript® (Piscataway, N.J.) into pcDNA3.1+expression vector to yield vector pJV40_pcDNA3.1+tetR (abbreviated herein, as "pJV40"; FIG. 15). CHO-K1 cells were routinely cultured in PowerCHO™ 2 Chemically Defined, Serum-free CHO Medium (Lonza, Product No. BE12-771Q), and cells were electroporated using the LDE method, as described above for pJV40. Transfected pools were selected for 10 days in PowerCHO™ 2+600 µg/ml G418 (Gibco, Product No. 10131027). Cells were then serially diluted and plated in 96-well microplates (Corning® CellBIND® 96 Well, Product #3340) at 0.75 cell per well in cloning medium (EX-CELL® 302 Serum-Free Medium for CHO Cells; Sigma-Aldrich, Product No. 14326C SIGMA)+15% conditioned medium in the presence of G418). Clonal populations were identified after 11-12 days and were transferred to 12-well plates in 50/50 cloning medium/PowerCHO™ 2 medium for an additional 3-4 days. Finally, clones were moved and grown in a 24 deep-well plate (VWR, Product No. P-DW-10ML-24-C-S) with constant shaking (220 rpm) in PowerCHO™ 2 medium+600 µg/ml G418.

To screen for clones expressing high levels of TetR, CHO-K1/TetR clones were transfected with pJV57 using the ExpiFectamine™ CHO transfection kit (Thermo Fisher Scientific, Product No. A29130) per manufacturer's protocol. From those highly expressing TetR clones, some clones were subsequently chosen to be transfected with vector pJV56, pJV57, pJV59, or pJV60, using the ExpiFectamine™ CHO transfection kit (Thermo Fisher Scientific, Product No. A29130), again transfected per manufacturer's protocol. Transfected clones were allowed to recover for 24 hours and then were treated with 1 µg/ml tetracycline for 24 hours. To measure expression of the LacZ protein product, cells were lysed, and beta-galactosidase activity was assayed using a β-Gal Assay Kit per manufacturer's protocol (Thermo Fisher Scientific, Product No. K1455-01). Briefly, lysates were diluted 10-fold and 10-µl aliquots were assayed using a BCA protein assay kit (Thermo Fisher Scientific, Product No. 23227) to determine protein concentration of the lysate. Ten (10) µl of undiluted lysate was assayed for beta-galactosidase activity. All samples were transfected at least in duplicates. Specific beta-galactosidase activity was normalized to the amount of protein assayed and background activity of mock-transfected cells was subtracted from transfected samples. Results were graphed with standard deviation shown (e.g., FIG. 16, FIG. 17, FIG. 18).

Figure 16:
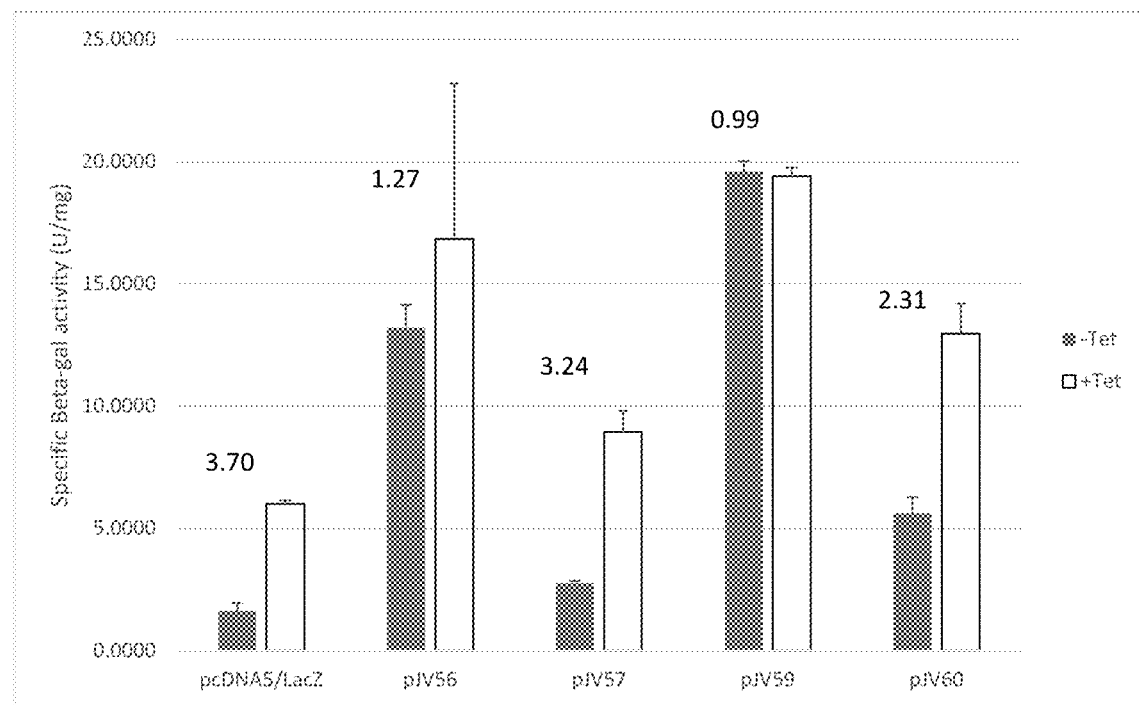
FIG. 16 illustrates expression of LacZ (beta-galactosidase protein) by CHO-K1/TetR cells (clone 3E7) expressing TetR, which were transiently transfected with pJV56, pJV57, pJV59, pJV60, or the control plasmid pcDNA5/TO/LacZ. Cell were incubated for 24 hours and then treated with tetracycline (Tet) or left untreated for 24 hours. Cells were lysed and LacZ was analyzed enzymatically. The fold-difference between the (+Tet) compared to (−Tet) is shown above the bars.
Figure 17:
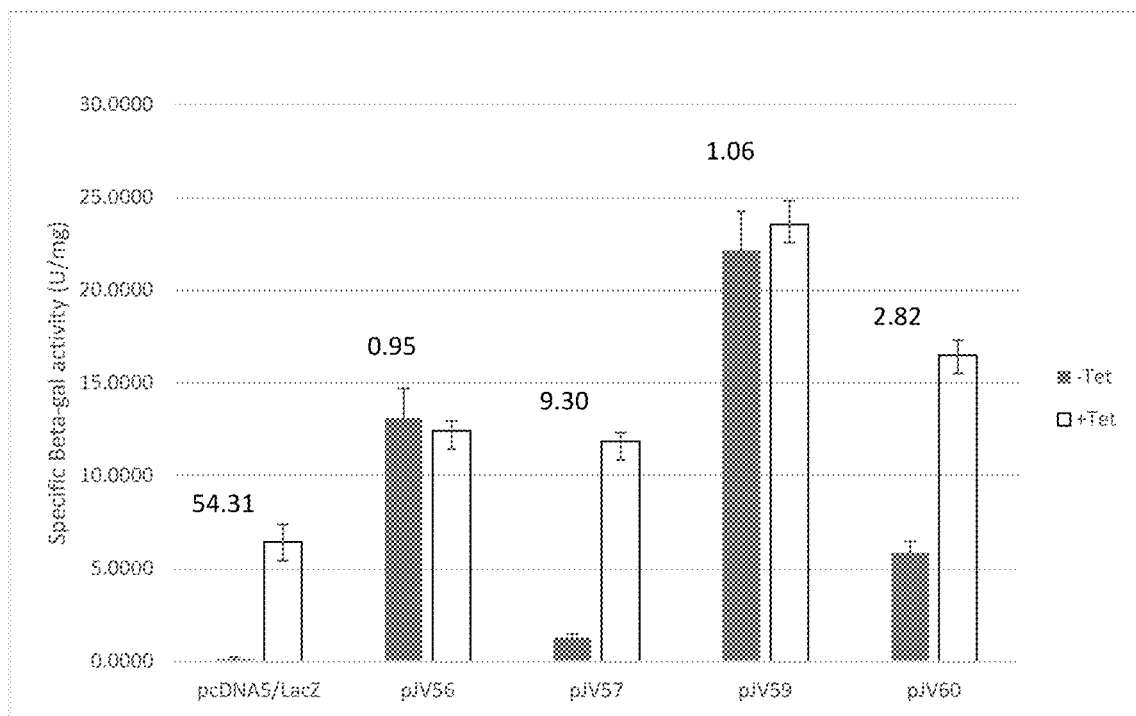
FIG. 17 illustrates expression of LacZ (beta-galactosidase protein) by CHO-K1/TetR cells (clone 3F9) expressing TetR, which were transiently transfected with pJV56, pJV57, pJV59, pJV60, or the control plasmid pcDNA5/TO/LacZ. Cell were incubated for 24 hours and then treated with tetracycline (Tet) or left untreated for 24 hours. Cells were lysed and LacZ was analyzed enzymatically. The fold-difference between the (+Tet) compared to (−Tet) is shown above the bars.
Figure 18:
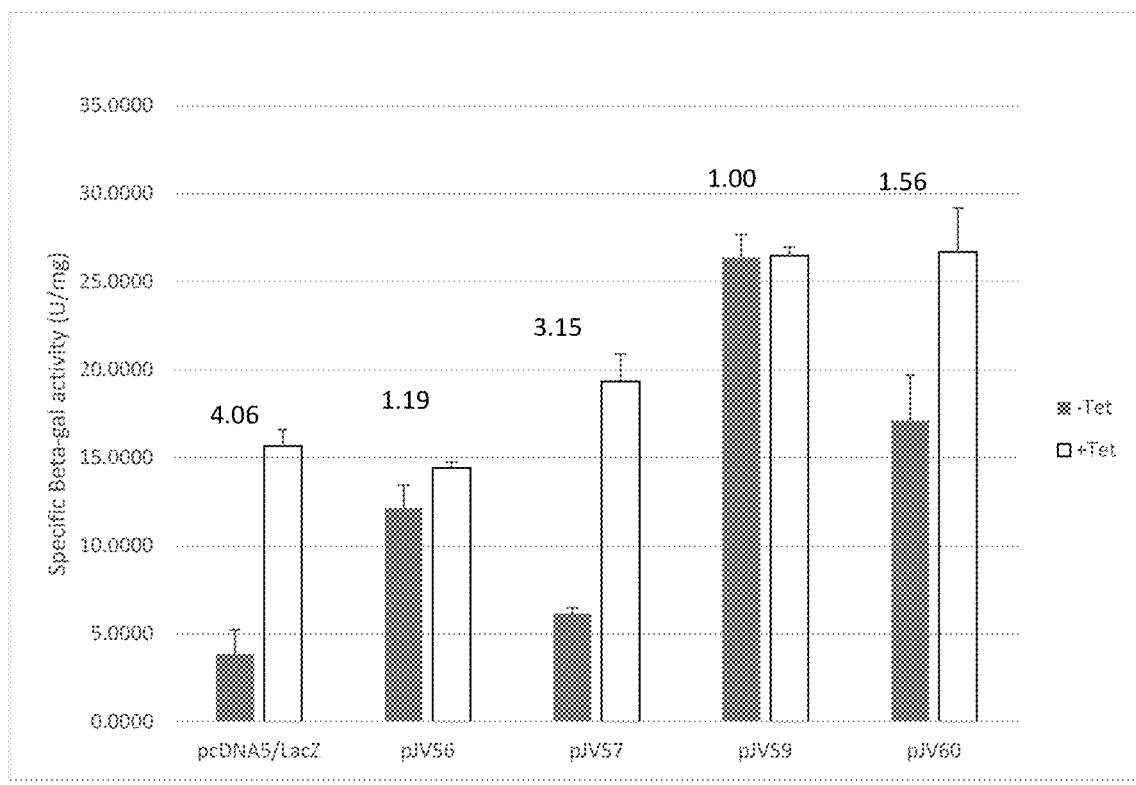
FIG. 18 illustrates expression of LacZ (beta-galactosidase protein) by CHO-K1/TetR cells (clone 4G2) expressing TetR, which were transiently transfected with pJV56, pJV57, pJV59, pJV60, or the control plasmid pcDNA5/TO/LacZ. Cell were incubated for 24 hours and then treated with tetracycline (Tet) or left untreated for 24 hours. Cells were lysed and LacZ was analyzed enzymatically. The fold-difference between the (+Tet) compared to (−Tet) is shown above the bars.

FIG. 16 (clone 3E7), FIG. 17 (clone 3F9), and FIG. 18 (clone 4G2) shows representative results from CHO-K1/TetR clones transfected with various constructs (pJV56, pJV57, pJV59, and pJV60) expressing the beta-galactosidase protein (or transfected with positive control: pcDNA5/TO/LacZ; Thermo Fisher Scientific, Product No. V1033-20). As above, cells were transfected with pJV57 using the ExpiFectamine™ CHO transfection kit (Thermo Fisher Scientific, Product No. A29130) per manufacturer's protocol. Transfected clones were allowed to recover for 24 hours and then were treated with 1 µg/ml tetracycline for 24 hours. Cells were lysed, and beta-galactosidase activity was assayed using a β-Gal Assay Kit per manufacturer's protocol (Thermo Fisher Scientific, Product No. K1455-01). Briefly, lysates were diluted 10-fold and 10-µl aliquots were assayed using a BCA protein assay kit (Thermo Fisher Scientific, Product No. 23227) to determine protein concentration of the lysate. Ten (10) µl of undiluted lysate was assayed for beta-galactosidase activity. All samples were transfected at least in duplicates. Specific beta-galactosidase activity was normalized to the amount of protein assayed and background activity of mock-transfected cells was subtracted from transfected samples. Specific beta-galactosidase activity was normalized to the amount of protein assayed and background activity of mock-transfected cells was subtracted from transfected samples. Results were graphed with standard deviation shown.

Results

T-REx™ CHO cells. In experiments using T-RExCHO cells (Thermo Fisher Scientific), a commercial cell line that stably expresses TetR, we measured beta-galactosidase (beta-gal) activity as a readout to test the ability of pJV57 to be regulated by tetracycline (Tet). As shown in FIG. 14, pJV57 had equivalent expression to pJV56 when induced by the presence of tetracycline (+Tet). In addition, pJV57 had approximately 10-fold higher expression of LacZ in the presence of tetracycline (+Tet) when compared with pcDNA5/TO/LacZ, a vector shown to exhibit robust tetracycline-regulated expression. pJV57 also showed 3.5-fold regulated expression by tetracycline, a key observation demonstrating a powerfully regulated promoter. Fold-difference in Tet regulation for the positive control pcDNA5/TO/LacZ was not included in FIG. 14, because of low signal-to-noise ratio between uninduced pcDNA5/TO/LacZ and background, resulting in a negative specific beta-gal activity in the control.

In an attempt to further improve upon pJV57, we hypothesized that the TetO sequences could reduce expression from pJV57 as previous studies showed that changes around the transcription start site reduced expression from the hCMV promoter (Patwardhan et al., "High-resolution analysis of DNA regulatory elements by synthetic saturation mutagenesis", Nat Biotechnol. 27(12): 1173-1175 (2009)). The TetO sequences in pJV57 were changed to match the sequences that increased expression surrounding the transcription start site in the study by Patwardhan et al. (pJV60, FIG. 9 and FIG. 12). Furthermore, these changes were designed to maintain high affinity TetR binding (the affinity of different TetO mutations is described in Sizemore et al. and reviewed in Hillen and Berens). (See, Sizemore et al., "Quantitative analysis of Tn10 Tet repressor binding to a complete set of tet operator mutants", Nucleic Acids Research 18 (10) 2875-2880 (1990); Hillen and Berens, "Mechanisms underlying expression of Tn10 encoded tetracycline resistance", Ann. Rev. Micro. 48:345-369 (1994)). However, this optimized construct, pJV60, did not appear to increase expression compared to pJV57 in T-REx-CHO cells (FIG. 14). Tetracycline-regulated expression was maintained, but potentially slightly less regulation (2.68-fold compared to 3.50-fold (FIG. 14).

The optimized hCMV promoter (hCMV-P) sequences replaced the mCMV promoter (mCMV-P) sequences in the mCMV enhancer sequence/rat EF-1a intron hybrid promoter of the invention (see, sequence comparison in FIG. 13). The changes incorporated into pJV59 did not appear to increase expression relative to pJV56 (FIG. 14). Thus, we conclude that in the T-REx-CHO cells, the context of the powerful mCMV enhancer/promoter-rat EF-1a intron, that changes around the transcription start site have little or no impact on expression.

CHO-K1/TetR cells. In separate experiments, a CHO-K1 cell line stably expressing TetR was generated by transfection of pJV40 (see, FIG. 15) that has TetR gene subcloned into pcDNA3.1+ vector. Geneticin-resistant CHO-K1 pools were serially diluted to obtain single-cell colonies and screened to have high expression of TetR, i.e. more than two-fold repression of LacZ in the absence of Tet (data not shown). Three clones were selected for further analysis, as shown respectively in FIG. 16, FIG. 17, and FIG. 18, referred to herein as CHO-K1/TetR clones. The clones were transiently transfected with pcDNA5/TO/LacZ as a control, and expression vectors of the present invention, i.e., vectors pJV56, pJV57, pJV59 and pJV60, as described above, to determine the effectiveness of a Tet-regulated promoter element based on the mCMV enhancer sequence/rat EF-1a intron hybrid promoter sequences using TetR-expressing cells that were generated in-house.

As shown in FIG. 16, FIG. 17, FIG. 18, pJV56 in two of the 3 CHO-K1/TetR clones exhibited 2- to 3-fold higher expression of LacZ compared to pcDNA5/TO/LacZ in the presence of tetracycline (+Tet). Addition of hCMV-P/TetO sequences in pJV57 enabled protein expression to be regulated by tetracycline to the extent of 3.24-, 9.30- and 3.15-fold enhancement of LacZ expression in the presence of tetracycline (+Tet), compared to (−Tet) (see, pJV57, in FIG. 16, FIG. 17, and FIG. 18 respectively), although the level of expression was variable depending on the clone studied. This is comparison to pJV56, which did not include the hCMV-P/TetO sequences (1.27-, 0.95-, 1.19-fold differences between +Tet and minus-Tet treatments, as shown in FIG. 16, FIG. 17, and FIG. 18, respectively).

Interestingly, total expression of LacZ was increased in all three pJV59-transfected CHO-K1/TetR clones, although as expected there was essentially no tetracycline-sensitive regulation of expression (±Tet comparison: 0.99-, 1.06-, 1.00-fold difference), as shown in FIG. 16, FIG. 17, and FIG. 18, consistent with our hypothesis that protein expression can be increased by optimizing sequences surrounding the transcription start site (see, Patwardhan et al.). However, addition of TetO sites that were mutated to maintain TetR binding (pJV60)—in the context of the optimized promoter—showed decreased (FIG. 16, FIG. 17) or unchanged (FIG. 18) LacZ expression compared to pJV59. Nevertheless, LacZ expression was augmented in all three pJV60-bearing clones compared to pJV57, in the presence of tetracyclin (2.31-, 2.82- and 1.56-fold higher expression compared to its non-Tet-treated control; FIG. 16, FIG. 17, FIG. 18, respectively). This suggests that mutation of TetO sequences adversely affected TetR binding as observed by higher basal LacZ expression in all clones in the absence of Tet and lower fold-induction upon +Tet addition.

Overall, all of the pJV56, pJV57, pJV59, and pJV60 constructs in CHO/TetR cells demonstrated increased LacZ expression compared to CHO cells expressing from pcDNA5/TO/LacZ (i.e., positive controls) in the presence of tetracycline, and CHO cells bearing the inventive hybrid promoter with hCMV-P/TetO sequences had beta-galactosidase expression up-reregulated by tetracycline (1.56- to 9.30-fold differences), compared to (−Tet), as shown in FIG. 16, FIG. 17, and FIG. 18. It should be noted that the method of transfection is different between T-REx-CHO cells (adherent) to CHO-K1/TetR cells (cell suspension in liquid aqueous medium), and that transfection efficiency may account for differences observed in the overall levels of specific beta-galactosidase activity.

Example 4. Limiting the Metabolic Burden of Recombinant Protein Expression During Selection Yields Pools with Higher Expression Levels We sought to test the idea that the metabolic burden of any recombinant protein expression, if high enough, would impact the selection process during CHO cell line development. We first developed an inducible expression system by isolating tetracycline repressor (TetR) expressing CHO cell lines (see, Example 3 hereinabove), and then transfected these TetR cell lines with expression vectors expressing either a Fc fusion protein or a recombinant antibody. Neither of the proteins displayed obvious toxicity in constitutive expression systems. For these two proteins, we show that pools that were induced to express a recombinant protein expression during cell line selection had lower titers than pools that were uninduced during cell line selection. These data are consistent with the hypothesis that the metabolic burden of protein expression selects against the higher expressing clones during selection of cell pools.

Materials and Methods

Cell Culture. CHOK1 GS KO cells (Horizon Discovery) were maintained in CD OptiCHO™ (Gibco)+4 mM glutamine (Q). Cells were passaged every 3-4 days at a seed density of 0.3-0.4×10$^6$/mL. A codon optimized tetracycline repressor (TetR) was synthesized (Genscript) and subcloned into an expression vector with human CMV driving TetR expression. GS KO cells were electroporated using the LDE method as described (Bodwell et al., Long Duration electroporation for achieving high level expression of glucocorticoi receptors n mammalian cell lines, J. Steroid Biochem. Mol. Biol. 68(8):77-82 (1999)) with TetR vector. Transfected pools were selected for about 12 days in CD OptiCHO™+glutamine +400 µg/ml G418 (Gibco). Pools were then transfected (as described below in the transient transfection section) with pcDNA5/TO/LacZ (ThermoFisher), allowed to recover for 24 hours and then treated with or without tetratcycline (Tet, 1 µg/mL) for 24 hours to identify the pool with high Tet-dependent induction of the target gene. Cells were lysed, and beta-galactosidase activity was assayed using a β-Gal Assay Kit per manufacturer's protocol (ThermoFisher Scientific) and read on Spectra Max 5 plate reader (Molecular Devices). Briefly, lysates were diluted 10-fold and 10 µl was assayed using a BCA protein assay kit (ThermoFisher) to determine protein concentration of the lysate. Ten microliters (10 µL) of undiluted lysate was assayed for beta-galactosidase activity. Tet and a more stable derivative, doxycycline (Dox), were used to induce cultures, as described herein.

The selected pool was then serially diluted and plated in 96-well microplates (Corning® CellBIND®) at 0.75 cells per well in cloning medium (EX-CELL® 302 Serum-Free Medium for CHO Cells)+15% conditioned medium in the presence of G418). Clonal populations were identified after 11-12 days (CloneSelect Imager, Molecular Devices) and transferred to 12-well plates in 50/50 cloning medium/CD OptiCHO™ medium for an additional 3-4 days. Finally, clones were transferred to 24 deep-well plates (VWR) with constant shaking (220 rpm) in CD OptiCHO™ medium+ glutamine+400 µg/ml G418.

To screen for clones expressing high levels of TetR, clones were transfected with pcDNA5/TO/LacZ or an in-house plasmid expressing LacZ using the HCN protocol (see, Transient transfection section, below). Transfected clones recovered for 24-48 hours and then were treated with 1 µg/mL Tet for 24 hours. Cells were lysed, and beta-galactosidase activity was assayed using a β-Gal Assay Kit per manufacturer's protocol as described above. All samples were transfected at least in duplicate. Specific beta-galactosidase activity was normalized to the amount of protein assayed and background activity of mock-transfected cells was subtracted from transfected samples.

Transient transfection. Cells were passaged to 1×10$^6$/mL the day before transfection. On the day of transfection, cells were counted on a Vi-Cell XR (Beckman Coulter) and electroporated using the high copy number (HCN) protocol (see, Barsoum J., Introduction of stable high-copy-number DNA into Chinese hamster ovary cells by electroporation, DNA Cell Biol. 9(4):293-300 (1990)) in duplicate or triplicates. Briefly, 1×10$^6$ cells were used per transfection. Cells were spun down and resuspended in 150 µl of PF CHO medium (Sigma Aldrich) and aliquoted into one well of a 5×5 electroporation plate (BTX). Ten micrograms (10 µg) of plasmid DNA and 10 µg of salmon sperm DNA (Sigma Aldrich) were used per transfection. PF CHO medium was used to bring final transfection volume up to 50 µL, and aliquots were placed into appropriate wells in the 5×5 electroporation plate. For mock-transfected samples, salmon sperm DNA was used only. Cells were electroporated under these conditions: 290V voltage, 950 µF capacitance, 950 ohm resistance in an ECM 630 electro manipulator coupled to a HT-100 high throughput adaptor (BTX). After electroporation, cells were transferred to a 24 deep well plate containing 1 mL of fresh growth medium without antibiotics and were allowed to recover for 2 days. Two days post-transfection, a duplicate 24 deep well plate was generated from half of the cells in each well and treated with 1 µg/mL tetracycline (Tet; Sigma Aldrich). On days 4, 6 and 8, cells were fed with 10% CD Efficient Feeds (Thermo Fisher Scientific) A+B+C (3.3% each) and 1 µg/mL Tet.

Stable transfection. Cells were passaged to 1×10$^6$/mL the day before transfection and counted on a Vi-Cell the day of transfection, as described above. Cells were electroporated using the long-duration method (Bodwell et al., Long Duration electroporation for achieving high level expression of glucocorticoi receptors n mammalian cell lines, J. Steroid Biochem. Mol. Biol. 68(8):77-82 (1999)) in, at least, duplicate cultures. For each transfection 20×10$^6$ cells were used. Cells were spun down, resuspended in 300 µL PF CHO medium (Sigma) and aliquoted to a 4-mm electroporation cuvette (VWR International). Meanwhile, a DNA/RNA mixture was prepared. For each transfection, a total of 25 µg DNA/RNA was mixed with PF CHO to a final volume of 50 µL. For the transposon experiments, 22.5 µg of transposon and 2.5 µg of transposase RNA (10%) was used. For mock-transfected cells, DNA/RNA were omitted from the PF CHO mixture. Cells were electroporated under these conditions: 200V voltage, 725 µF capacitance, 3175 ohm resistance in an ECM 630 electro manipulator coupled to a 630B safety stand (BTX; See, Barsoum J., Introduction of stable high-copy-number DNA into Chinese hamster ovary cells by electroporation, DNA Cell Biol. 9(4):293-300 (1990)). After electroporation, cells were resuspended in 15 mL of fresh growth medium, +glutamine, without antibiotics and allowed to recover for 2 days in a stationary T75 flask. After this recovery period, cells were counted on a Vi-Cell and were seeded for selection at 0.75 to 1×10$^6$/mL in CD OptiCHO™ medium (Gibco), −Q+antibiotics (as needed) in a 24 deep well plate shaking at 220 rpm. Cells were counted and passaged every 3-4 days on a Guava® easyCyte™ flow cytometer (MilliporeSigma). In some cases, cells were treated with doxycycline (Dox; Sigma D9891) to a final concentration of 0.5 µg/mL. In all cases, there was a replicate culture plate without Dox as a control for +Dox cultures.

Fed batch production. Cells were seeded by dilution into a CD OptiCHO™ or CD FortiCHO™ (Gibco) production medium to a density of 0.7-1.5×10⁶/mL. On day 0, production medium was frontloaded with 30% CD Efficient Feeds A, B and C (10% of each feed). On days 3, 6 and 8 of production, cells were fed with 10% CD Efficient Feeds A, B and C (3.3% of each feed) and glucose was added as necessary to a final concentration of about 10 g/L. Growth profiles (viable cell density and viability) were also measured on days 3, 6 and 8 on a Guava® easyCyte™ flow cytometer (MilliporeSigma). Glucose was measured using a colorimetric assay (Stanbio Laboratory) on a Spectra Max 5 plate reader (Molecular Devices). The measurement of titer measurements was performed by affinity High Performance Liquid Chromatography (HPLC) using POROS A/20 Protein A column. For the interval between days [m, n], Specific productivity (qP) was calculated according to the formula: $qP=titer_n/\int_m^n VCDdt/(t_n-t_m)$, where and time (t) is expressed in days.

Quantitative PCR (qPCR). On day 3 of production, anywhere from 200,000 to 2×10⁶ cells were isolated, spun down and resuspended vigorously in 300 µL RA 1 buffer (Macherey-Nagel)+1% B-ME (Sigma). Cell lysates were frozen at −70° C. until ready for automated purification on a BioRobot (Qiagen) using a NucleoSpin RNA kit (Macherey-Nagel). The concentration of RNA was measured on a Nanodrop spectrophotometer (Thermo Fisher) before qPCR set up. Once concentrations were determined on the Nanodrop, RNA was diluted to 5-10 ng/µL. Two microliters (2 µL) was used as a template in a 20-µL reaction. qScript XLT 1-step RT-PCR kit (Quanta) or the Luna Universal 1-step RT-qPCR kit (New England Biolabs) was used according to manufacturer's protocol. Transcripts of interest were normalized to GAPDH and beta-actin. Ratios of LC/HC were calculated by dividing the relative fold-change of LC by the relative fold-change of HC. The primer sequences used are listed below in Table 1, in a 5' to 3' orientation.

TABLE 1

Primer sequences employed.

| | |
|---|---|
| GAPDH Forward | CCTGGAGAAACCTG CCAAGTATGA// SEQ ID NO: 36 |
| GAPDH Probe: 5' Cy5-labeled | AGAAGGTGGTGAAG CAGGCATCTGAGGG CC// SEQ ID NO: 37 |
| GAPDH Reverse | ACTGTTGAAGTCGC AGGAGACAA// SEQ ID NO:38 |
| Beta-actin Forward | CCCAGCACCATGAA GATCAA// SEQ ID NO: 39 |
| Beta-actin Probe: 5' Fluorescein (6-FAM)-labeled | CATTGCTCCTCCTG AGCGCAAGTA// SEQ ID NO: 40 |
| Beta-actin Reverse | TGCTTGCTGATCC ACATCTC// SEQ ID NO: 41 |
| Glutamine synthetase (GS) Forward | GGGAACAGATGGG CACCCTTT// SEQ ID NO: 42 |
| GS Probe: 5' Hexachloro-Fluorescein (Hex)-labeled | TTGGCCTTCCAAT GGCTTTCCTGGGC// SEQ ID NO: 43 |
| GS Reverse | ACGATATCCCTGCC ATAGGCTTTGT// SEQ ID NO: 44 |

Results

Generation of a TetR-expressing CHO-K1 (GS KO) clone. A CHO-K1 glutamine synthetase (GS) knock out (GS KO, Horizon Discovery) cell line stably expressing TetR was generated by transfection of a plasmid that has the TetR gene subcloned into a vector with human CMV driving expression of TetR. (Yao, F. et al., Tetracycline Repressor, tetR, rather than the Cell Transcription Factor Fusion Derivatives, Regulates Inducible Gene Expression in Mammalian Cells, Hum Gene Ther. 9:1939-1950 (1998)). Geneticin-resistant CHO-K1 (GS KO) pools (TetR-GS KO) were serially diluted to obtain single-cell colonies and screened to have high expression of TetR. This was achieved by transient transfection of TetR-GS KO clones with pcDNA5/TO/LacZ, a vector expressing the reporter enzyme beta-galactosidase under the control of a Tet-regulatable hCMV promoter. The top clones were selected based on their ability to repress expression of LacZ by more than two-fold (data not shown).

Figure 25A:
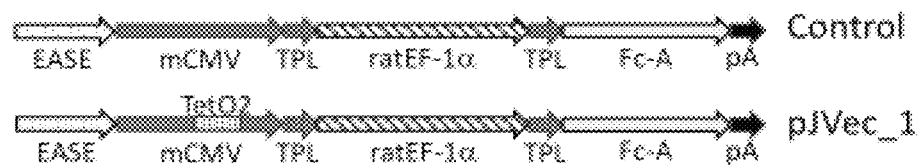
FIG. 25A shows a schematic representation of pJVec_1 (inducible) and control (constitutive).
Figure 25B:
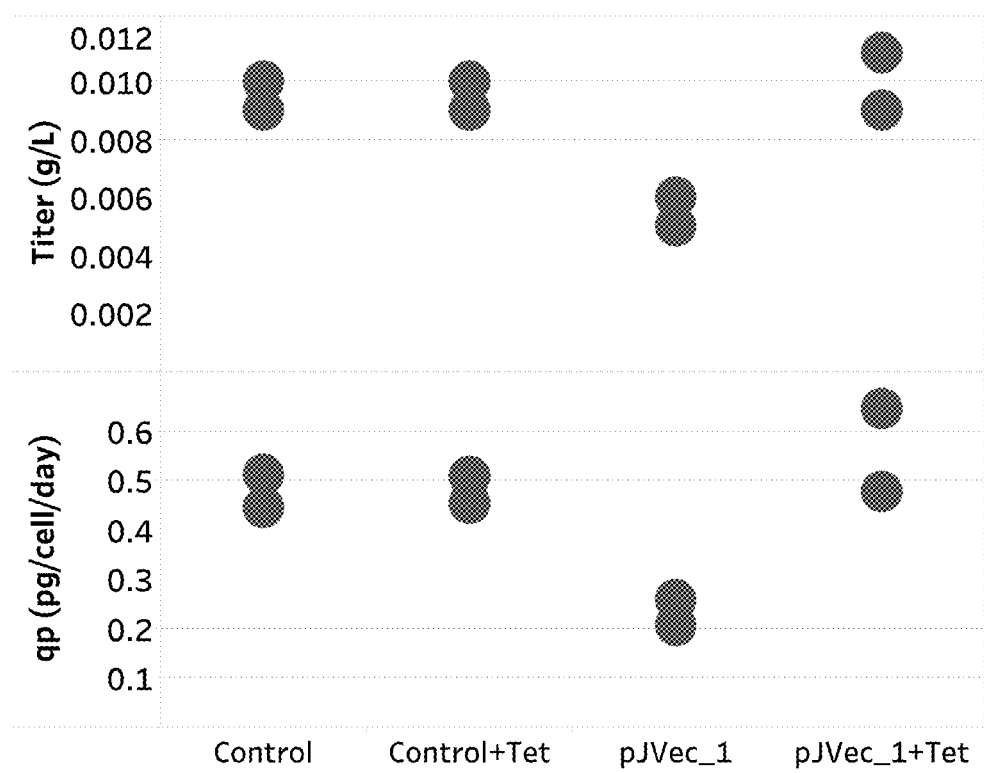
FIG. 25B shows results of expression of an Fc-fusion protein transiently transfected into Clone_A cells. n=2

Regulation of an Fc-fusion protein expression in a TetR-GS KO clone. A representative TetR-GS KO clone, 9G1, was selected for further analysis (FIG. 25A-B). Clone 9G1 was transiently transfected with a vector system expressing a recombinant Fc-fusion protein (Fc-A) under the control of a Tet-regulated hybrid promoter, pJVec_1, as described in Examples 1-3, herein (FIG. 25A, each point on the graph represents a transfection replicate). A constitutive hybrid promoter identical to the inducible promoter except lacking TetO sequences was used as a control (FIG. 25A). Two days post-transfection, transfectants were treated with 1 µg/ml tetracycline (Tet) to induce Fc-A expression while a duplicate plate was left untreated as a control. FIG. 25B shows that upon treatment with Tet, there is a 2-fold and 2.4-fold increase in Fc-fusion titer and qP, respectively, in pJVec_1 transfected cells. As expected, we saw that cells transfected with the control vector were not responsive to Tet and constitutively expressed recombinant Fc-A protein.

Description of inducible transposon-based system. Next, we sought to determine the relationship between recombinant protein production and cellular growth. We expressed an Fc-fusion protein, Fc-A, by using an inducible transposon-based vector system. As described in FIG. 25A-B, Fc-A expression was driven by the promoter consisting of mCMV/TPL/rat EF-1a intron and glutamine synthetase was used as the selectable marker. Transposon vectors were co-transfected with a transposase in a 4:1 (donor transposon:

transposase) mass ratio to promote transposition of target genes. 9G1 cells require glutamine supplementation in the medium for survival and thus, cells that have stably integrated the target protein (Fc-A) and GS can be selected in medium lacking glutamine. To increase stringency of selection and isolate high-producing cells, 75 or 100 µM L-methionine sulfoximine (MSX) was added to the medium during stable pool generation. (Fan, L. et al., Improving the efficiency of CHO cell line generation using glutamine synthetase gene knockout cells, Biotechnol Bioeng. 2012; 109(4):1007-1015 (2012); Rajendra, Y. et al., Generation of stable Chinese hamster ovary pools yielding antibody titers of up to 7.6 g/L using the piggyBac transposon system, Biotechnol Prog. 32(5):1301-1307 (2016)). Additionally, transfectants were treated with 0.5 µg/mL doxycycline (Dox) to induce Fc-A expression or without Dox, as a control, during the selection process.

Figure 19A:
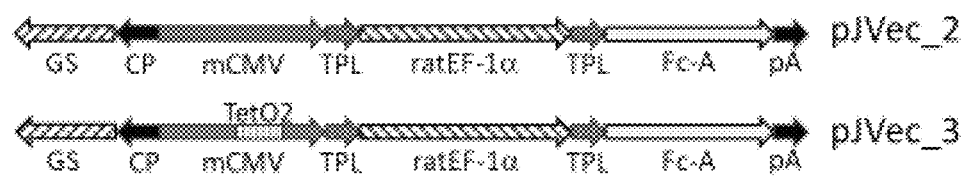
FIG. 19A-C show that an inducible transposon expression system can regulate cellular growth in CHOK1-TetR (GS KO) pools expressing an Fc-fusion protein during growth phase.
Figure 19B:
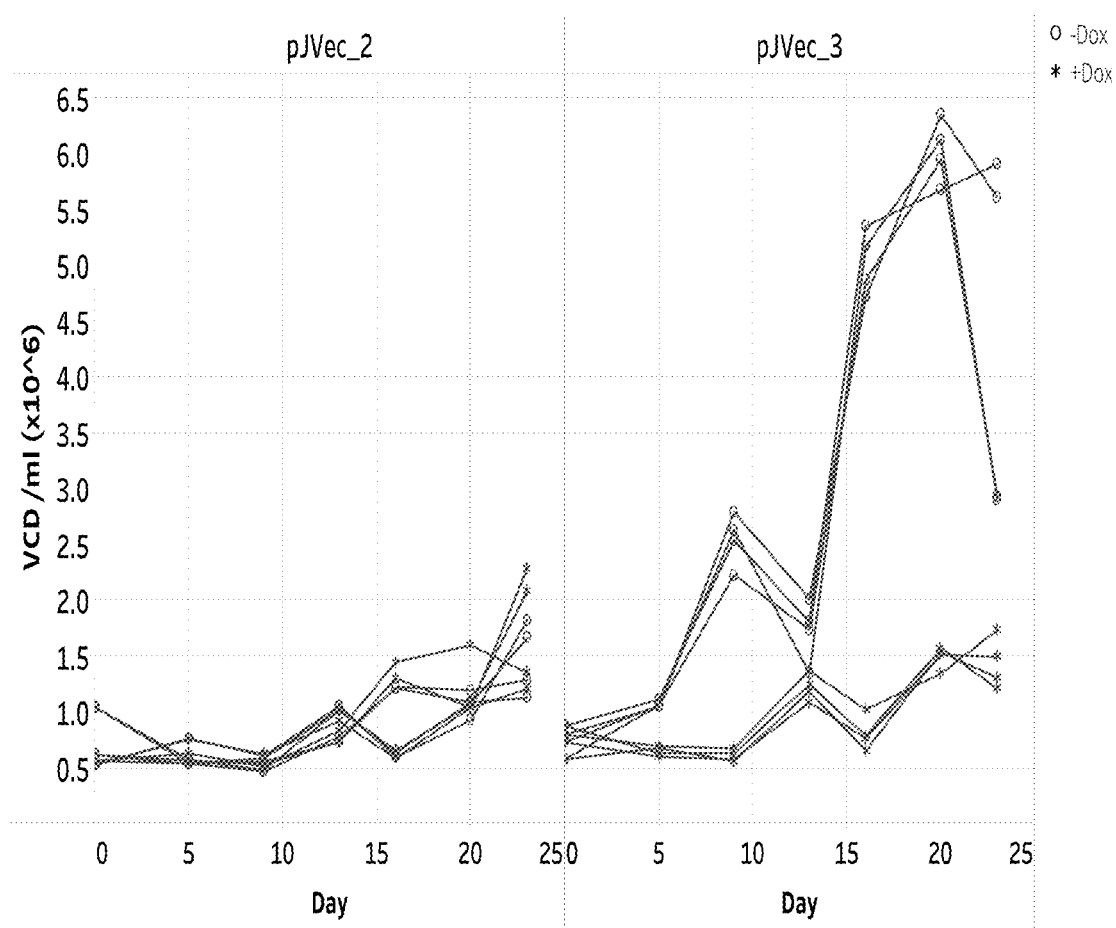
Figure 19C:
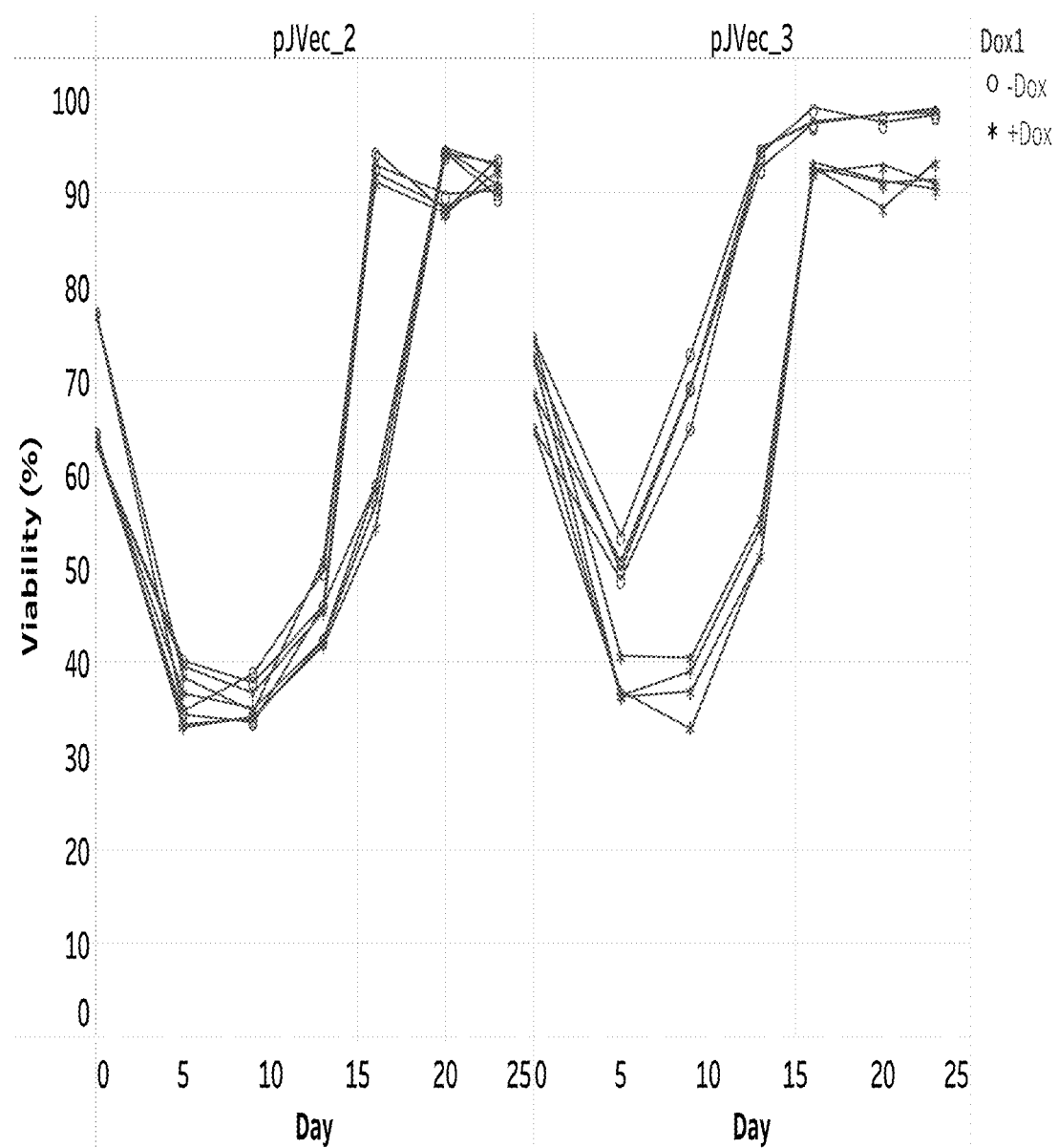
Figure 26:
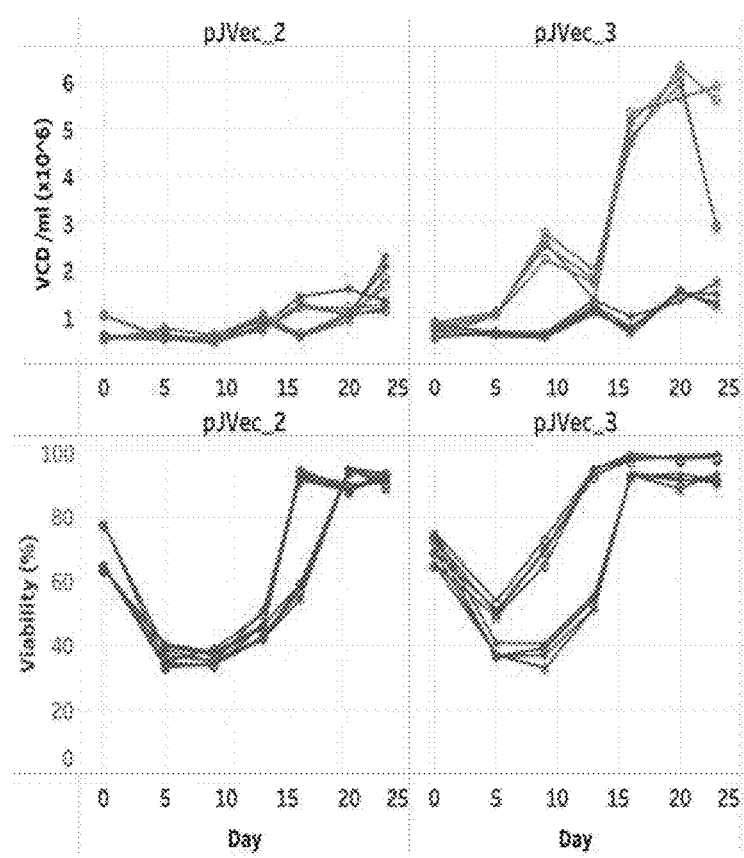
FIG. 26 shows recovery curves of Clone 9G1 pools transfected with pJVec_2 or pJVec_3 selected in CD OptiCHO medium minus glutamine (−Q), with (*) or without (O) +Dox at 75 or 100 μM L-methionine sulfoximine (MSX).

The relationship between growth and CHO-K1 cell productivity levels. To test the inducible transposon-system, 9G1 cells were stably transfected with pJVec_2 or pJVec_3, constitutive or Dox-regulatable, respectively, transposon vectors expressing Fc-A protein (FIG. 19A). As expected, Dox treatment did not alter the growth profiles of cells transfected with the constitutive pJVec_2 plasmid (FIG. 19B). Induction of recombinant Fc-A expression upon Dox treatment significantly decreased VCD and viability of pJVec_3-transfected cells during selection (FIG. 19B). FIG. 1B shows that pJVec_3-transfected cells recovered to >90% viability in 13 days when expression of Fc-A production was repressed in medium lacking Dox. In contrast, pJVec_3 cells selected in the presence of Dox required 16 days to achieve >90% viability. The cells selected at 100 µM MSX also recovered in 13 days when Fc-A protein expression was repressed (data not shown) and more than 23 days when selected in the presence of 100 µM MSX (FIG. 26). Interestingly, the growth profiles of induced pJVec_3 cells in the presence of Dox (FIG. 26) at both 75 and 100 µM MSX almost overlap with the growth profile of cells expressing Fc-A constitutively (pJVec_2, FIG. 26), implying that the observed decrease in VCD and viability upon Dox addition in pJVec_3-expressing cells were due to the metabolic burden of producing Fc-A, further supporting the hypothesis that "unnecessary" protein production can hinder robust cellular growth.

Figure 20A:
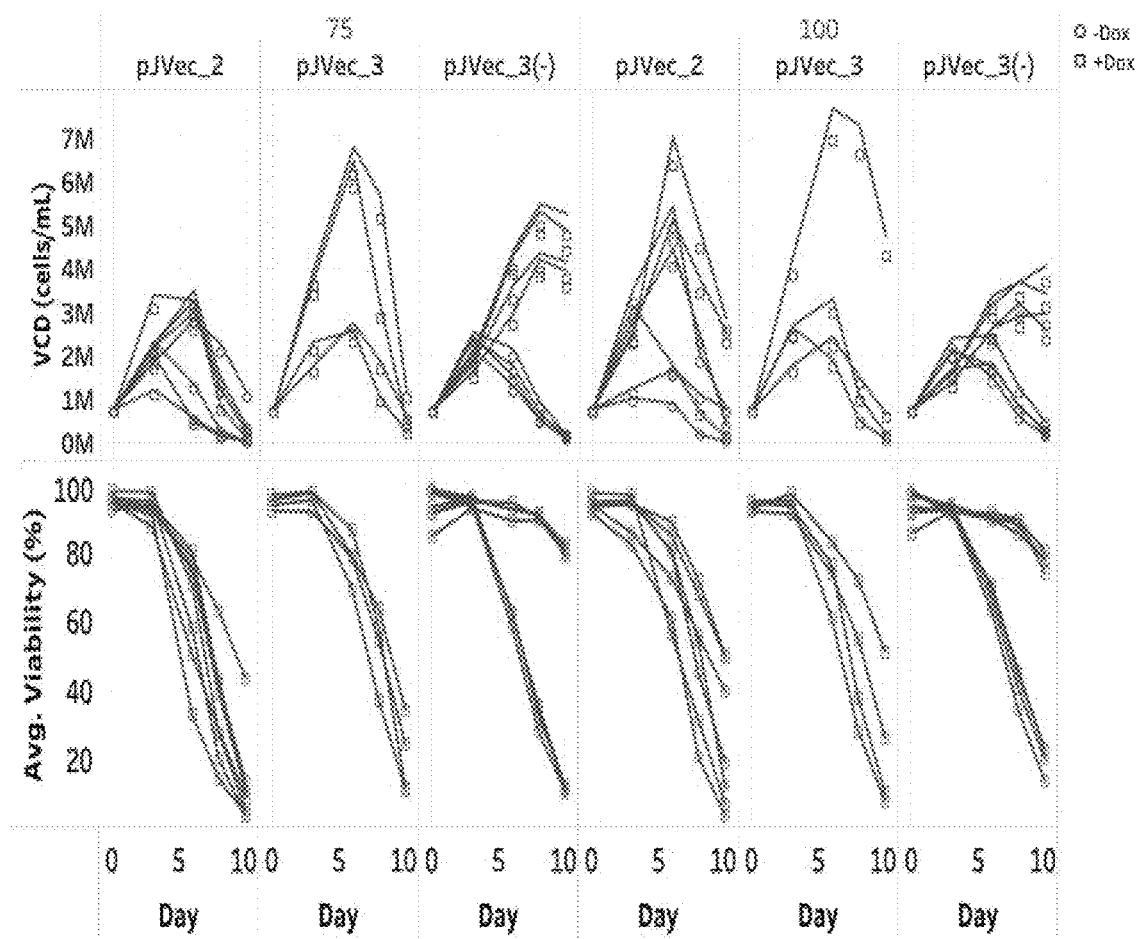
FIG. 20A-B show that an inducible transposon expression system can regulate productivity in CHOK1-TetR (GS KO) pools expressing an Fc-fusion protein during production.
Figure 20B:
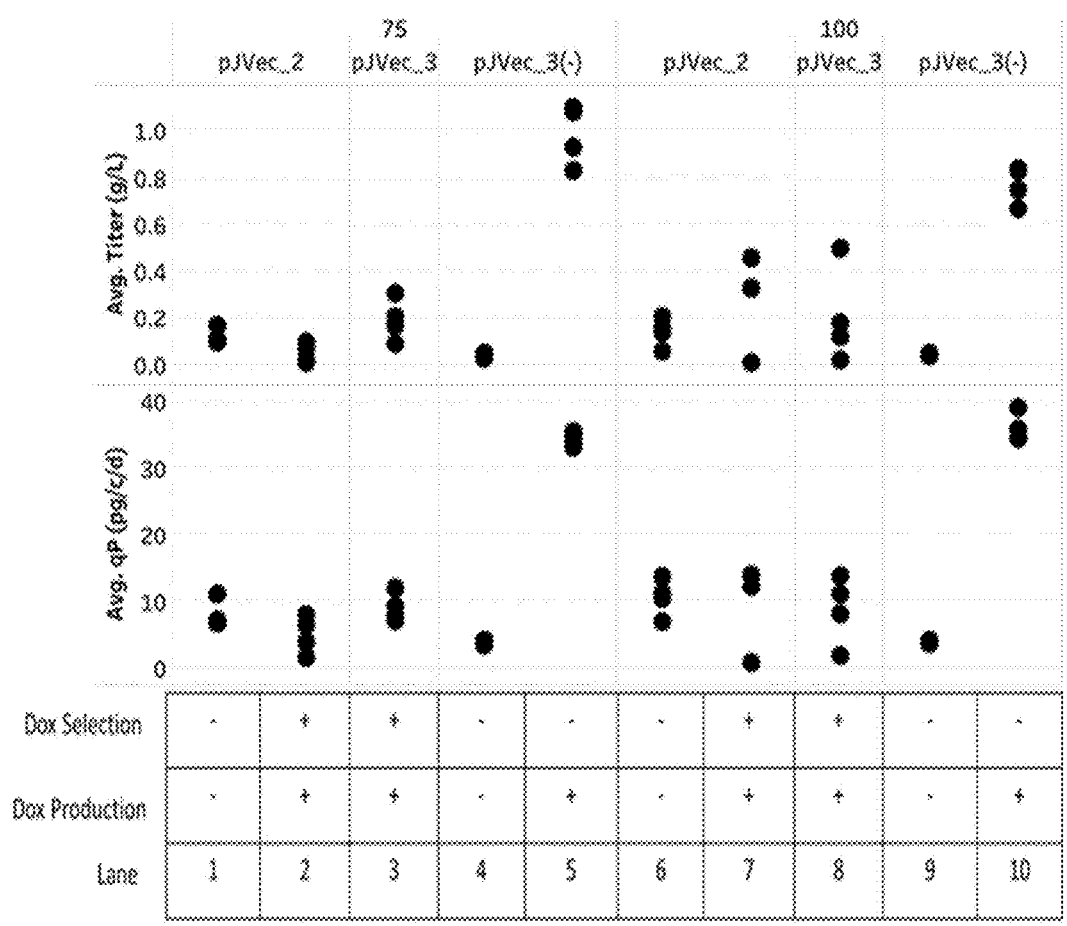

Cell pools derived as described above were put into a small-scale 10-day fed-batch process once recovered from selection. Cell lysates and supernatants were harvested on days 3 and 10 for mRNA analysis and Fc-A titer quantification, respectively. FIG. 20A shows growth and viability profiles of pJVec_2 and pJVec_3 transfected pools, and FIG. 20B shows day 10 Fc-A titers and specific productivity of pJVec_2 cells (lanes 1-2: 75 µM MSX; lanes 6-7: 100 µM MSX) and pJVec_3 cells (lanes 3-5: 75 µM MSX; lanes 8-10: 100 µM MSX). Lanes 1, 4, 6, and 9 did not receive Dox treatment while lanes 2, 3, 7, and 8 received Dox throughout selection and production, as indicated. Lanes 5 and 10 received Dox only in production. There is a 16-20 fold increase in Fc-A titer and an 8-10 fold increase in qP upon Dox addition in pJVec_3 cells (lanes 4-5 and 9-10, FIG. 20A-C). The pJVec_3(−) production cultures without Dox generally achieved lower cell densities and had lower viabilities when compared to pJVec_3(−) cultures treated with Dox for reasons that are not clear (FIG. 20A). This effect was observed in both the 75 µM MSX and 100 µM MSX treated cells. Control pJVec_2 cells were unresponsive to Dox and had titers and qP in the range of pJVec_3 cells that received Dox treatment during selection (compare lanes 1 and 2 to lane 3 and lanes 6 and 7 to lane 8, FIG. 20B). Production titers and qP in pools were similar when pools were selected at 75 µM MSX or 100 µM MSX, despite the greater impact of 100 µM MSX on VCD and viability during selection.

Next, we evaluated whether pools selected without the pressure of producing a recombinant product (culture medium lacking Dox) would have increased proportions of inherently high-producing cells within the population due to their ability to grow as well as low producers, which do not have the metabolic burden of producing as much recombinant protein as high producers. To this end, pJVec_3(−) cells that had Fc-A expression turned off during selection were induced with Dox during production (lanes 5 and 10, FIG. 20B). Cells selected in 75 µM MSX had a median titer and qP of 1.005 g/L and 33 pg/cell/day, respectively, which is about a 5-fold increase in Fc-A titer and about a 4-fold increase in qP compared to cells that had Dox present in the medium throughout selection (compare lanes 3 and 5). Likewise, cells selected in 100 µM MSX had a about a 5-fold and about a 3.6-fold increase in Fc-A titer and qP, respectively, compared to cells selected with Dox present (compare lanes 8 and 10). These data support the hypothesis that pools with higher productivities can be isolated when cells are maintained in a state that does not require excess production of a recombinant protein, likely due to their ability to grow as well as pools with low productivity.

Figure 20C:
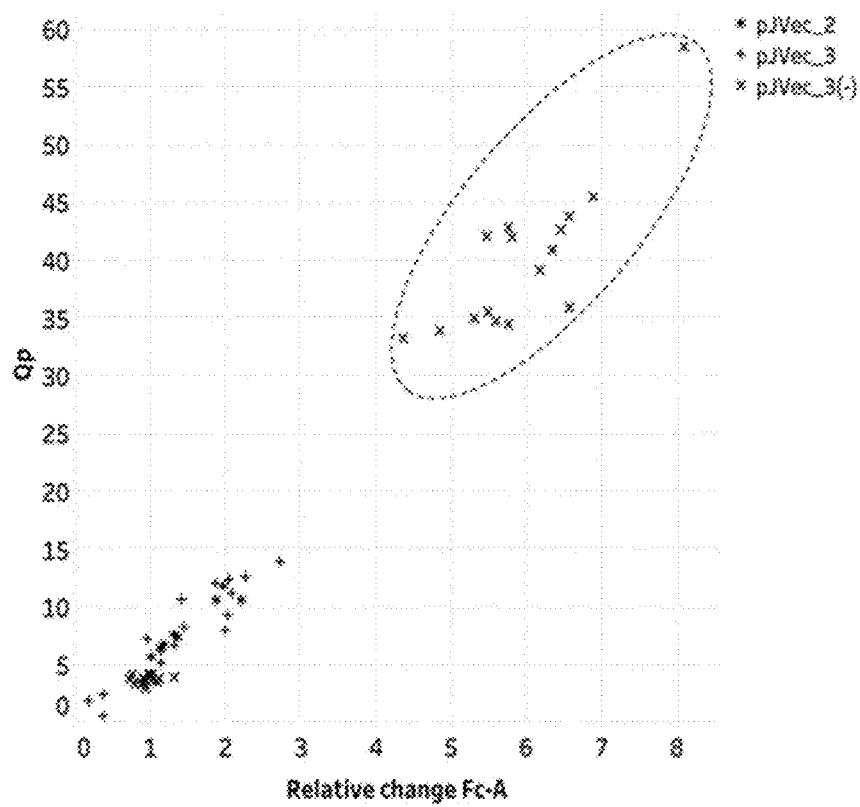
FIG. 20C shows a linear correlation between specific productivity (qP) and Fc-A mRNA levels during fed-batch production. n=4-8, for two independent experiments. pJVec3 had Dox during selection and production. pJVec3(−) transfected pools were selected in the absence of Dox. Cultures of pJVec3(−) were treated with Dox during production and are indicated by the x symbols in the dashed oval.

Relationship of Fc-fusion recombinant message levels to CHO cell productivity. Previous reports have shown qP to have a strong positive linear relationship with recombinant protein transcript levels in the cell. (See, Fomina-Yadlin, D. et al., Transcriptome analysis of a CHO cell line expressing a recombinant therapeutic protein treated with inducers of protein expression, J. Biotechnol. 212:106-115 (2015); Lee, C. J. et al., A clone screening method using mRNA levels to determine specific productivity and product quality for monoclonal antibodies, Biotechnol. Bioeng. 2009. doi: 10.1002/bit.22126). In order to determine whether mRNA levels correlated to qP under different selection conditions, RNA was purified from cells on day 3 of production from the experiment shown in FIG. 20A and Fc-A transcript levels were analyzed by quantitative RT-PCR (qPCR). All samples were normalized relative to one of the regulatable pJVec_3(−) expressing pools with Fc-A expression turned off (−Dox). Consistent with published reports, we saw a positive linear relationship between qP and relative Fc-A transcript levels (FIG. 20C). Importantly, pools of pJVec_3(−) that were induced with Dox only during production managed to increase Fc-A transcript levels by ~5-6 fold, resulting in qP values ranging from 33-59 pg/cell/day (X symbols, highlighted in dashed oval), whereas pJVec_3 pools that were constitutively induced (+ symbols) and pools transfected with constitutive plasmid pJVec_2 (* symbol) reached a maximum of ~2-fold increase in Fc-A transcript levels (FIG. 20C).

Regulatable expression of a monoclonal antibody (mAb). We then tested whether this regulated expression system would have any advantages when used to express mAbs. The schematic representation of the plasmid as depicted in FIG. 21A shows light chain (LC) and heavy chain (HC) of mAb_A driven by a murine CMV promoter linked to a rat EF-1α intron as described herein above. This vector also encodes the GS selectable marker. 9G1 cells were electroporated with pJVec_4 and a mRNA encoding a transposase. Stable transfectants were selected in medium lacking glutamine and Dox. We observed a robust recovery of all pools while mock-transfected cells declined rapidly in viability and never recovered (data not shown). As before, pools were subjected to Dox treatment in a 10-day fed-batch production to determine the level of mAb_A expression (FIG. 21B). A replicate plate was cultured in the absence of Dox as a control. There is a ~3.4-fold increase in mAb_A titer and qP upon Dox induction, verifying the function of our pJVec_4 expression vector (FIG. 21B).

Figure 21D:
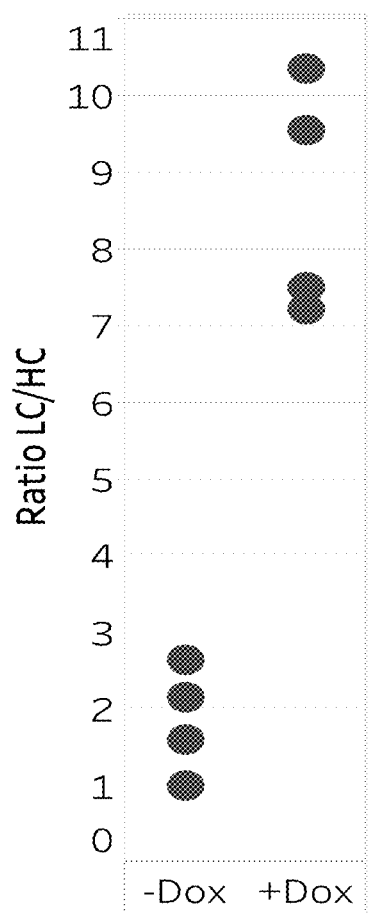
FIG. 21D shows LC/HC ratios for −Dox and +Dox conditions, respectively.

Differential mAb LC and HC transcript levels during production. To gain a deeper understanding of mAb production with the pJVec_4 expression vector, levels of LC and HC mRNA expression was analyzed by qPCR. One replicate of the pJVec_4 pools that did not receive Dox was used as a control sample. When we looked at relative expression of LC or HC mRNA as a function of qP, we saw two distinct populations, separated by mAb_A expression being turned on or off, i.e. +Dox or −Dox, respectively (FIG. 21C), suggesting that increased LC or HC expression led to higher qP values. While the expression of both LC and HC transcripts increase, the level by which LC increases is more than that of HC (FIG. 21C, note the difference in scale). To show this another way, the ratio of LC to HC was calculated and we show that, on average, the increase in ratio of LC to HC is ~4.5 times comparing −Dox and +Dox (FIG. 21D). We hypothesized that the polyA sequence in pJVec_4 downstream of LC was not sufficient for transcription termination and thus, the transcriptional unit of LC was interfering with that of HC (Eszterhas, S. K. et al., Transcriptional interference by independently regulated genes occurs in any relative arrangement of the genes and is influenced by chromosomal integration position, Mol. Cell Biol. 22(2):469-479 (2002)), resulting in the observed imbalance of LC and HC mRNA levels and high LC/HC ratios post-induction.

To test this hypothesis, the polyA sequence downstream of LC in pJVec_4 was replaced with a human β-globin polyA/terminator sequence. (Dye, M J and Proudfoot, N J, Multiple transcript cleavage precedes polymerase release in termination by RNA polymerase II, Cell 105(5):669-681 (2001)). This construct, pJVec_5 (FIG. 22A) along with transposase mRNA, was used to transfect Clone 9G1 and three other GS KO clonal cell lines stably expressing the TetR protein (FIG. 22B). The parental GS KO hosts not expressing TetR were included as a control and as expected, when selected in medium lacking glutamine, Dox treatment did not alter the recovery profile of these pools. In contrast, in all four TetR-GS KO clonal cell lines that were transfected with pJVec_5, we observed decreased cell growth when pools were selected in the presence of Dox compared to its −Dox control, consistent to what was described in FIG. 1B (FIG. 22B). Several pJVec_5 pools selected in the absence of Dox were then placed in +Dox conditions, and the doubling time was measured for a 4-day culture. The doubling time during passage increased from 18.6 hours to 21.3 hours (n=2) upon Dox treatment indicating the additional protein expression burden decreased cell growth even after going through the selection process.

Figure 23A:
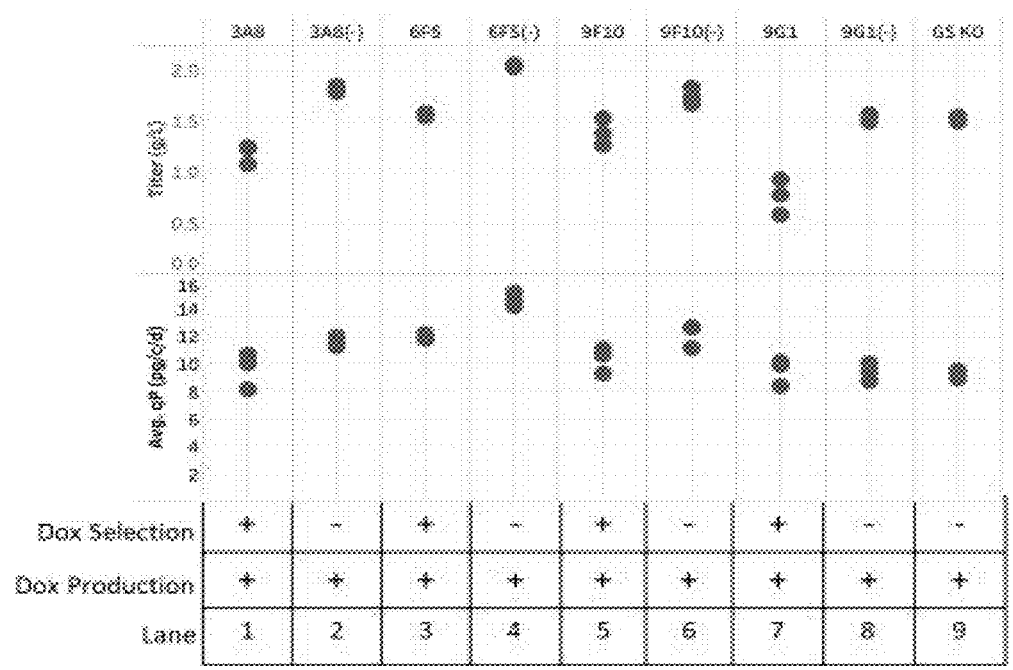
FIG. 23A-C shows results from an experiment.
Figure 23B:
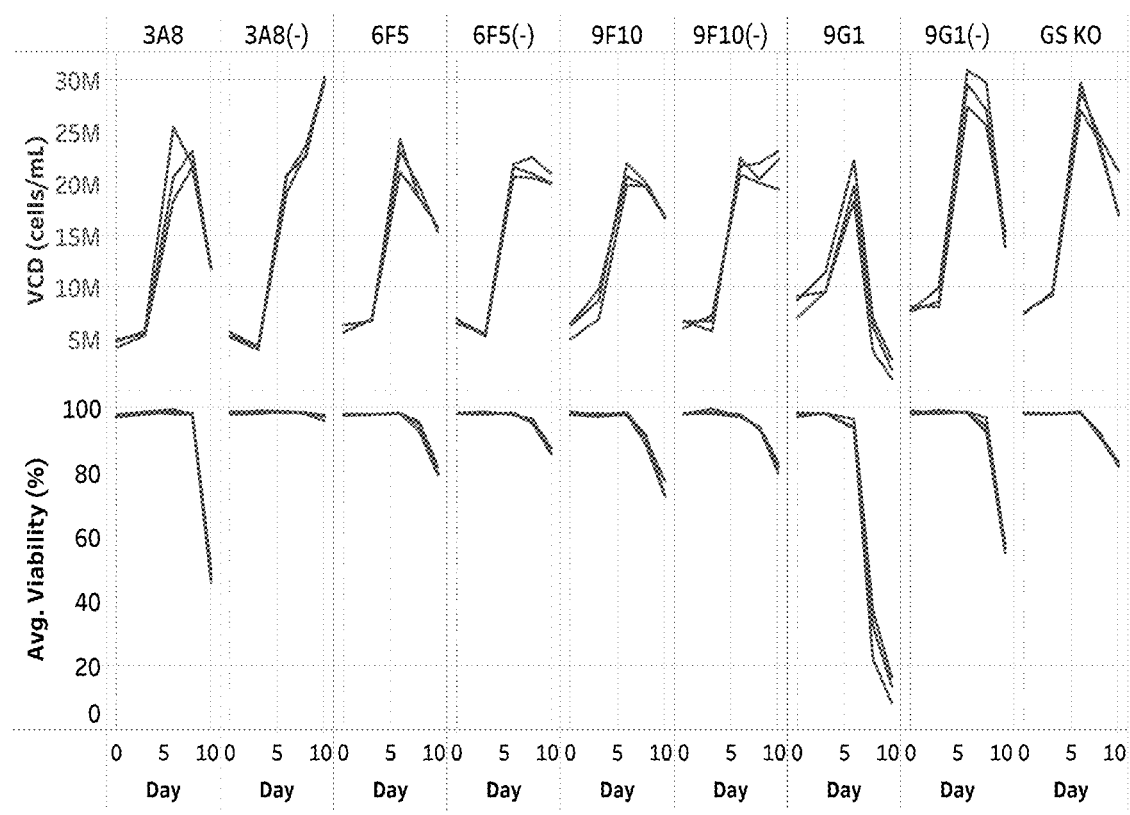
Figure 23C:
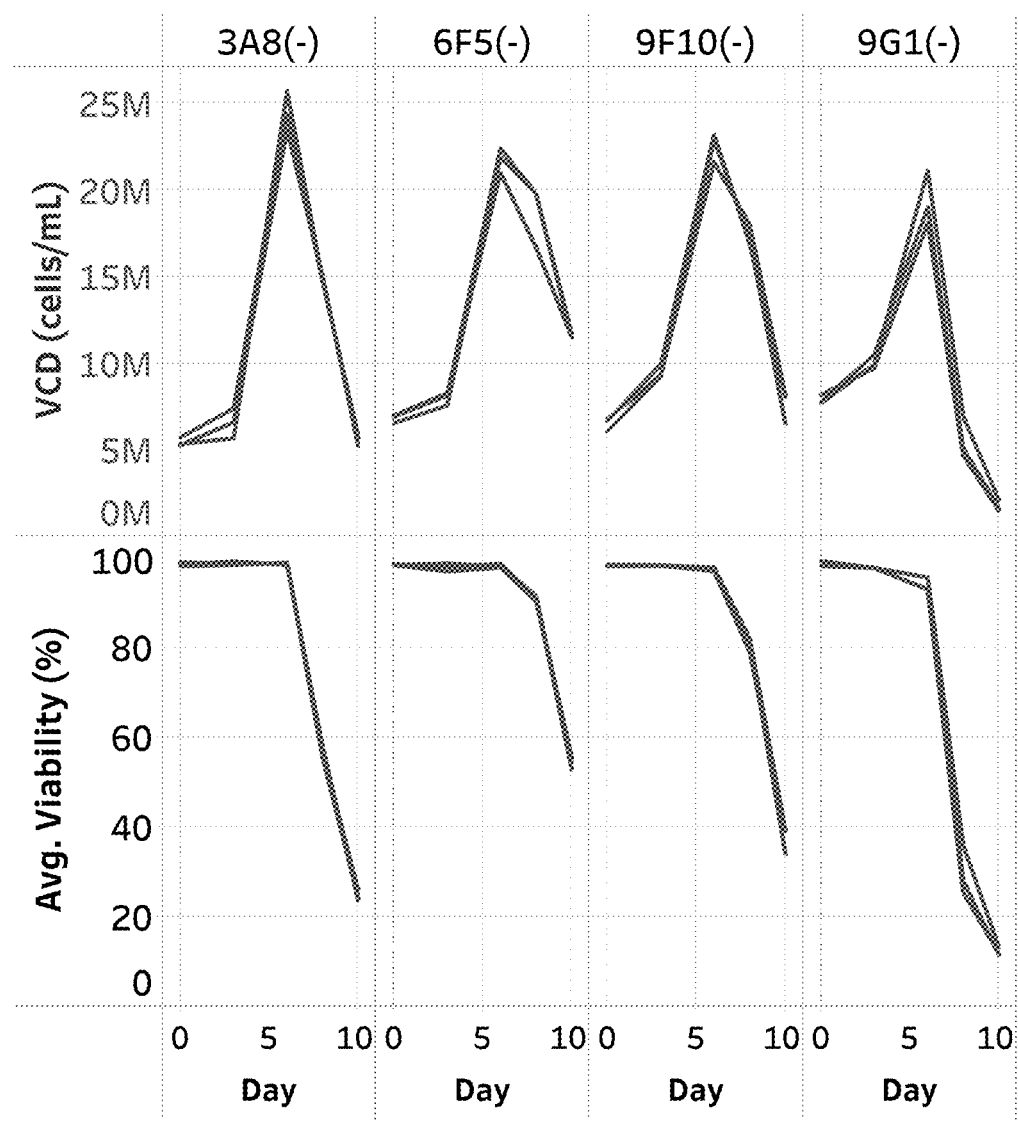
Figure 27A:
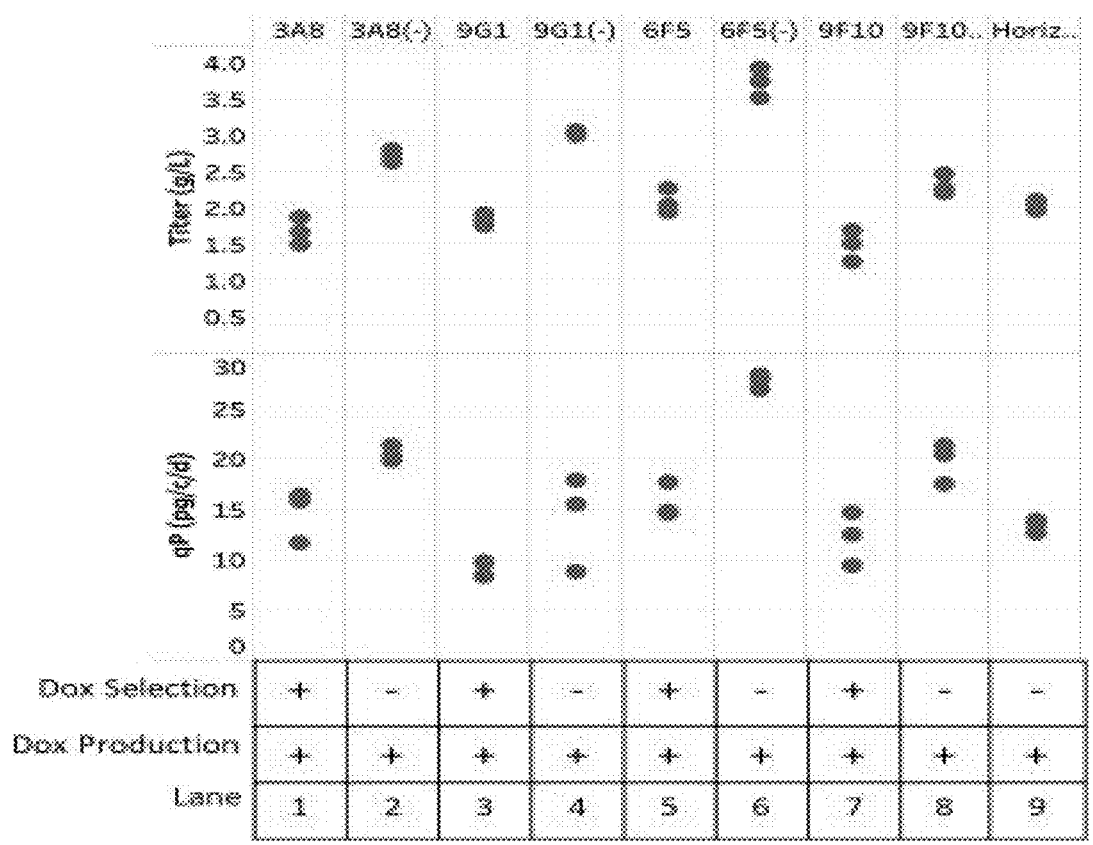
FIG. 27A shows Day 10 titers/qP from a fed-batch production in a chemically defined culture medium without growth factors or other proteins, with Hyclone feeds A/B. n=3.
Figure 27B:
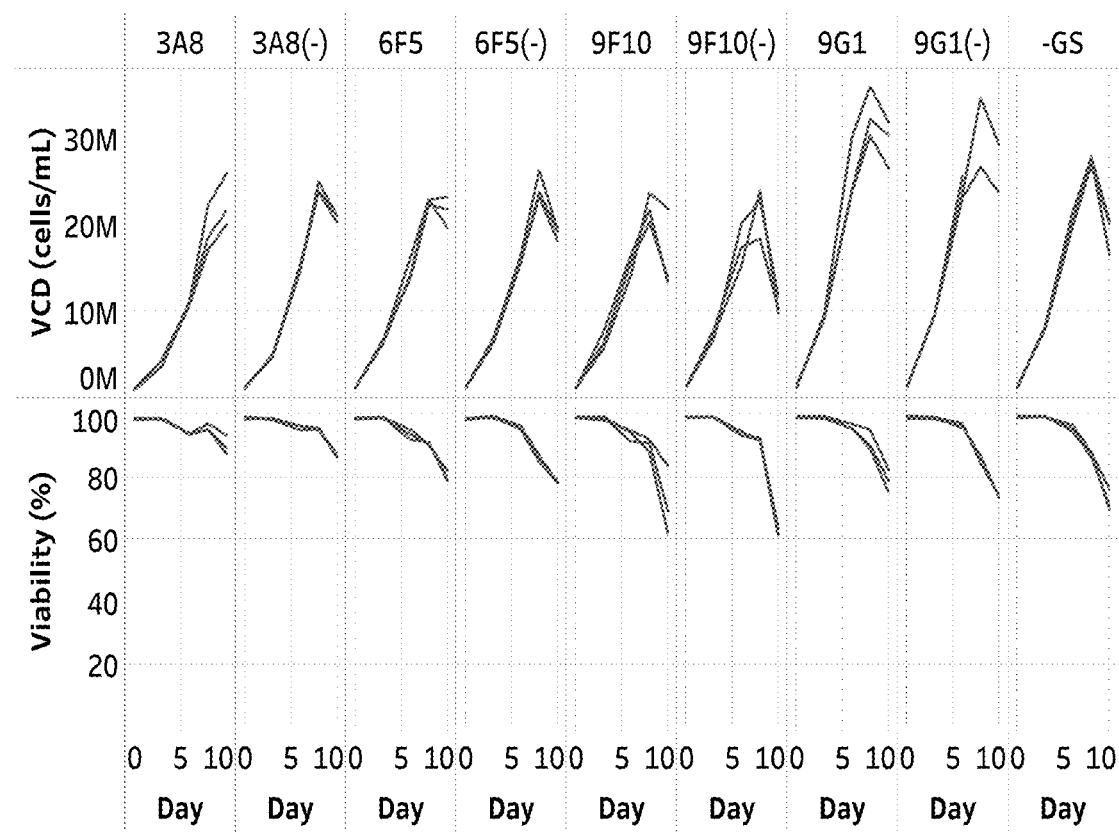
FIG. 27B shows representative growth curves during production.

Improved productivity in pJVec_5 pools selected and maintained in the absence of doxycycline (Dox). Pools of pJVec_5-transfected cells were then subjected to a 10-day fed-batch production assay. Pools that were selected in the presence of Dox were maintained in that fashion throughout the production assay (FIG. 5A, lanes 1, 3, 5, 7). Additionally, pools that were selected in the absence of Dox were treated with Dox during production to induce mAb_A expression (FIG. 23A, lanes 2, 4, 6, 8). These pools had increased qP and titers compared to pools that had mAb_A expressed constitutively; there was about a 1.3- to 2-fold increase in mAb_A titer and about a 1.2-fold increase in qP, depending on which clonal cell line studied (FIG. 23A). The GS KO host not expressing TetR had similar or lower titers and qP compared to TetR-GS KO cell lines that were selected without the added pressure of expressing mAb_A (FIG. 23A, compare lane 9 to lanes 1, 3, 5, 7). All pools maintained high viabilities up to day 6 of production, after which we started to see a decline in cell growth and viability in some cell lines (FIG. 23B). Additional production cultures with these pools in proprietary production medium and feeds achieved substantially high titers of up to 4 g/L and qP values up to 28 pg/c/d (FIG. 27A). Those cultures selected in the absence of dox had the highest titers and qP values. These data indicate that the highest titer mAb expressing pools were selected in the absence of the inducer.

Figure 24A:
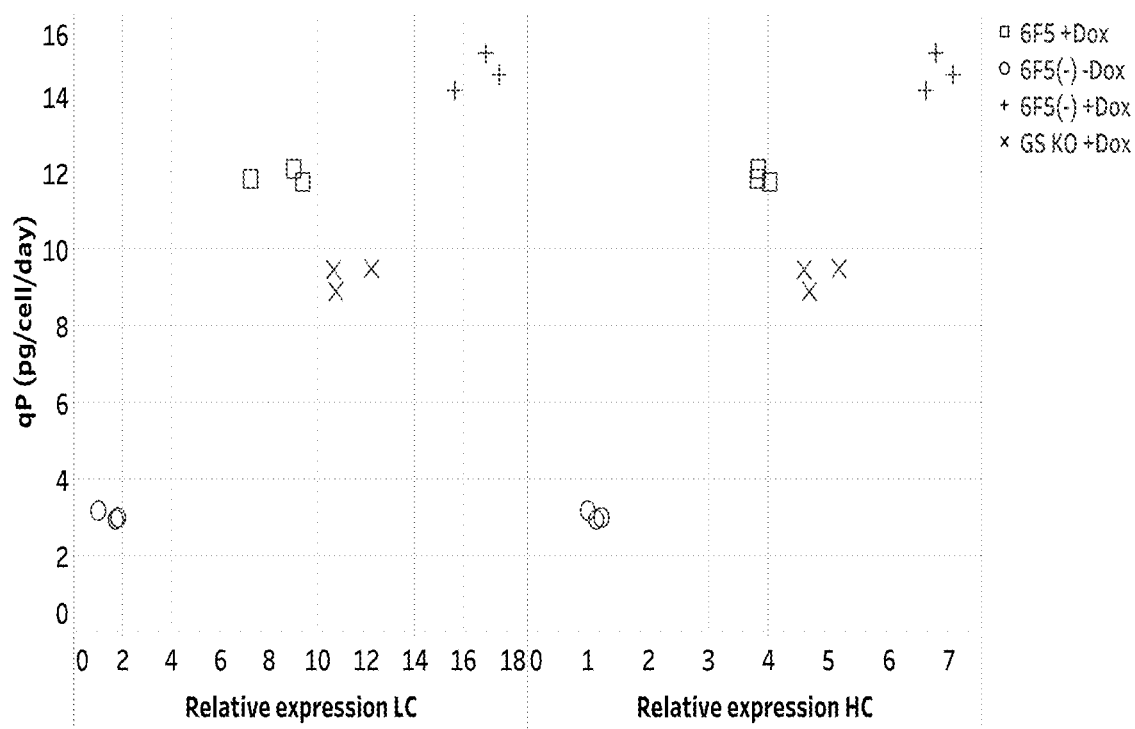
FIG. 24A-B show qPCR analysis (FIG. 24A) of mAb_A LC and HC expression during production. n=3, Data shown are representative of 2 independent experiments.
Figure 24B:
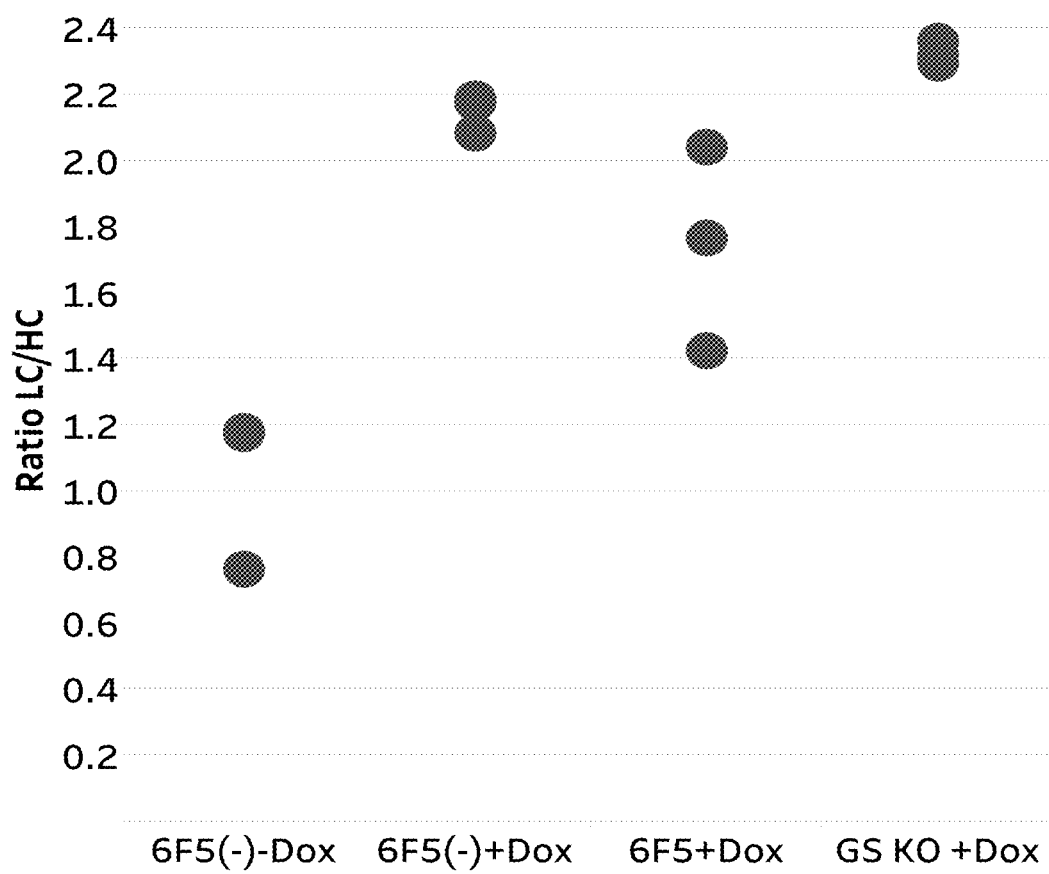

Balanced LC/HC ratios correlates to increased titers and specific productivity (qP). The mAb_A LC and HC transcript levels were analyzed by qPCR to gain insight into the increased titer and qP we observed when we utilized pJVec_5 compared to pJVec_4. We focused on 6F5 pools because that cell line gave us the highest titers and qP among the ones that were tested (FIG. 23A). Wild type GS KO hosts were also analyzed as a control. A 6F5 −Dox pool was used as a reference sample (circle, FIG. 24A). We saw a positive linear relationship between qP and both LC and HC transcript levels, although the level by which LC increases is more than that of HC (FIG. 24A, note the difference in scale). The LC/HC ratio on average was similar for the induced 6F5 pools and the GS KO pools transfected with pJVec_5 vector (2.2, 1.8 and 2.3). The LC/HC ratio of uninduced 6F5 was lower as would be expected from reduced transcription from LC transcription unit interfering the HC expression. (FIG. 24B). This is in contrast to pools transfected with pJVec_4 where we saw that the LC/HC ratio for pools induced only during production to be about 8.5 (FIG. 21D). Hence, consistent with our hypothesis, our data imply that a more balanced LC/HC ratio seen with pJVec_5 pools through usage of a more efficient polyA/terminator signal reduced transcriptional interference and increased titers and qP. We observed that the relative expression of LC and HC transcript levels in GS KO host not expressing TetR were lower compared to 6F5(−)+Dox pools, as were their qP values, further validating the use of an inducible transposon system to find high producing pools/clones during the stable cell line development process.

Discussion We found that limiting recombinant protein expression during cell line selection yielded higher expressing pools compared to pools that were selected with constitutive protein expression. This effect was observed for both an Fc-fusion protein and a mAb. In addition, four different TetR expressing clones displayed similar results. The magnitude of this effect was up to approximately 1.8 fold for the mAb pools to over 2-fold for the Fc-fusion molecule. These data are consistent with data from microbial systems where the metabolic burden of "unnecessary" protein expression can result in selection of lower expressing clones.

Even innocuous proteins such as beta-galactosidase and green fluorescent protein limit growth when expressed at sufficiently high levels in microbial systems. Scott et al., Interdependence of cell growth and gene expression: origins and consequences, Science 330(6007):1099-1102 (2010); Miroux, B et al., Over-production of proteins in *Escherichia coli* mutant hosts that allow synthesis of some membrane proteins and globular proteins at high levels, J. Mol. Biol. 260:289-298 (1996)).

For mammalian cells this effect has been described for toxic proteins. (See, Misaghi, S. et al., It's time to regulate:

Coping with product-induced nongenetic clonal instability in CHO cell lines via regulated protein expression, Biotechnol Prog. 2014; 30(6):1432-1440 (2014); Jones, J. et al., Optimization of tetracycline-responsive recombinant protein production and effect on cell growth and ER stress in mammalian cells, Biotechnol Bioeng. 91(6):722-732 (2005)).

Neither of the proteins utilized in this paper had obvious toxicity, and stable cell lines with constitutive promoters have been isolated with both molecules (data not shown). A recent report using a cumate-inducible system showed a similar result to those described in this report where restricting expression to only the production phase yielded pools expressing higher levels of protein compared to constitutive expression. (Poulain, A. et al., Rapid protein production from stable CHO cell pools using plasmid vector and the cumate gene-switch, J Biotechnol. 255:16-27 (2017)). However, their results can potentially be explained by the observation that their inducible promoter appeared to be significantly more powerful than the constitutive promoters they used for comparison.

We observed a close correlation between qP and recombinant protein mRNA levels (FIGS. 20C and 24A). Consistent with our finding, a recent paper showed that reducing the expression of the neomycin resistance (NeoR) selectable marker mRNA improves growth and expression of a recombinant antibody. In that example, the NeoR mRNA accounted for 5.63% of translated mRNAs on day 3 and 5.41% on day 6. Treatment of siRNA depleted NeoR mRNA 87-92% resulting in an increase in both VCD and titer. (Kallehauge et al., Ribosome profiling-guided depletion of an mRNA increases cell growth rate and protein secretion, Sci. Rep. 7:40388 (2017)). Fomina-Yadlin et al. also showed strong correlation between mRNA levels and qP for a recombinant Fc-fusion protein and up to 45% of total cellular mRNA levels encoded the recombinant transcript for cultures treated with chemicals that induce gene expression. (Fomina-Yadlin, D. et al., Transcriptome analysis of a CHO cell line expressing a recombinant therapeutic protein treated with inducers of protein expression, J. Biotechnol. 212:106-115 (2015)).

We did not observe substantial differences in growth during production phase between pools selected while constitutively expressing recombinant protein compared to those only expressing recombinant protein during production phase. In fact, some of the cultures selected in the presence of Dox achieved higher VCDs and viability in production. The increase in titer observed for cultures that were only treated with Dox during production was primarily associated with an increase in specific productivity. This phenomenon is similar to that observed with *E. coli* expression, where constitutive expression leads to expression instability and outgrowth of mutants with reduced expression or mutations that allow the cells to tolerate high levels of protein expression. (Miroux, B et al., Over-production of proteins in *Escherichia coli* mutant hosts that allow synthesis of some membrane proteins and globular proteins at high levels, J. Mol. Biol. 260:289-298 (1996); Baneyx F., Recombinant protein expression in *Escherichia coli*, Curr. Opin. Biotechnol. 10(5):411-21 (1999)). In the pools selected in the presence of Dox, we hypothesize that outgrowth of lower expressing clones during the selection phase accounts for the lower expression compared with those selected in the absence of Dox. This is consistent with the observation that the doubling time of cultures selected in the absence of Dox increases when those cultures are treated with Dox. Two practical advantages of inducible systems were apparent from this work including higher titers and more rapid generation of recombinant protein expressing pools by way of faster recovery during selection.

We claim:

1. A recombinant expression vector, comprising:
   (a) a first expression cassette, comprising:
      (i) a control sequence comprising:
         (1) a murine cytomegalovirus (mCMV) enhancer sequence, comprising a mCMV enhancer element (mCMV-E) and a CMV promoter (CMV-P) sequence at its 3' end, operably linked 5' to a rat EF-1alpha intron sequence;
         (2) an intervening first leader sequence operably linked, 3' to the CMV-P sequence of the mCMV enhancer sequence, and 5' to the rat EF-1alpha intron sequence; and
         (3) a second leader sequence operably linked 3' to the rat EF-1alpha intron sequence;
      (ii) an open reading frame encoding a first immunoglobulin subunit operably linked to the control sequence; and
      (iii) a first polyadenylation site operably linked 3' to the open reading frame;
   (b) a second expression cassette 3' to the first expression cassette, comprising:
      (i) a control sequence comprising a promoter;
      (ii) an open reading frame encoding a second immunoglobulin subunit operably linked to the promoter; and
      (iii) a second polyadenylation site operably linked 3' to the open reading frame; and
   (c) a transcription termination sequence 3' to the first expression cassette and 5' to the second expression cassette.

2. The vector of claim 1, wherein the control sequence (i) of the second expression cassette comprises:
   (1) a mCMV enhancer sequence, comprising a mCMV enhancer element (mCMV-E) and a CMV promoter (CMV-P) sequence at its 3' end, operably linked 5' to a rat EF-1alpha intron sequence;
   (2) an intervening first leader sequence operably linked, 3' to the CMV-P sequence of the mCMV enhancer sequence, and 5' to the rat EF-1alpha intron sequence; and
   (3) a second leader sequence operably linked 3' to the rat EF-1alpha intron sequence.

3. The vector of claim 1, further comprising:
   (d) a third expression cassette comprising:
      (i) a weak constitutive promoter, operably linked to an open reading frame encoding a selectable marker; and
      (ii) a polyadenylation site operably linked 3' to the open reading frame.

4. The vector of claim 3, wherein the weak constitutive promoter is a deleted SV40 promoter.

5. The vector of claim 4, wherein the deleted SV40 promoter comprises the nucleotide sequence of SEQ ID NO:53.

6. The vector of claim 4, wherein the deleted SV40 promoter comprises the nucleotide sequence of SEQ ID NO:46.

7. The vector of claim 3, wherein the selectable marker is glutamine synthetase, puromycin resistance, neomycin resistance, zeomycin resistance, or dihydrofolate reductase.

8. The vector of claim 3, wherein the selectable marker is glutamine synthetase.

9. The vector of claim 3, wherein the selectable marker is encoded by the nucleotide sequence of SEQ ID NO:49, or a degenerate DNA sequence thereof.

10. A mammalian host cell, in culture, comprising the recombinant expression vector of claim 1.

11. The mammalian host cell of claim 10, wherein the mammalian host cell is a CHO cell.

12. The mammalian host cell of claim 11, wherein the CHO cell is a CHO-K1 cell, a DXB11 cell, or a DG44 cell.

13. A method of producing a protein of interest comprising a first immunoglobulin subunit and a second immunoglobulin subunit, in vitro, comprising culturing the mammalian host cell of claim 10 in an aqueous medium under physiological conditions permitting expression of the first immunoglobulin subunit and the second immunoglobulin subunit; and recovering the protein of interest from the medium.

* * * * *